US010449230B2

(12) United States Patent
Hamill et al.

(10) Patent No.: US 10,449,230 B2
(45) Date of Patent: Oct. 22, 2019

(54) POLYMYXIN DERIVED CELL PENETRATING SCAFFOLDS

(71) Applicant: The Regents of the University of California, Oakland, CA (US)

(72) Inventors: Kristina Hamill, La Jolla, CA (US); Jeffrey D. Esko, San Diego, CA (US); Lisa McCoy, La Jolla, CA (US); Yitzhak Tor, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/727,397

(22) Filed: Oct. 6, 2017

(65) Prior Publication Data
US 2018/0099022 A1    Apr. 12, 2018

Related U.S. Application Data

(60) Provisional application No. 62/405,066, filed on Oct. 6, 2016.

(51) Int. Cl.
| *A61K 38/12* | (2006.01) |
| *A61K 47/69* | (2017.01) |
| *A61K 47/62* | (2017.01) |
| *A61K 47/64* | (2017.01) |
| *C07K 7/62* | (2006.01) |
| *A61K 38/00* | (2006.01) |
| *G01R 33/46* | (2006.01) |

(52) U.S. Cl.
CPC .............. *A61K 38/12* (2013.01); *A61K 47/62* (2017.08); *A61K 47/64* (2017.08); *A61K 47/6911* (2017.08); *A61K 47/6939* (2017.08); *C07K 7/62* (2013.01); *A61K 38/00* (2013.01); *G01R 33/46* (2013.01)

(58) Field of Classification Search
None
See application file for complete search history.

(56) References Cited

U.S. PATENT DOCUMENTS

| 4,160,452 A | 7/1979 | Theeuwes |
| 4,256,108 A | 3/1981 | Theeuwes |
| 4,265,874 A | 5/1981 | Bonsen et al. |
| 4,749,800 A | 6/1988 | Jobe et al. |
| 5,177,059 A * | 1/1993 | Handley ............... A61K 47/61 514/2.4 |
| 6,468,798 B1 | 10/2002 | Debs et al. |
| 6,471,996 B1 | 10/2002 | Sokoll et al. |
| 6,472,375 B1 | 10/2002 | Hoon et al. |
| 6,525,182 B1 | 2/2003 | Goodman et al. |
| 6,537,785 B1 | 3/2003 | Canfield |
| 6,579,696 B1 * | 6/2003 | Shekhani ............. G01N 33/532 435/68.1 |
| 8,071,535 B2 | 12/2011 | Tor et al. |
| 8,865,664 B2 | 10/2014 | Bera et al. |
| 9,757,468 B2 | 9/2017 | Esko et al. |
| 9,889,182 B2 | 2/2018 | Esko et al. |
| 2005/0208090 A1 | 9/2005 | Keimel et al. |
| 2007/0185040 A1 | 8/2007 | Tor et al. |
| 2008/0305077 A1 | 12/2008 | Frey, II et al. |
| 2009/0047234 A1 | 2/2009 | Touitou et al. |
| 2012/0189601 A1 | 7/2012 | Esko et al. |
| 2013/0053337 A1 | 2/2013 | Schweizer et al. |
| 2014/0050777 A1 * | 2/2014 | Tam .................. A61K 9/127 424/450 |
| 2018/0086782 A1 | 3/2018 | Esko et al. |

FOREIGN PATENT DOCUMENTS

| WO | WO2005/025513 | 3/2005 |
| WO | WO2008/049897 | 5/2008 |
| WO | WO2011/034951 | 3/2011 |
| WO | WO2014/159878 | 10/2014 |

OTHER PUBLICATIONS

Hamill et al. "Polymyxins facilitate entry into mammalian cells," Chem. Sci., 2016, 7, 5059-5068 (Year: 2016).*
Lu et al. "Human oligopeptide transporter 2 (PEPT2) mediates cellular uptake of polymyxins," J Antimicrob Chemother 2016; 71: 403-412 (Year: 2016).*
Sakura et al. "Synthesis of cyclic peptide antibiotic polymyxin B derivatives," Peptide Science (1999), 36th, 413-416 (Year: 1999).*
McCoy et al. "Polymyxins and Analogues Bind to Ribosomal RNA and Interfere with Eukaryotic Translation in Vitro," ChemBioChem 2013, 14, 2083-2086 (Year: 2013).*
Anderson et al., "A View of Acidic Intracellular Compartments," Journal Cell Biol., vol. 106, pp. 539-543, Mar. 1988.
Appelqvist, H.; Waster, P.; Kagedal, K.; Ollinger, K., "The Lysosome: From Waste Bag to Potential Therapeutic Target," J. Mol. Cell Biol. 2013, 5, 214-226.
Baba, M. et al., "HIV-1-Specific Reverse Transcriptase Inhibitors," Chapter 11 in "Anti-AIDS Drug Development: Challenges, Strategies and Prospects," P. Mohan and M. Baba (Editors), Harwood Academic Publishers GmbH, Switzerland, 1995, pp. 239-267.
Bai et al., "An animal cell mutant defective in heparan sulfate hexuronic acid 2-O-sulfation," Journal Biol. Chem., vol. 271(30), pp. 17711-17717, Jul. 26, 1996.
Bai et al., "Chinese Hamster Ovary Cell Mutants Defective in Glycosaminoglycan Assembly and Glucuronosyltransferase I," J. Biol. Chem. 1999, 274, 13017-13024.
Baker et al., "Synthesis and Anti-HIV Activity of Guanidinoglycosides," J. Org. Chem., 2000, 65:9054-9058.
Bame et al., "Sulphated and undersulphated heparin sulphate proteogycans in a Chinese hamster ovary cell mutant defective in N-sulphotransferase," Biochemical J., 1994, 303:81-87.
Bera et al., "Synthesis and Antibacterial Activities of Amphiphilic Neomycin B-based Bilipid Conjugates and Fluorinated Neomycin B-based Lipids," Molecules 2012, 17, 9129-1941.

(Continued)

*Primary Examiner* — Christina Bradley
(74) *Attorney, Agent, or Firm* — Fish & Richardson P.C.

(57) ABSTRACT

Provided are transporters based on polymyxin B. Also provided are methods of using the transporters for intracellular delivery of cargo and methods of enhancing intracellular uptake of cargo.

17 Claims, 18 Drawing Sheets

(56) References Cited

OTHER PUBLICATIONS

Berge et al., "Pharmaceutical Salts," J Pharm Sci., 1977, 66(1):1-19.
Bishop et al., "Heparan Sulphate Proteoglycans Fine-Tune Mammalian Physiology," Nature 2007, 446, 1030-1037.
Biswas et al., "Liposomes Loaded with Paclitaxel and Modified with Novel Triphenylphosphonium-PEG-PE Conjugate Possess Low Toxicity, Target Mitochondria and Demonstrate Enhanced Antitumor Effects In Vitro and In Vivo," J. Control. Release, 2012, 159, 393-402.
Blount et al., "A Tale of Two Targets: Differential RNA Selectivity of Nucleobase-Aminoglycoside Conjugates," Chembiochem, 2006, 7:1612-1621.
Boesze-Battaglia et al., "Cell membrane lipid composition and distribution: Implications for cell function and lessons learned from photoreceptors and platelets," J. Experimental Biol., 200: pp. 2927-2936, 1997.
Brinkley, "A brief survey of methods for preparing protein conjugates with Dyes, Haptens, and Cross-linking Reagents," Bioconjugate Chem., 1992, 3:2-13.
Caesar et al., "Membrane Interactions of Cell-Penetrating Peptides Probed by Tryptophan Fluorescence and Dichroism Techniques: Correlations of Structure to Cellular Uptake," Biochemistry, 2006, 45:7682-7692.
Chambers, "Aminoglycosides," Goodman & Gilman's "The Pharmacological Basis of Therapeutics" (Brunton, L. L., Lazo, J. S., and Parker, K. L., eds) 11th Ed., 2006, pp. 1155-1171, McGraw-Hill, New York, 19 pages.
Chang et al., "Clinical Development of Liposome-Based Drugs: Formulation, Characterization, and Therapeutic Efficacy," Int. J. Nanomed. 2012, 7, 49-60.
Check, E., "HIV Drug Resistance Triggers Strategic Switch," Nature 424: 361 (Jul. 24, 2003).
Chung et al., "Dendritic Oligoguanidines as Intracellular Translocators," Biopolymers, 2004, 76:83-96.
Console et al., "Antennapedia and HIV Transactivator of Transcription (TAT) "Protein Transduction Domains" Promote Endocytosis of High Molecular Weight Cargo upon Binding to Cell Surface Glycosaminoglycans," J. Biol. Chem. 2003, 278, 35109-35114.
Cryan et al., "Increased Intracellular Targeting to Airway Cells Using Octaarginine-Coated Liposomes: In Vitro Assessment of Their Suitability for Inhalation," Mol. Phar. 2006, 3, 104-112.
De Clercq, Erik, "From Anti-HIV Agents to Anti-AIDS Chemotherapy: A Critical Appraisal," Chapter 1 in "Anti-AIDS Drug Development: Challenges, Strategies and Prospects," P. Mohan and M. Baba (Editors), Harwood Academic Publishers GmbH, Switzerland, 1995, pp. 1-37.
Desnick, "Enzyme Replacement and Enhancement Therapies for Lysosomal Disease," J. Inherit. Metab. Dis., 2004, 27:385-410.
Deutscher et al., "Translocation across golgi vesicle membranes: A CHO glycosylation mutant deficient in CMP-sialic acid transport," Cell, 1984, 39:295-299.
Dietz et al., "Delivery of bioactive molecules into the cell: the Trojan horse approach," Mol. Cell. Neurosci., 2004, 27:85-131.
Diwu et al., A Novel Acidotopic pH Indicator and its Potential Application in Labeling Acidic Organelles of Live Cells, Chem. Biol. 1999, 6, 411-418.
Dix et al., "Cooperative, Heparan Sulfate-Dependent Cellular Uptake of Dimeric Guanidinoglycosides," ChemBioChem, 2010, 11(16):2302-2310.
Elson-Schwab et al., "Guanidinylated Neomycin Delivers Large, Bioactive Cargo into Cells through a Heparan sulfate-dependent Pathway," J. Biol. Chem., 2007, 282(18):13585-13591.
Esko et al., "Animal cell mutants defective in glycosaminoglycan biosynthesis," Proc. Natl. Acad. Sci. U.S.A., 1985, 82:3197-3201.
Esko et al., "Order Out of Chaos: Assembly of Ligand Binding Sites in Heparan Sulfate," Annu. Rev. Biochem., 2002, 71:435-471.
Falagas et al., "Colistin: The revival of polymyxins for the management of multidrug-resistant gram-negative bacterial infections," Clin. Infect. Dis., 40, 1333-1341, 2005.

Fermindez-Carneado et al., "Highly Efficient, Nonpeptidic Oligoguanidinium Vectors that Selectively Internalize into Mitochondria," J. Am. Chem. Soc., 2005, 127:869-874.
Fillon et al., "Cell Penetrating Agents Based on a Polyproline Helix Scaffold," J. Am. Chem. Soc., 2005, 127:11798-11803.
Flavell, "Saporin Innumotoxins," Curr. Top Microbiol. Immunol., 1998, 234:57-61.
Frankel et al., "Cellular uptake of the tat protein from human immunodeficiency virus," Cell, 1988.
Frankel, A.D. and J.A.T. Young, "Hiv-1: Fifteen Proteins and an RNA," Annu. Rev. Biochem. 67: 1-25 (1998).
Fry et al., "Rapid Separation of Low Molecular Weight Solutes from Liposomes without Dilution," Anal. Biochem., 1978, 90, 809-815.
Fu et al., "Intracellular Delivery of Functional Proteins and Native drugs by Cell-Penetrating Poly (disulfide)," J. Am. Chem. Soc., 2015, 137, 12153-12160.
Fuchs et al., "Pathway for Polyarginine Entry into Mammalian Cells," Biochemistry, 43:2438-2444, 2004.
Futaki et al., "Translocation of Branched-Chain Arginine Peptides through Cell Membranes: Flexibility in the Spatial Disposition of Positive Charges in Membrane-Permeable Peptides," Biochemistry, 2002, 41:7925-7930.
Futaki, "Membrane-permeable arginine-rich peptides and the translocation mechanisms," Adv. Drug Deliv. Rev., 2005, 57:547-558.
Futaki, "Oligoarginine Vectors for Intracellular Delivery: Design and Cellular-Uptake Mechanisms," Biopolymers Pept. Sci., 2006, 84:241-249.
Gasparini et al., "Cellular Uptake of Substrate-Initiated Cell-Penetrating Poly (disulfide)s," J. A. Chem. Soc. 2014, 136, 6069-6074.
Gasparini et al., "Protein delivery with cell-penetrating poly(disulfide)s," Chemical Communications, 2015, 51, 17160-17162.
Giannotti et al., "pH-Responsive Polysaccharide-Based Polyelectrolyte Complexes As Nanocarriers for Lysosomal Delivery of Therapeutics Proteins," Biomacromolecules 2011, 12, 2524-2533.
Green et al., "Autonomous functional domains of chemically synthesized human immunodeficiency virus tat trans-activator protein," Cell, 1988, 55:1179-1188.
Greenwald, R.B. et al., "Drug Delivery Systems employing 1,4- or 1,6-Eliminations: Poly(ethylene glycol) Prodrugs of Amino-containing Compounds," J. Med. Chem. 42: 3657-3667 (1999).
Hamajima et al., "Intranasal administration of HIV-DNA vaccine formulated with a polymer, carboxymethylcellulose, augments mucosal antibody production and cell-mediated immune response," Clin Immunol Immunopathol. Aug. 1998;88(2):205-10.
Hamill et al., "Delivery of an active lysosomal enzyme using GNeosomes," J. Mater. Chem. B. 5794-5797 (2016).
Hitz et al., "Interaction of α-and β-Oligoarginine-Acids and Amides with Anionic Lipid Vesicles: A Mechanistic and Thermodynamic Study," Biochemistry, 2006, 45:5817-5829.
Ho et al., "Drug Delivery Trends in Clinical Trials and Translational Medicine: Growth in Biologic Molecule Development and Impact on Rheumatoid Arthritis, Crohn's Disease, and Colitis," J. Pharm. Sci., 2012, 101, 2668-2674.
Hyman et al., "15 Years of Cell-penetrating, Guanidinium-rich Molecular Transporters: Basic Science, Research Tool, and Clinical Applications," Proc. Natl. Acad. Sci. U. S. A., 2012, 109, 13225-13230.
Inoue et al., "Aggregation-Mediated Macromolecular Uptake by a Molecular Transporter," ACS Chem Biol. 2013, 8, 1383-1388.
International Preliminary Report on Patentability in International Application No. PCT/US2014/025382, dated Sep. 24, 2015, 6 pages.
International Preliminary Report on Patentability in International Application PCT/US2010/048968, dated Mar. 20, 2012, 7 pages.
International Search Report and Written Opinion in International Application No. PCT/US2014/025382, dated Oct. 23, 2014, 7 pages.
International Search Report and Written Opinion in International Application No. PCT/US2016/025730, dated Jun. 27, 2016.
International Search Report and Written Opinion in International Application PCT/US2010/048968, dated Jun. 28, 2011, 11 pages.

(56) References Cited

OTHER PUBLICATIONS

International Search Report and Written Opinion dated Jul. 20, 2005 for PCT/US04/29880, dated Jul. 20, 2005.
Iwasa et al., "Cellular Uptake and Subsequent Intracellular Trafficking of R8-Liposomes Introduced at Low Temperature," BBA-Biomembranes 2006, 1758, 713-720.
Jean et al., "Molecular Vehicles for Mitochondrial Chemical Biology and Drug Delivery," ACS Chem. Biol. 2014, 9, 323-333.
Jeong, L.S. et al., "Nucleosides and Derivative," Chapter 2 in "Anti-AIDS Drug Development: Challenges, Strategies and Prospects," P. Mohan and M. Baba (Editors), Harwood Academic Publishers GmbH, Switzerland, 1995, pp. 39-63.
Joint United Nations Programme on HIV/AIDS (UNAIDS), Report on the Global HIV/AIDS Epidemic 2002, Switzerland, UNAIDS/02.26E, ISBN 92-1973-185-4, 229 pages (Jul. 2002).
Kadar et al, "The Renaissance of Polymyxins," Curr. Med. Chem., 2013, 20, 3759-3773.
Kakkis, "Enzyme replacement therapy for the mucopolysaccharide storage disorder," Expert Opin. Investig Drugs, 2002, 11(5):675-685.
Kaplan et al., "Cationic TAT peptide transduction domain enters cells by macropinocytosis," J. Controlled Release, 2005, 102:247-253.
Kirk et al., "Neomycin-Acridine Conjugate: A Potent Inhibitor of Rev-RRE Binding," J. Am. Chem. Soc., 2000, 122:980-981.
Kirkegaard, "Expert Opinion on Orphan Drugs," 2013, 1(5):385-404.
Klein et al., "New chemical tools for investigating human mitotic kinesin Eg5," Bioorg. Med. Chem. 2007, 15:6474-6488.
Kojima et al., "Rational Design and Development of Near-Infrared-Emitting Firefly Available in vivo," Angew. Chem. Int. Ed. 2013, 52, 1175-1179.
Koshkaryev et al., "Targeting of Lysosomes by Liposomes Modified with Octadecyl-Rhodamine B," J. Drug Target 2011, 19, 606-614.
Koshkaryev et al., "Increased apoptosis in Cancer Calls In Vitro and In Vivo by Ceramides in Transferrin-Modified Liposomes," Cancer Biol Ther. 2012, 13, 50-59.
Lamaze et al., "The emergence of clathrin-independent pinocytic pathways," Curr. Opin. Cell Biol., 1995, 7:573-580.
Li et al., "A review on phospholipids and their main applications in drug delivery systems," Asian Journal of Pharmaceutical Sciences, 2015, 10:81-98.
Lidholt et al., "A single mutation affects both N-acetylglucosaminyltransferase and glucuronosyltransferase activities in a Chinese hamster ovary cell mutant defective in heparin sulfate biosynthesis," Proc. Natl. Acad. Sci. U.S.A., 1992, 89:2267-2271.
Luedtke et al., "Guanidinoglycosides: A Novel Family of RNA Ligands," J. Am. Chem. Soc., 2000, 122:12035-12036.
Luedtke, N. W.; Carmichael, P.; Tor, Y., "Cellular Uptake of Aminoglycosides, Guanidinoglycosides, and poly-Arginine," J. Am. Chem. Soc. 2003, 125, 12374-12375.
Luedtke, N.W. and Y. Tor, "A Novel Solid-Phase Assembly for Identifying Potent and Selective RNA Ligands," Angew. Chem. Int. Ed. 39(10): 1788-1790 (2000).
Luzio et al., "Lysosomes: Fusion and Function," Nat. Rev. Mol. Cell. Bio. 2007, 8, 622-632.
Luzio et al., "Membrane dynamics and the biogenesis of lysosomes (Review)," Mol Membrane Biol., Apr.-Jun. 2003, 20:141-154.
M. Vaara, "Agents that increase the permeability of the outer membrane," Microbiol. Rev., vol. 56, No. 3, pp. 395-411, Sep. 1992.
Mandl et al., "Synthesis of Mono Protected 1,10-Diaza-18-Crown-6," Synthetic Commun. 2004, 19:3573-2578.
Maniganda et al., "A Lysosome-targeted Drug Delivery System Based on Sorbitol Backbone Towards Efficient Cancer Therapy," Org. Biomol. Chem. 2014, 12, 6564-6569.
Marty et al., "Enhanced heparan sulfate proteoglycan-mediated uptake of cell-penetrating peptide-modified liposomes," Cell. Mol. Life Sci. 2004, 61, 1785-1794.

Mayer et al., "Design and Synthesis of a Tag-Free Chemical Probe for Photoaffinity Labeling," Eur. J. Org. Chem., 2007, 28:4711-4720.
Meerovich et al., "Screening and Optimization of Ligand Conjugates for Lysosomal Targeting," Bioconjugate Chem. 2011, 22, 2271-2282.
Mevel et al., "Paromomycin and Neomycin B Derived Cationic Lipids: Synthesis and Transfection Studies," J. Control. Release 2012, 158, 461-469.
Michael et al., "Enhanced RNA binding of dimerized aminoglycosides," Bioorg. Med. Chem., 1999, 7:1361-1371.
Mitchell et al., "Polyarginine Enters Cells More Efficiently than Other Polycationic Homopolymeras," J. Papt. Res. 2000, 56, 318-325.
Muro et al., "Lysosomal Enzyme Delivery by ICAM-1-targeted Nanocarriers Bypassing Glycosylation- and Clathrin-dependent Endocytosis," Mol. Ther. 2006, 13, 135-141.
Nair et al., "Novel Lysosome Targets Molecular Transporter Built on a Guanidianium-poly-(propylene imine) Hybrid Dendron for Efficient Delivery of Doxorubicin into Cancer Cells," Chem Commun 2015, 51, 2403-2406.
Natarajan et al., "Construction of di-scFv through a Trivalent Alkyne-Azide 1,3-Dipolar Cycloaddition," Chem. Commun. 2007, 7, 695-697.
Nation et al., "Colistin in the 21st Century," Curr. Opin. Infect. Dis., 2009, 22, 535-543.
O'Dowd et al., "Preparation of tetra-Boc-protected polymyxin B nonapeptide," Tetrahedron Lett., 2007, 48, 2003-2005.
Oh et al., "Poly(L-aspartic acid) Nanogels for Lysosome-selective Antitumor Drug Delivery," Colloids Surf. B 2013, 101, 298-306.
Pavan et al., "Progress in Drug Delivery to the Central Nervous System by the Prodrug Approach," Molecules, May 1, 2008;13(5):1035-65.
Pollard, V.M. and M.H. Pollard, "The HIV-1 Rev Protein," Annu. Rev. Microbiol. 52: 491-532 (1998).
Pollock et al., "Uptake and Trafficking of Liposomes to the Endoplasmic Reticulum," FASEB J. 2010, 24, 1866-1878.
Prictovsek et al., "Solution Structure of Polymyxins B and E and Effect of Binding to Lipopolysaccharide: An NMR and Molecular Modeling Study," J. Med. Chem., 1999, 42, 4604-4613.
Rapraeger et al., "Requirement of heparan sulfate for bFGF-mediated fibroblast growth and myoblast differentiation," Science, 1991, 252:1705-1708.
Richard et al., "Cellular Uptake of Unconjugated TAT Peptide Involves Clathrin-dependent Endocytosis and Heparan Sulfate Receptors," J. Biol. Chem., 2005, 280:15300-15306.
Rothbard et al., "Adaptive translocation: the role of hydrogen bonding and membrane potential in the uptake of guanidinium-rich transporters into cells," Adv. Drug. Deliv. Rev., 2005, 57:495-504.
Rothbard et al., "Role of Membrane Potential and Hydrogen Bonding in the Mechanism of Translocation of Guanidinium-Rich Peptides into Cells," J. Am. Chem. Sci., 2004, 126:9506-9507.
Ryser, "Uptake of Protein by Mammalian Cells: An Underdeveloped Area: The penetration of foreign proteins into mammalian cells can be measured and their functions explored," Science, 1968, 159:390-396.
Sainlos et al., "Aminoglycoside-Derived Cationic Lipids for Gene Transfection: Synthesis of Kanamycin a Derivatives," Eur. J. Org. Chem. 2003, 15, 2764-2774.
Sainlos et al., "Kanamycin A-Derived Cationic Lipids as Vectors for Gene Transfection," ChemBioChem 2005, 6, 1023-1033.
Sakai et al., "Direct Observation of Anion-Mediated Translocation of Fluorescent Oligoarginine Carriers into and across Bulk Liquid and Anionic Bilayer Membranes," Chembiochem, 2005, 6:114-122.
Sarrazin et al., "Guanidinylated Neomycin Mediates Heparan Sulfate-Dependent Transport of Active Enzymes to Lysosomes," Mol. Ther. 2010, 18, 1268-1274.
Schwabacher et al., "Desymmetrization Reactions: Efficient Preparation of Unsymmetrically Substituted Linker Molecules," J. Org. Chem. 1998, 63:1727-1729.
Sidransky, E.; Lopez, G., "The Link Between the GBA Gene and Parkinsonism," Lancet Neurol. 2012, 11, 986-998.

(56) References Cited

OTHER PUBLICATIONS

Slingerlande et al., "Lipsomal Drug Formulations in Cancer Therapy: 15 Years Along the Road," Drug Discov. Today 2012, 17, 160-166.
Stewart, J. C. M., "Colorimetric Determination of Phospholipids with Ammonium Ferrothiocyanate," Anal. Biochem. 1980, 104, 10-14.
Storm et al., "Polymyxin and related peptide antibiotics," Anuu. Rev. Biochem., 1977, 46, 723-763.
Straubinger et al., "Endocytosis of Liposomes and Intracellular Fate of Encapsulated Molecules: Encounter with a Low pH Compartment after Internalization in Coated Vesicles," Cell 1983, 32, 1069-1079.
Thekkedath et al., "Lysosome-Targeted Octadecyl-Rhodamine B-Liposomes Enhance Lysosomal Accumulation of Glucocerebrosidase in Gaucher's Cells In Vitro," Nanomedicine 2013, 8, 1055-1065.
Torchilin et al., "TAT Peptide on the Surface of Liposomes Affords their Efficient Intracellular Delivery Even at Low Temperature and in the Presence of Metabolic Inhibitors," Proc. Natl. Acad. Sci. USA 2001, 98, 8786-8791.
Torchilin, V P "Cell Penetrating Peptide-Modified Pharmaceutical Nanocarriers for Intracellular Drug and Gene Delivery," J. Pept. Sci. 2008, 90, 604-610.
Trorchilin, V. P., "Recent Approaches to Intracellular Delivery of Drugs and DNA and Organelle Targeting," Annu. Rev. Biomed. Eng. 2006, 8, 343-375.
Turker et al., "Nasal route and drug delivery systems," Pharm. World Sci. Jun. 2004, 26(3). pp. 137-142.
Tyagi et al., "Internalization of HIV-1 Tat Requires Cells Surface Heparan Sulfate Proteoglycans," J. Biol. Chem. 2001, 276:3254-3261.
Umezawa et al., "Translocation of a β-Peptide Across Cell Membranes," J. Am. Chem. Soc., 2002, 124:368-369.
Wadia et al., "Transmembrane delivery of protein and peptide drugs by TAT-mediated transduction in the treatment of cancer," Adv. Drug Del. Rev., 2005, 57:579-596.
Wakselman, M., "1,4- and 1,6-eliminations from hydroxyl and amino-substituted benzyl systems: chemical and biochemical applications," Nouveau Journal De Chimie, 7(7): 439-447 (Jul. 1983).
Wang et al., "Electrostatic Interactions in RNA Aminoglycosides Binding," J. Am. Chem. Soc., 1997, 119:8734-8735.
Wang et al., "Synthesis of (S,R,R,R)-α,α'-Iminobis(methylene)bis(6-fluoro-3H, 4H-dihydro-2H-1-benzopyran-2-methanol)," Synthesis, 2007, 1154-1158.
Wang, H. and Y. Tor, "Dimeric Aminoglycosides: Design, Synthesis and RNA Binding," Bioorganic & Medicinal Chemistry Letters, 7(14): 1951-1956 (1997).
Wang, H. And Y. Tor, "Tobramycin-EDTA Conjugate: A Noninnocent Affinity-Cleaving Reagent," Bioorg. Med. Chem. Lett. (1998) 8: 3665-3670 (1998).
Wei et al., "Formation of HNK-1 Determinants and the Glycosaminoglycan Tetrasaccharide Linkage Region by UDP-GlcUA:Galactose β1, 3-Glucuronosyltransferases," J. Biol. Chem., 1999, 274:7857-7864.
Wender et al., "The design, synthesis, and evaluation of molecules that enable or enhance cellular uptake: Peptoid molecular transporters," Proc. Natl. Acad. Sci., 2000, 97:13003-13008.
Westbroek et al., "Exploring the Link Between Glucocerebrosidase Mutations and Parkinsonism," Trends Mol. Med. 2011, 17, 485-493.
Wexselblatt et al., "GNeosomes: Highly Lysosomotropic Nanoassemblies for Lysosomal Delivery," vol. 9 No. 4 3961-3968 (2015).
Williams et al., "Cell-surface heparan sulfate proteoglycans: dynamic molecules mediating ligand catabolism," Curr. Opin. Lipidol., 1997, 8:253-262.
Winchester et al., "The Molecular Basis of Lysosomal Storage Diseases and Their Treatment," Biochem Society Transactions, 2000, 28(2):150-154.
Wolf et al, "Lysosomal enzyme can bypass the blood-brain barrier and reach the CNS following intranasal administration," Mol Genet Metab. May 2012;106(1):131-4. doi: 10.1016/j.ymgme.2012.02.006. Epub Feb. 10, 2012.
Xu et al., "Demystifying Heparan Sulfate-Protein Interactions," Anuu. Rev. Biochem. 2014, 83, 129-157.
Yahav et al., "Colistin: new lessons on an old antibiotic," Clin. Microbiol. Infect., 18, pp. 18-29, 2011.
Yayon et al., "Cell surface, heparin-like molecules are required for binding of basic fibroblast growth factor to its high affinity receptor," Cell, 1991, 64:841-848.
Zhu et al., "Lysosomal Delivery of a Lipophilic Gemcitabine Prodrug Using Novel Acid-Sensitive Micelles Improved Its Antitumor Activity," Bioconjugate Chem. 2012, 23, 966-980.

* cited by examiner

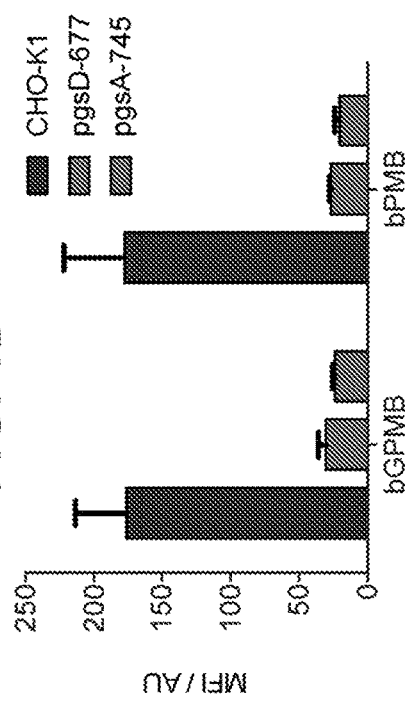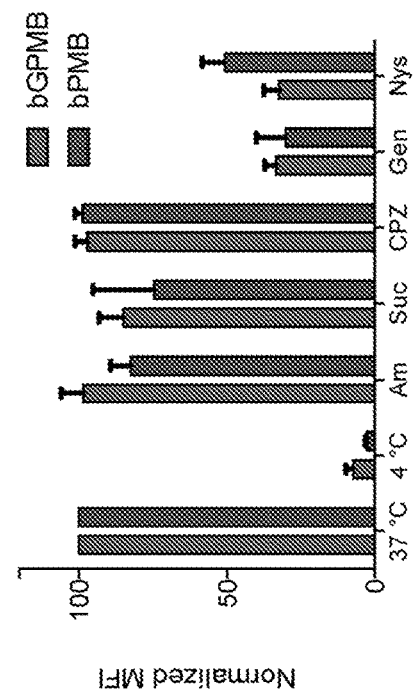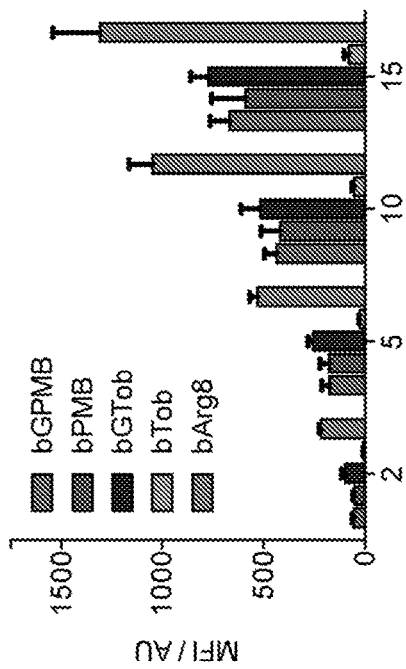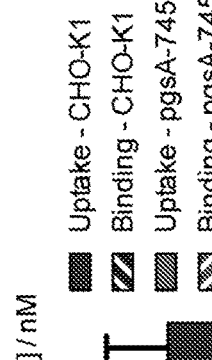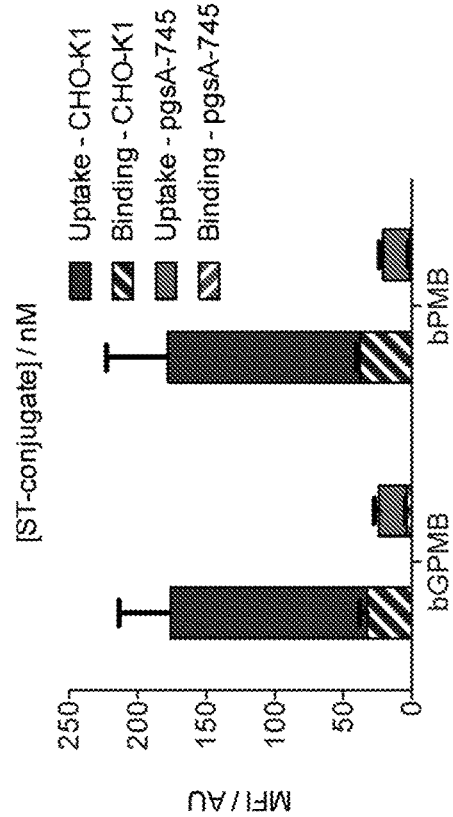

POLYMYXIN DERIVED CELL PENETRATING SCAFFOLDS

RELATED APPLICATIONS

This application claims priority to U.S. Provisional Application Ser. No. 62/405,066, filed on Oct. 6, 2016, which is incorporated by reference in its entirety herein.

FEDERALLY SPONSORED RESEARCH OR DEVELOPMENT

This invention was made with Government support under Grant No. GM077471, awarded by the National Institutes of Health, and Grant No. CHE-1303554, awarded by the National Science Foundation. The Government has certain rights in the invention.

TECHNICAL FIELD

The disclosure relates generally to transporters based on polymyxin B and polymyxin B derivatives, in particular guanidinylated derivatives of polymyxin B. Methods of using the transporters for intracellular delivery of cargo are also provided.

BACKGROUND

Polymyxin B is a cyclic polypeptide antibiotic containing five primary amines and an eight carbon fatty acid chain, used against Gram-negative bacteria (see, e.g., D. R. Storm, K. S. Rosenthal and P. E. Swanson, Annu. Rev. Biochem., 1977, 46, 723-763). Clinical use of polymyxin has diminished due to observed neurotoxicity and nephrotoxicity. Recently, however, with the increase in resistant gram-negative infections, the clinical use of polymyxins has been resurrected (see, e.g., M. E. Falagas and S. K. Kasiakou, Clin. Infect. Dis., 2005, 40, 1333-1341; B. Kadar, B. Kocsis, K. Nagy and D. Szabo, Curr. Med. Chem., 2013, 20, 3759-3773; D. Yahav, L. Farbman, L. Leibovici and M. Paul, Clin. Microbiol. Infect., 2012, 18, 18-29; R. L. Nation and J. Li, Curr. Opin. Infect. Dis., 2009, 22, 535-543).

Several biological barriers stand between exogenous agents and their entry to cells and tissues. These barriers hamper the administration of therapeutic agents, limiting their delivery and therapeutic utility. For example, high molecular weight and highly charged biomolecules such as proteins, liposomes, and oligonucleotides display therapeutic potential but have limited cellular uptake, limiting the delivery of these therapeutically active molecules to their intended targets. (see, e.g., R. J. Y. Ho and J. Y. Chien, J. Pharm. Sci., 2012, 101, 2668-2674). Thus, great interest exists in developing molecular transporters as tools for exploring cell entry pathways and for facilitating the delivery of impermeable agents.

SUMMARY

The present disclosure provides derivatives of polymyxin B (PMB) and guanidinylated polymyxin B (GPMB) that can effectively enter mammalian cells and can facilitate the transport and delivery of cargo, such as, e.g., large biomolecules and liposomal assemblies. High molecular weight and highly charged biomolecules such as proteins, liposomes and oligonucleotides display therapeutic potential but have limited cellular uptake, limiting the delivery of these therapeutically active molecules to their intended targets. The present disclosure provides methods of delivering cargo into mammalian cells and methods of enhancing the intracellular uptake of liposomes.

Provided herein is a compound of Formula (I)

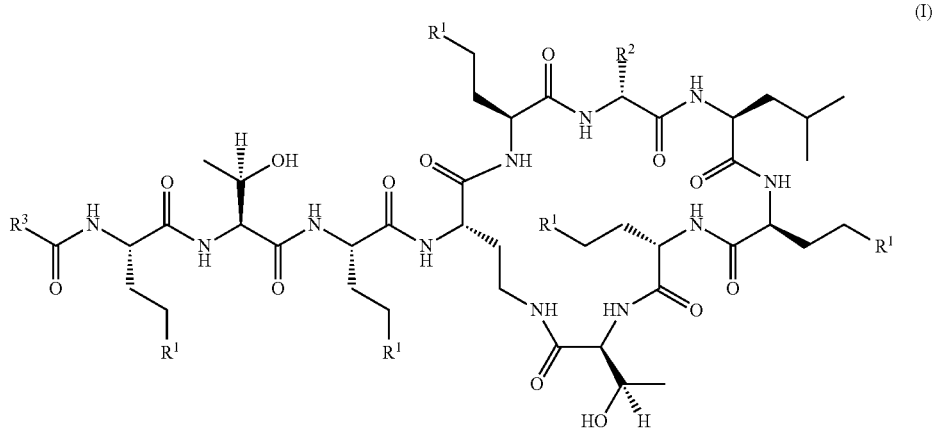

wherein each $R^1$ is independently selected from among an ammonium group ($-NH_3^+$) and a guanidinium group ($-NH-C(=NH_2^+)-NH_2$); $R^2$ is an amino acid side chain; and $R^3$ is a linker. In some embodiments, each $R^1$ is $-NH_3^+$. In some embodiments, each $R^1$ is $-NH-C(=NH_2^+)-NH_2$. In some embodiments, each $R^1$ is either $-NH_3^+$ or $-NH-C(=NH_2^+)-NH_2$. In some embodiments, $R^2$ is selected from among the group consisting of $-CH_3$, $-(CH_2)_3NHCHNH_2NH_2^+$, $-CH_2CONH_2$, $-CH_2COOH$, $-CH_2SH$, $-(CH_2)_2COOH$, $-(CH_2)_2CONH_2$, $-H$, $-CH_2$-imidazole, $-CH(CH_3)CH_2CH_3$, $-CH_2CH(CH_3)_2$, $-CH_2CH(CH_3)_2$, $-(CH_2)_4NH_3^+$, $-(CH_2)_2SCH_3$, $-CH_2$-phenyl, $-CH_2OH$, $-CH(OH)CH_3$, $-CH_2$-indole, $-CH_2$-phenyl-OH, and $-CH(CH_3)_2$. In some embodiments, $R^2$ is $-CH_2$-phenyl. In some embodiments, $R^3$ is selected from among an N-hydroxysuccinimide moiety, a polyethylene glycol moiety, a biotin moiety, one or more amino acids, a thiol moiety, an alkyl moiety, a heterocyclic moiety, a heteroaryl moiety, a polyether, a polyamine, a polyamide, a peptide, a carbohydrate, a lipid, a polyhydrocarbon, a polymeric compounds, and combinations thereof. In some embodiments, $R^3$ comprises a biotin moiety, a polyethylene glycol moiety, and a heteroaryl moiety In some embodiments, the compound of Formula (I) is conjugated to cargo. In some embodiments, the compound of Formula (I) is conjugated to the cargo through the linker. In some embodiments, the cargo has limited cellular uptake. In some embodiments, the cargo is selected from among a large biomolecule, a protein, an oligonucleotide, a drug, a liposome, a liposomal assembly, and combinations thereof. In some embodiments, the cargo has a molecular weight of greater than about 30, 50, 100, 200, 300, 500, or 1000 kDa. In some embodiments, the cargo has a molecular weight of greater than about 300 kDa.

In some embodiments, the compound of Formula (I) is a compound of formula (Ia)

In some embodiments, each $R^1$ is $-NH_3^+$. In some embodiments, each $R^1$ is $-NH-C(=NH_2^+)-NH^2$. In some embodiments, $R^2$ is selected from among the group consisting of $-CH_3$, $-(CH_2)_3NHCHNH_2NH_2^+$, $-CH_2CONH_2$, $-CH_2COOH$, $-CH_2SH$, $-(CH_2)_2COOH$, $-(CH_2)_2CONH_2$, $-H$, $-CH_2$-imidazole, $-CH(CH_3)CH_2CH_3$, $-CH_2CH(CH_3)_2$, $-CH_2CH(CH_3)_2$, $-(CH_2)_4NH_3^+$, $-(CH_2)_2SCH_3$, $-CH_2$-phenyl, $-CH_2OH$, $-CH(OH)CH_3$, $-CH_2$-indole, $-CH_2$-phenyl-OH, and $-CH(CH_3)_2$. In some embodiments, $R^2$ is $-CH_2$-phenyl. In some embodiments, $R^3$ is selected from among an N-hydroxysuccinimide moiety, a polyethylene glycol moiety, a biotin moiety, one or more amino acids, a thiol moiety, an alkyl moiety, a heterocyclic moiety, a heteroaryl moiety, a (Ia)

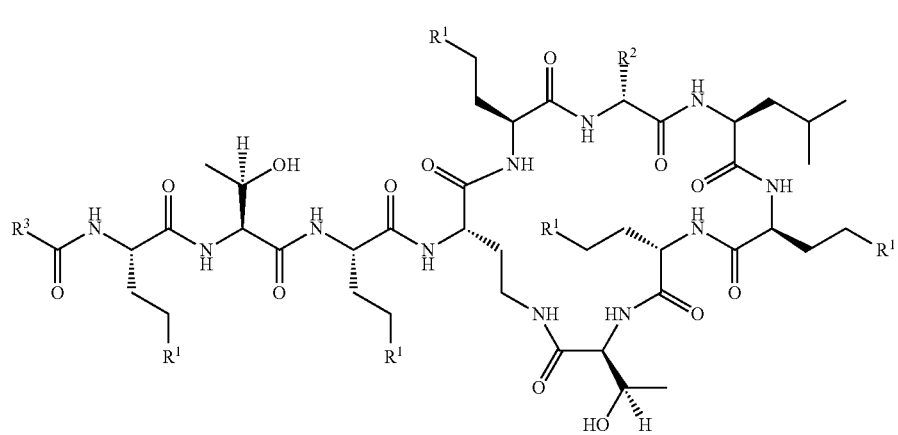

wherein each $R^1$ is selected from an ammonium group and a guanidinium group.

Provided herein is a method of delivering cargo into mammalian cells, comprising: a) coupling the cargo with a compound of Formula (I)

polyether, a polyamine, a polyamide, a peptide, a carbohydrate, a lipid, a polyhydrocarbon, a polymeric compounds, and combinations thereof. In some embodiments, $R^3$ comprises a biotin moiety, a polyethylene glycol moiety, and a heteroaryl moiety.

(I)

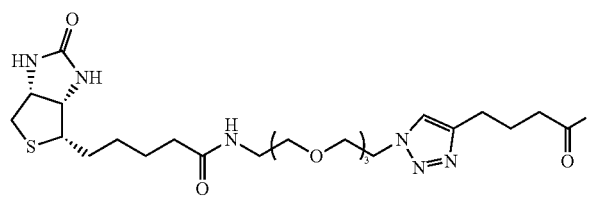

to form a conjugate, wherein each $R^1$ is independently selected from among an ammonium group ($-NH_3^+$) and a guanidinium group ($-NH-C(=NH_2^+)-NH_2$); $R^2$ is an amino acid side chain; and $R^3$ is a linker; and b) contacting the cells with the conjugate.

In some embodiments of the method, the cargo has limited cellular uptake. In some embodiments, the cargo is selected from among a large biomolecule, a protein, an oligonucleotide, a drug, a liposome, a liposomal assembly, and combinations thereof. In some embodiments, the cargo has a molecular weight of greater than about 30, 50, 100, 200, 300, 500, or 1000 kDa. In some embodiments, the cargo has a molecular weight of greater than about 300 kDa.

In some embodiments, the compound of Formula (I) is present at nanomolar concentrations.

In some embodiments of the method, following step b), the conjugate is internalized by the cells. In some embodiments, internalization depends on cell surface heparan sulfate. In some embodiments, internalization occurs through caveolae-mediated pathways.

Provided here is a method of enhancing the intracellular uptake of liposomes, comprising: a) incorporating into a liposome or liposomal assembly a compound of Formula (I)

(MFI) was measured by flow cytometry. The background signal from untreated cells was subtracted. FIG. 1A shows cellular uptake of biotinylated guanidinopolymyxin (bGPMB), polymyxin (bPMB), guanidinotobramycin (bGTob), tobramycin (bTob), and octarginine (bArg8) conjugated to ST-PE-Cy5. FIG. 1B shows cellular uptake of bGPMB and bPMB streptavidin-PE-Cy5 conjugates. FIG. 1C shows cellular uptake of bGPMB and bPMB streptavidin-PE-Cy5 conjugates. FIG. 1D shows cellular uptake of bGPMB and bPMB conjugated to streptavidin-PE-Cy5.

FIG. 2 shows the cellular uptake of GPMB and PMB conjugated to ST-PE-Cy5 in CHO-K1, HEK-293, and HEP-3B cells.

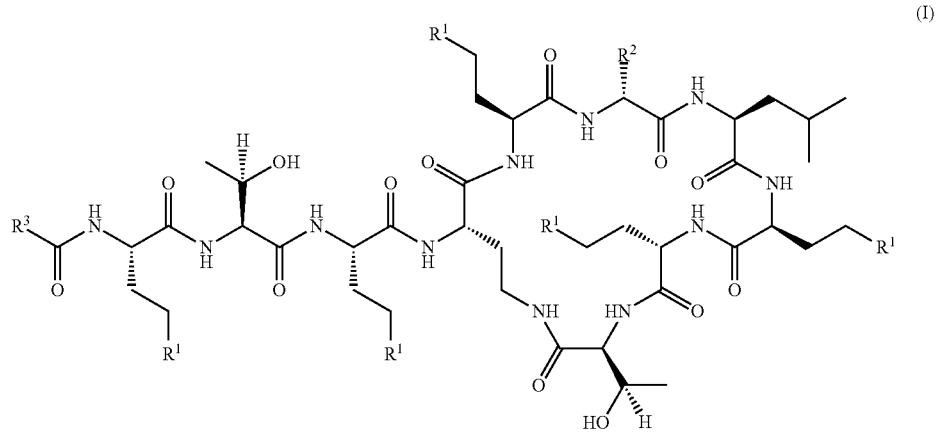

(I)

wherein each $R^1$ is independently selected from among an ammonium group ($-NH_3^+$) and a guanidinium group ($-NH-C(=NH_2^+)-NH_2$); $R^2$ is an amino acid side chain; and $R^3$ is a linker; and b) contacting mammalian cells with the liposome or liposomal assembly comprising the compound of Formula (I).

In some embodiments of the method, the liposome or liposomal assembly comprises cargo. In some embodiments, the cargo is selected from among a large biomolecule, a protein, an oligonucleotide, a drug, and combinations thereof. In some embodiments, the cargo has a molecular weight of greater than about 30, 50, 100, 200, 300, 500, or 1000 kDa. In some embodiments, the cargo has a molecular weight of greater than about 300 kDa.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1A-1D show the cellular uptake, binding, and effects of various inhibitors. Mean fluorescence intensity

FIG. 6B shows cells further treated with LysoTracker Green DND-26. FIG. 6C shows cells further treated with Hoechst 33342.

FIG. 9A shows transporter-saporin conjugates without streptavidin. FIG. 9B shows transporter-streptavidin-saporin conjugates.

DETAILED DESCRIPTION

Figure 2:
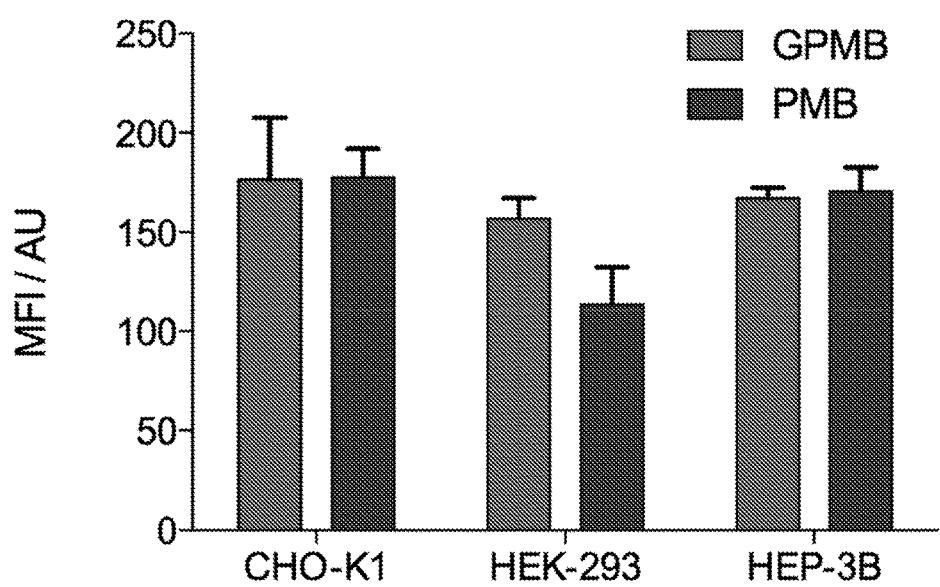

Provided herein are transporters based on the antibiotic polymyxin B. In some embodiments, transporters based on polymyxin B (PMB) and guanidinylated polymyxin B (GPMB) effectively enter mammalian cells and facilitate the delivery of cargo, such as, e.g., large biomolecules and liposomal assemblies.

In some embodiments, at nanomolar concentrations, the transporters provided herein can deliver large cargo into living cells. In some embodiments, the cargo has a molecular weight of greater than 300 kDa. Without being bound by any theory, it is believed that uptake of the transporters depends almost exclusively on cell surface heparan sulfate. Investigation of the uptake mechanism indicates these transporters are internalized through caveolae-mediated pathways and confocal microscopy has shown internalization in punctate vesicles that colocalize with the lysosomes. Thus, the transporters, e.g., polymyxin and guanidinopolymyxin derivatives, can be used for intracellular delivery of cargo, e.g., large biomolecules and liposomal assemblies, with potential as a basic research tool and novel drug delivery vehicle.

Transporters Based on Polymyxin B

In some embodiments, the transporters provided herein have the general Formula (I)

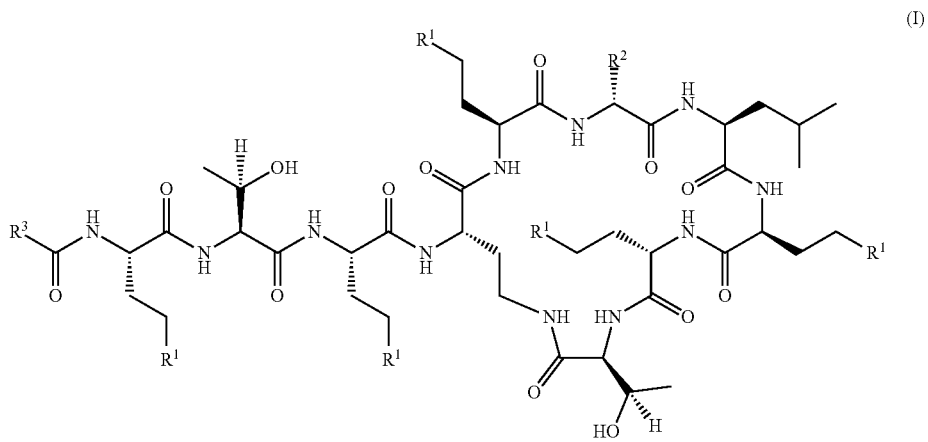

(I)

wherein each $R^1$ is independently selected from among an ammonium group (i.e., $-NH_3^+$) and a guanidinium group (i.e., $-NH-C(=NH_2^+)-NH_2$); $R^2$ is an amino acid side chain; and $R^3$ is a linker. In some embodiments, the compound of Formula (I) is further conjugated to cargo. In some embodiments, the cargo is coupled directly to the compound of Formula (I) via the $R^3$ linker. In some embodiments, $R^3$ is a combination of two or more linkers.

The terms "guanidinium group" or "guanidine moiety" as used herein refer to a moiety having the general structure:

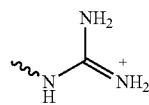

where the wavy line represents the point of attachment of the group to the rest of the molecule.

The term "guanidinylated" refers to a compound that has a guanidine moiety attached to it. For example, the term "guanidinylated polymyxin" refers to polymyxin B or a polymyxin B derivative having a guanidine moiety attached to it. For example, $R^1$ is a guanidinium group. In some embodiments, a guanidinylated polymyxin has one, two, three, four, or five guanidinium groups as $R^1$. In some embodiments, one, two, three, four, or five of the $R^1$ groups are guanidinium groups. In some embodiments, every $R^1$ group of the guanidinylated polymyxin is a guanidinium group. In some embodiments, all available positions are guanidinylated. The embodiments of the present disclosure include guanidinylated polymyxin B and polymyxin B derivatives as discussed herein. In some embodiments, these guanidinylated compounds are used as transporters for the uptake of compounds into mammalian cells.

In some embodiments, each $R^1$ is independently selected from among an ammonium group (i.e., $-NH_3^+$) and a guanidinium group (i.e., $-NH-C(=NH_2^+)-NH_2$). In some embodiments, each $R^1$ is an ammonium group (i.e., $-NH_3^+$). In some embodiments, each $R^1$ is a guanidinium group (i.e., $-NH-C(=NH_2^+)-NH_2$). In some embodiments, the transporter of Formula (I) includes both ammonium and guanidinium $R^1$ groups.

In some embodiments, $R^2$ is an amino acid side chain. The term "amino acid side chain" includes those groups found in: (i) naturally occurring amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine; (ii) minor amino acids such as ornithine and citrulline; and (iii) unnatural amino acids, beta-amino acids, synthetic analogs and derivatives of naturally occurring amino acids. In some embodiments, $R^2$ is selected from among an alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine side chain. In some embodiments, $R^2$ is a phenylalanine side chain.

In some embodiments, $R^2$ is an amino acid side chain selected from among $-CH_3$, $-(CH_2)_3NHCHNH_2NH_2^+$, $-CH_2CONH_2$, $-CH_2COOH$, $-CH_2SH$, $-(CH_2)_2COOH$, $-(CH_2)_2CONH_2$, $-H$, $-CH_2$-imidazole, $-CH(CH_3)CH_2CH_3$, $-CH_2CH(CH_3)_2$, $-CH_2CH(CH_3)_2$, $-(CH_2)_4$ $NH_3^+$, $-(CH_2)_2SCH_3$, $-CH_2$-phenyl, $-CH_2OH$, $-CH(OH)CH_3$, $-CH_2$-indole, $-CH_2$-phenyl-OH, and $-CH(CH_3)_2$. In some embodiments, $R^2$ is $-CH_2$-phenyl.

In some embodiments, $R^3$ is a linker. In some embodiments, $R^3$ is one or more linkers. The linker can be any physiologically compatible chemical group that does not interfere with the functions of the transporter or the cargo (e.g., an enzyme). In some embodiments, the linker is synthetically easy to incorporate into the transporter. In some embodiments, the linker is not so unduly large as to manifest an undesired biological function or targeting influence onto the transporter. In some embodiments, the linker has a functional group capable of reacting with another molecule, e.g., cargo. For example, in some embodiments, the linker serves to link together the compound of Formula (I) and the cargo.

In some embodiments, the length of the linker is between 1 and 50 angstroms, for example, between 1 and 10 angstroms. In some embodiments, the linker in selected from among an N-hydroxysuccinimide moiety, a polyethylene glycol moiety, a biotin moiety, one or more amino acids, a thiol moiety, an alkyl moiety, a heterocyclic moiety, including heteroaryl moieties, polyether, polyamine, polyamide, peptide, carbohydrate, lipid, polyhydrocarbon, other polymeric compounds (e.g., polyethylene glycols such as those having between 2 and 100 ethylene glycol units), and combinations thereof. In some embodiments, the linker is a biotin moiety. In some embodiments, the linker is a biotin moiety and a polyethylene glycol moiety. In some embodiments, the linker is a biotin moiety, a polyethylene glycol moiety, and a heteroaryl moiety. In some embodiments, the heteroaryl moiety is a triazole.

In some embodiments, the compound of Formula (I) is chemically conjugated to cargo. In some embodiments, the cargo is conjugated to the compound of Formula (I) via the $R^3$ linker. In some embodiments, the cargo is selected from among a large biomolecule, a protein, an enzyme, an oligonucleotide, a drug, a liposome, a liposomal assembly, and combinations thereof. In some embodiments, the cargo is a toxin. In some embodiments, the cargo is a ribosome-inactivating toxin. In some embodiments, the cargo is saporin. In some embodiments, the cargo is streptavidin. In some embodiments, the cargo is a dye. In some embodiments, the cargo is a protein. In some embodiments, the cargo is phycoerythrin.

In some embodiments, the compound of Formula (I) is incorporated into a liposome or liposome assembly. In some embodiments, the liposome or liposome assembly contains cargo. In some embodiments, the compound of Formula (I) is incorporated into a liposome or liposome assembly that contains cargo. In some embodiments, the compound of Formula (I) is chemically conjugated to cargo and is incorporated into a liposome or liposome assembly.

The compound of Formula (I) can be used to transport cargo of any size, including large cargo, into living cells. In some embodiments, the cargo has a molecular weight of greater than 30 kDa, such as 50, 100, 200, 300, 500, 1000 kDa or greater. In some embodiments, the cargo has a molecular weight of between about 50 and 60 kDa. In some embodiments, the cargo has a molecular weight of greater than 300 kDa.

In some embodiments, each $R^1$ is an ammonium group, $R^2$ is $-CH_2$-phenyl, and $R^3$ is a linker.

In some embodiments, each $R^1$ is a guanidinium group, $R^2$ is $-CH_2$-phenyl, and $R^3$ is a linker.

In some embodiments, each $R^1$ is an ammonium group, $R^2$ is $-CH_2$-phenyl, and $R^3$ includes biotin, a polyethylene glycol moiety, and a triazole. In some embodiments, the compound of Formula (I) is biotinylated polymyxin B (bPMB; compound 4a).

In some embodiments, each $R^1$ is a guanidinium group, $R^2$ is $-CH_2$-phenyl, and $R^3$ includes biotin, a polyethylene glycol moiety, and a triazole. In some embodiments, the compound of Formula (I) is biotinylated guanidinylated polymyxin B (bGPMB; compound 4b).

In some embodiments, the compound of Formula (I) is a compound of formula (Ia)

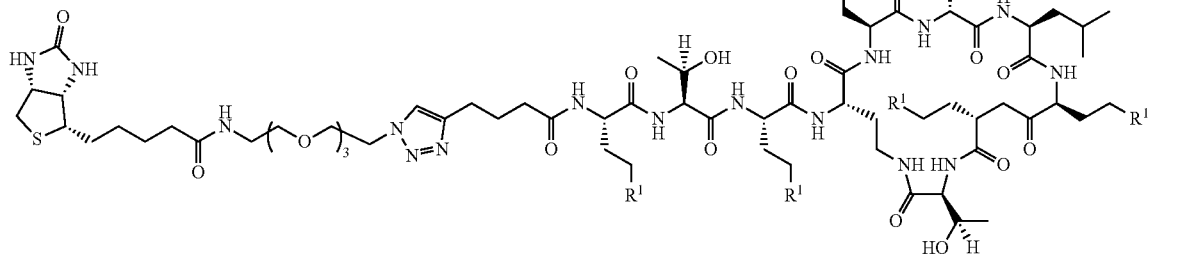

(Ia)

where each $R^1$ is independently selected from an ammonium group and a guanidinium group. In some embodiments, each $R^1$ is an ammonium group. In some embodiments, each $R^1$ is a guanidinium group. In some embodiments, the compound of formula (Ia) includes both ammonium groups and guanidinium groups.

While conversion of ammonium groups to guanidinium groups generally enhances cellular uptake rather dramatically, as seen with the conversion of aminoglycosides to guanidinoglycosides, the polymyxin B (PMB) and guanidinopolymyxin B (GPMB) transporters provided herein exhibit similar cellular uptake efficiencies. The cellular uptake of PMB and GPMB remains highly dependent on cell surface heparan sulfate and a fine mechanistic analysis suggests unique internalization pathways. In some embodiments, these transporters show more efficient cytosolic delivery than other well-studied molecular transporters. Additionally, the cyclic peptide, and not the hydrophobic tail, is the entry-facilitating module, which may help explain their adverse cytotoxic effects in mammals.

Certain natural macromolecules, for example the HIV-1 Tat protein, exhibit cellular uptake when added exogenously. Tat efficiently crosses cell membranes and can facilitate the uptake of conjugated or fused cargo. The basic, arginine rich region of the protein has been shown to be critical for uptake. Since these early observations, numerous guanidinium-rich molecular transporters of varying scaffolds have been described and used to deliver a variety of cargo into mammalian cells. The mechanism of cell entry, however, is not fully understood and likely involves multiple pathways and is cargo-dependent. A distinct non-oligomeric yet multivalent family of cellular carriers is the guanidine-glycosides, which are derived from the naturally occurring aminoglycosides in which the ammonium groups are converted to guanidinium groups. A variety of derivatives derived from different aminoglycosides enable uptake of large, bioactive cargo into the lysosomes of cells.

Guanidinium-rich molecular transporters of varying scaffolds have been prepared and used to deliver a variety of cargo into mammalian cells. In some embodiments, the guanidinium-rich scaffold is guanidinylated polymyxin B (GPMB). It is proposed that the positively-charged guanidinium group is able to form bidentate hydrogen bonds with negatively-charged cell surface components such as phosphates, carboxylates, and sulfates. Guanidino-glycosides, for example, show enhanced uptake compared to aminoglycosides and display unique uptake features when compared to other guanidinium-rich transporters by their activity at nanomolar concentrations and dependence on cell surface heparan sulfate proteoglycans for cellular entry.

Provided herein are high molecular weight biomolecules and nano-assemblies using polymyxin (PMB) and guanidinopolymyxin (GPMB) derivatives as carriers. Unlike the guanidinoglycosides that show substantially enhanced cellular uptake, when compared to their parent aminoglycoside precursors, both PMB and GPMB display highly competent uptake in mammalian cells. While the cellular uptake of PMB and GPMB remains highly dependent on cell surface heparan sulfate, a fine mechanistic analysis suggests unique internalization pathways and more efficient cytosolic delivery than other well-studied molecular transporters. Provided herein are polymyxin and its guanidinylated form that effectively enter mammalian cells. It is the cyclic peptide and not the hydrophobic tail that is the entry-facilitating module. In some embodiments, these molecules can facilitate the cellular delivery of large biomolecules and liposomal assemblies. In some embodiments, the effective entry of parent natural antibiotics into mammalian cells, coupled to earlier observations indicating their ability to interfere with eukaryotic translation, may contribute to their adverse cytotoxic effects in mammals. These observations, in addition to enriching the repertoire of cellular delivery vehicles, illustrate the wide landscape and potential utility of new ammonium and guanidinium rich transporters.

In some embodiments, the transporters provided herein, e.g., compounds of Formula (I), transport large biomolecules, such as proteins and oligonucleotides, and liposomal assemblies into cells. For illustrative purposes, Schemes 1-3 below show the synthesis of biotin derivatives of polymyxin (bPMB) and guanidinylated polymyxin (bGPMB) compounds of Formula (I). Enzymatic hydrolysis of the fatty acyl chain Dab1 portion of the commercially available PMB can generate the polymyxin B nonapeptide (PMBN). PMBN can be either boc-protected or boc-protected and guanidinylated before coupling to the biotin linker. The linker can be formed by a 1,3-dipolar cycloaddition of an alkyne portion and an azide-containing biotinylated linker. The enzymatically cleaved Dab residue will be reintroduced as part of the linker by amide bond formation to hexynoic acid so the final product will be similar to the natural PMB scaffold containing five Dab moieties (and the same number of primary amines). The transporter can then be conjugated to the fluorescently tagged protein streptavidin, which does not enter cells on its own.

Scheme 1.

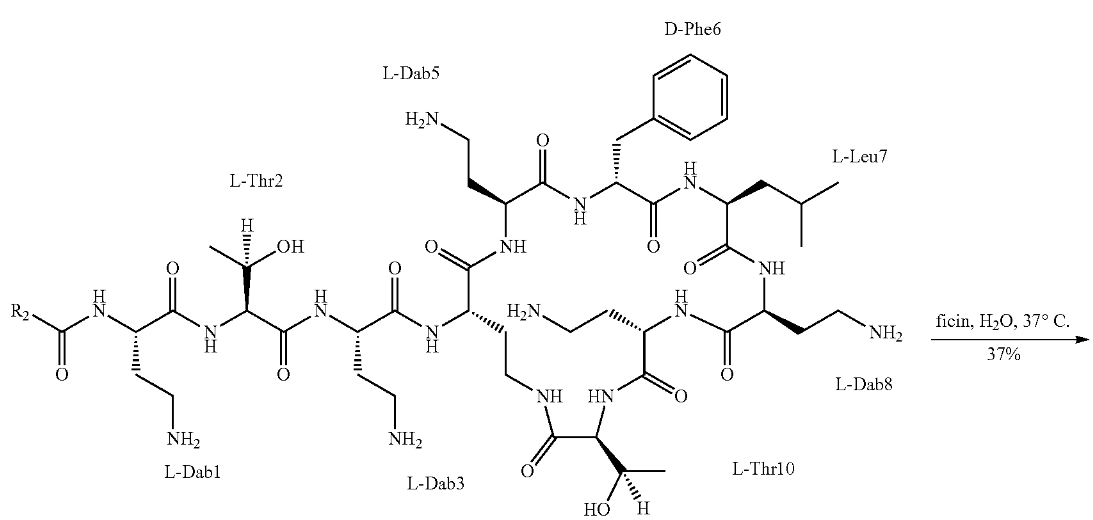

Polymyxin B (PMB)

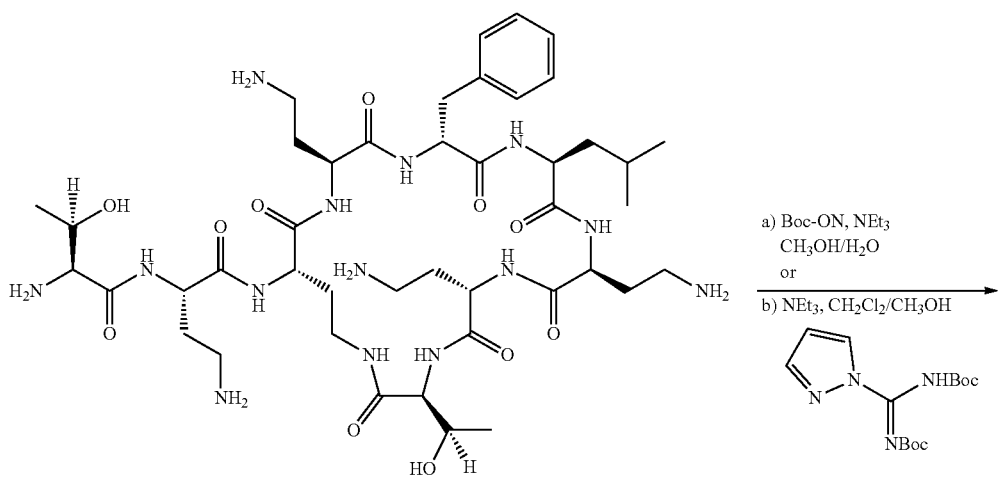
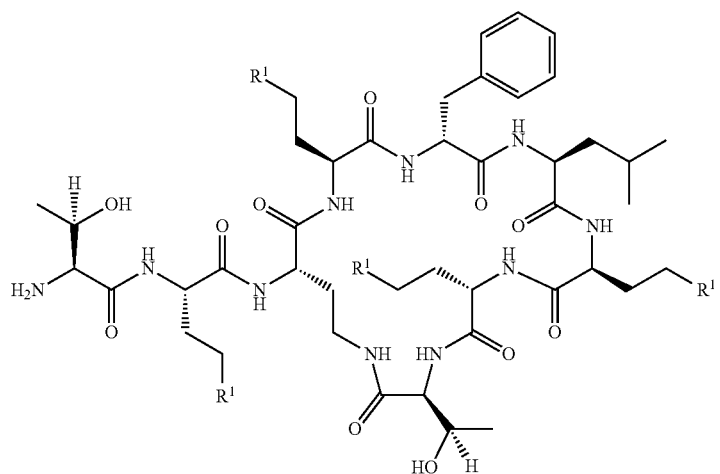
2a 69%
2b 53%
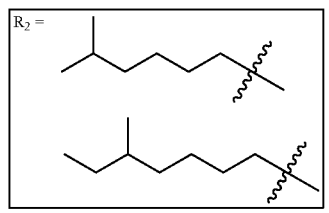
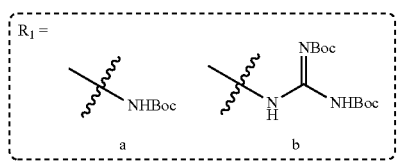

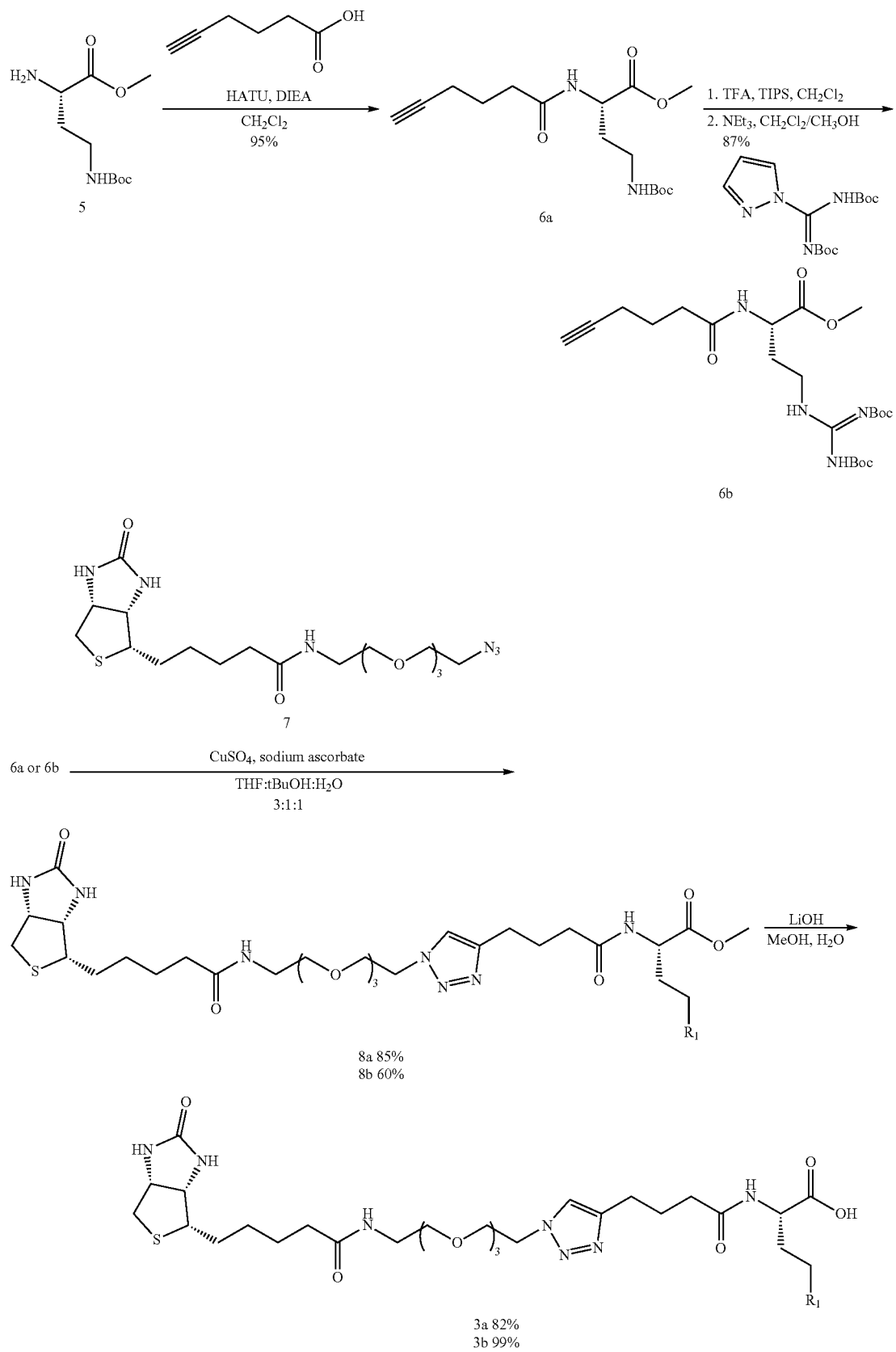

-continued
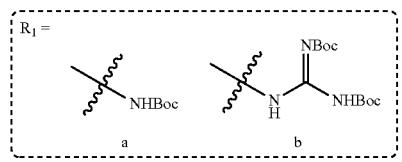
Scheme 3.
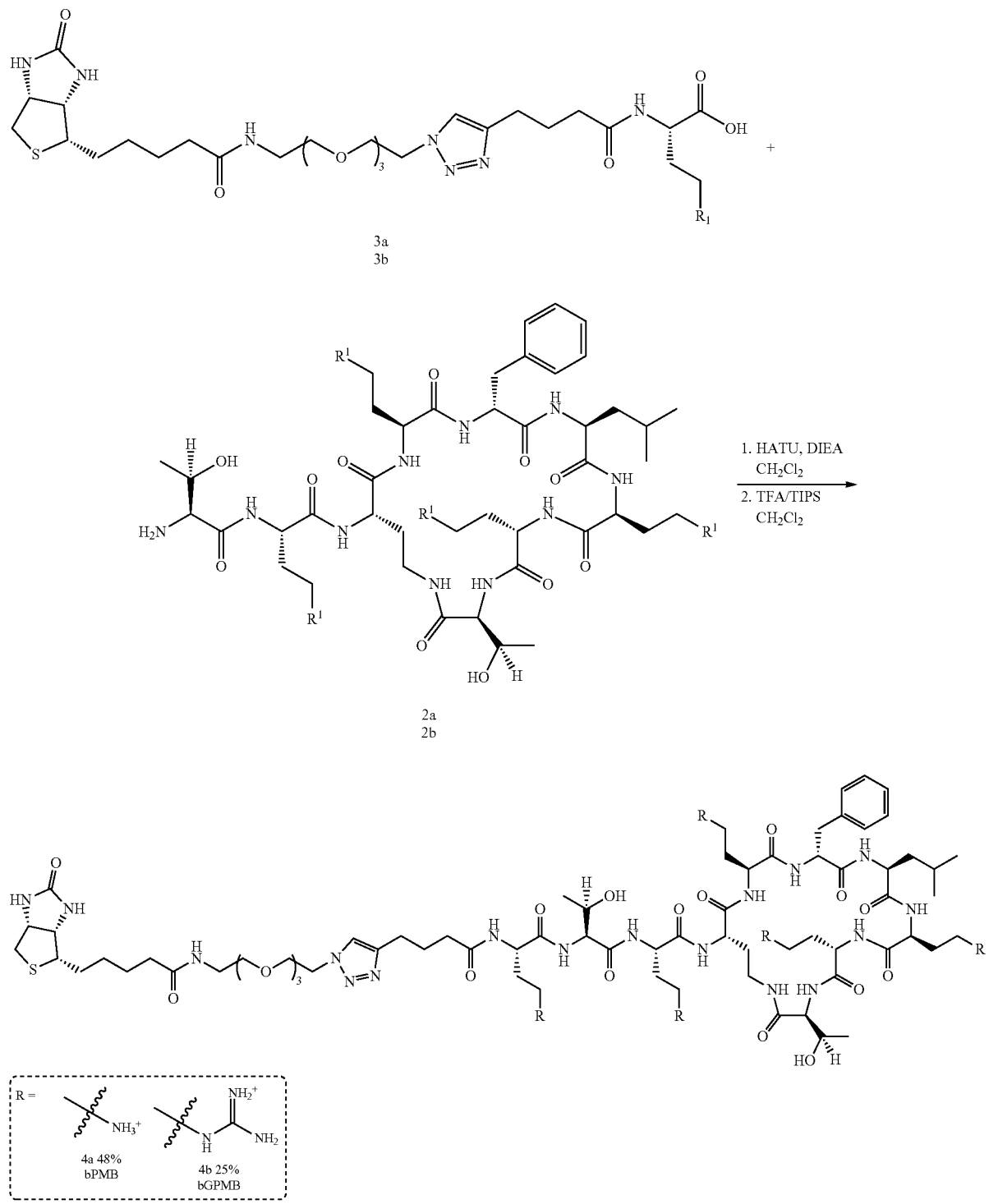

In some embodiments, PMB and its guanidinylated form GPMB are utilized to deliver cargo into mammalian cells. In some embodiments, the cargo is a protein. In some embodiments, the cargo is a toxin. In some embodiments, PMB and its guanidinylated form GPMB can be utilized in the delivery of liposomes into mammalian cells.

In some embodiments, provided are compounds of Formula (I) that are functionalized derivatives of the antibiotic polymyxin B and its guanidinylated derivative that facilitate uptake of the antibiotic into mammalian cells. In some embodiments, the compounds of Formula (I) can be used as molecular transporters. In some embodiments, at nanomolar concentrations, the compounds of Formula (I) are capable of delivering large cargo, e.g., large biomolecules, such as proteins and oligonucleotides, and liposomal assemblies, into living cells. In some embodiments, the liposomal assemblies contain cargo. In some embodiments, the compound of Formula (I) is compound 4a. In some embodiments, the compound of Formula (I) is compound 4b.

In some embodiments, the compound of Formula (I) can be incorporated into liposomes and enhance their intracellular uptake. In some embodiments, the natural polymyxin scaffold enhances intracellular uptake. In some embodiments, the liposomes contain cargo. In some embodiments, the compound of Formula (I) is chemically conjugated to cargo and is incorporated into a liposome or liposome assembly. In some embodiments, the compound of Formula (I) is incorporated into a liposome or liposome assembly that contains cargo.

Methods of Delivering Cargo

Provided herein are methods of delivering cargo into mammalian cells. In some embodiments, the method comprises coupling cargo with a compound of Formula (I) to form a conjugate, wherein each $R^1$ is independently selected from among an ammonium group (i.e., $-NH_3^+$) and a guanidinium group (i.e., $-NH-C(=NH_2^+)-NH_2$); $R^2$ is an amino acid side chain; and $R^3$ is a linker that is capable of conjugating the cargo; and contacting the cells with the conjugate. In some embodiments, the compound of Formula (I) is present at nanomolar concentrations.

In some embodiments, the conjugate (i.e., the compound of Formula (I) chemically conjugated to cargo) is internalized by the cells. In some embodiments, internalization depends on cell surface heparan sulfate. In some embodiments, internalization occurs through caveolae-mediated pathways.

In some embodiments, the cargo is selected from among a large biomolecule, a protein, an oligonucleotide, a drug, a liposome, a liposomal assembly, and combinations thereof. In some embodiments, the cargo has limited cellular uptake. In some embodiments, the cargo has a molecular weight of greater than about 30 kDa, such as about 50, 100, 200, 300, 500, 1000 kDa or greater. In some embodiments, the cargo has a molecular weight of between about 50 and 60 kDa. In some embodiments, the cargo has a molecular weight of greater than about 300 kDa. In some embodiments, the polymyxin-based transporters demonstrate cytosolic delivery through the delivery of a ribosome-inactivating toxin. In some embodiments, the polymyxin-based transporters demonstrate cytosolic delivery through the delivery of a protein. In some embodiments, the protein is a fluorescent protein.

Also provided herein are methods of enhancing the intracellular uptake of liposomes. In some embodiments, the method comprises incorporating into a liposome or liposomal assembly a compound of Formula (I)

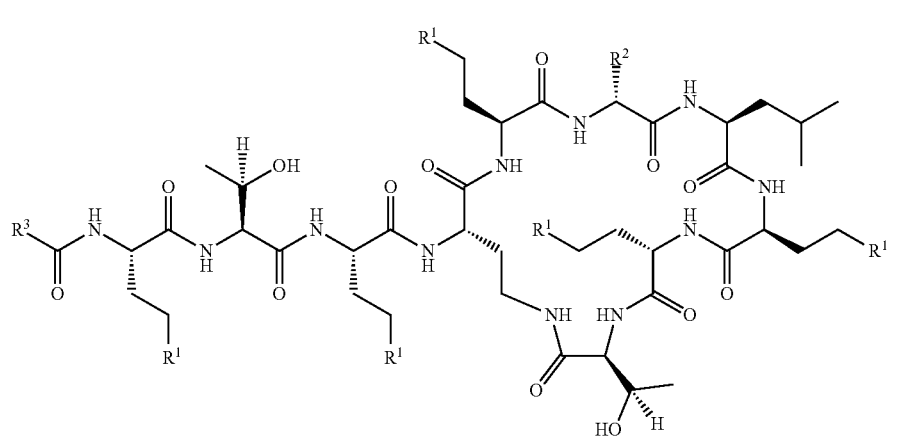

(I)

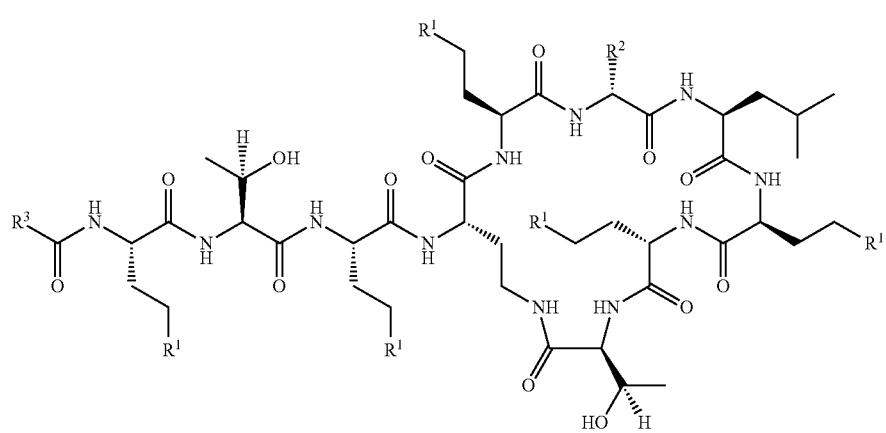

(I)

wherein each $R^1$ is independently selected from among an ammonium group (i.e., $-NH_3^+$) and a guanidinium group (i.e., $-NH-C(=NH_2^+)-NH_2$); $R^2$ is an amino acid side chain; and $R^3$ is a linker that is capable of conjugating the cargo; and contacting mammalian cells with the liposome or liposomal assembly comprising the compound of Formula (I).

In some embodiments, the compound of Formula (I) is incorporated into a liposome or liposome assembly that comprises cargo. In some embodiments, the compound of Formula (I) is chemically conjugated to cargo and is incorporated into a liposome or liposome assembly. In some embodiments, the cargo is selected from among a large biomolecule, a protein, an oligonucleotide, a drug, and combinations thereof. In some embodiments, the cargo has limited cellular uptake. In some embodiments, the cargo has a molecular weight of greater than about 30 kDa, such as about 50, 100, 200, 300, 500, 1000 kDa or greater. In some embodiments, the cargo has a molecular weight of between about 50 and 60 kDa. In some embodiments, the cargo has a molecular weight of greater than about 300 kDa.

EXAMPLES

The invention is further described in the following examples, which do not limit the scope of the invention described in the claims.

Example 1: Synthesis of Transporters

Materials

Materials obtained from commercial suppliers were used without further purification. Polymyxin B and tobramycin were purchased from TCI America. H-Dab(Boc)-OMe was purchased from Chem Impex International. Ficin was purchased from MP Biomedicals. Deuterated NMR solvents were purchased from Cambridge Isotope Laboratories. Amiloride, sucrose, and genistein were purchased from Sigma-Aldrich. Nystatin and EDTA/Trypsin were purchased from VWR and chlorpromazine was purchased from Fisher. Steptavidin-PE-Cy5 was purchased from Biolegend. PBS, F-12 media, Versene, streptavidin Cy-5, LysoTracker Green, and Hoescht dye were purchased from Life Technologies. Streptavidin saporin was purchased from Advanced Targeting Systems. 35 mm glass bottom culture dishes were purchased from MatTek. CellTiter-Blue was purchased from Promega. DOPC (1,2-dioleoyl-snglycero-3-phosphocholine), DOPE (1,2-dioleoylsn-glycero-3-phospho-ethanolamine), and cholesterol were purchased from Avanti Polar Lipids.

Instrumentation

NMR spectra were recorded on a Varian VX 500 MHz spectrometer or a Varian 400 MHz spectrometer. Mass spectra were recorded at UCSD Chemistry and Biochemistry Mass Spectrometry Facility utilizing an Agilent 6230 HR-ESI-TOF mass spectrometer. Reverse-phase HPLC purification (CLIPEUS, C18, 5 µm, 10×250 mm, Higgins analytical) and analysis (Eclipse, XDB-C18, 5 µm, 4.6×150 mm) were carried out on an Agilent 1200 series instrument or Beckman Coulter System Gold 127P Solvent Module. Flow cytometry studies were performed on a BD FACSCalibur. Confocal laser scanning microscopy was performed using a Nikon A1R inverted fluorescence microscope with z-stepping motor. Particle size, polydispersity, and surface charge of the lipid vesicles were measured by dynamic light scattering on a Zetasizer Nano ZS (model ZEN3600 from Malvern Instruments).

Synthesis of Boc-Protected PMBN and Boc-Protected Guanidinylated PMBN

Boc-protected PMBN and Boc-protected guanidinylated PMBN were synthesized according to the following synthetic scheme.

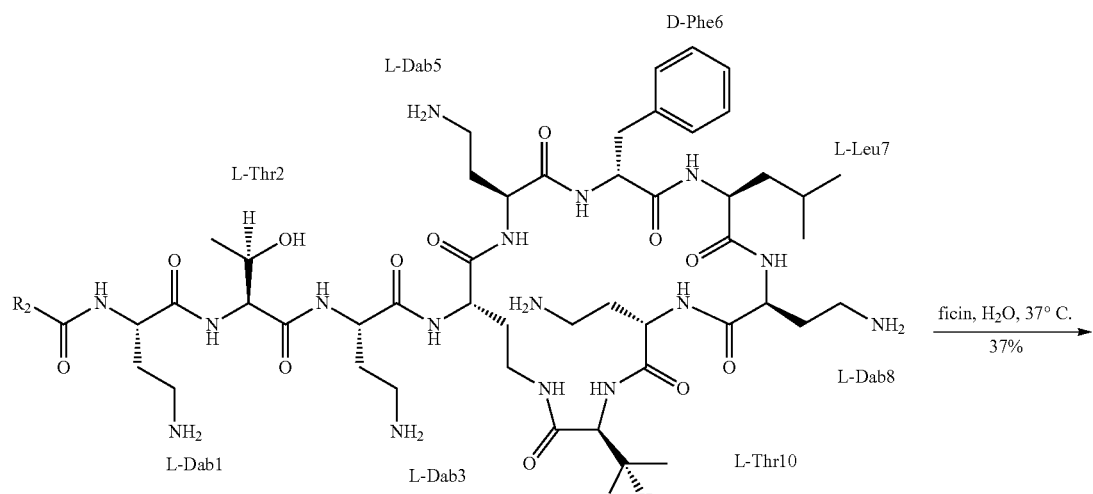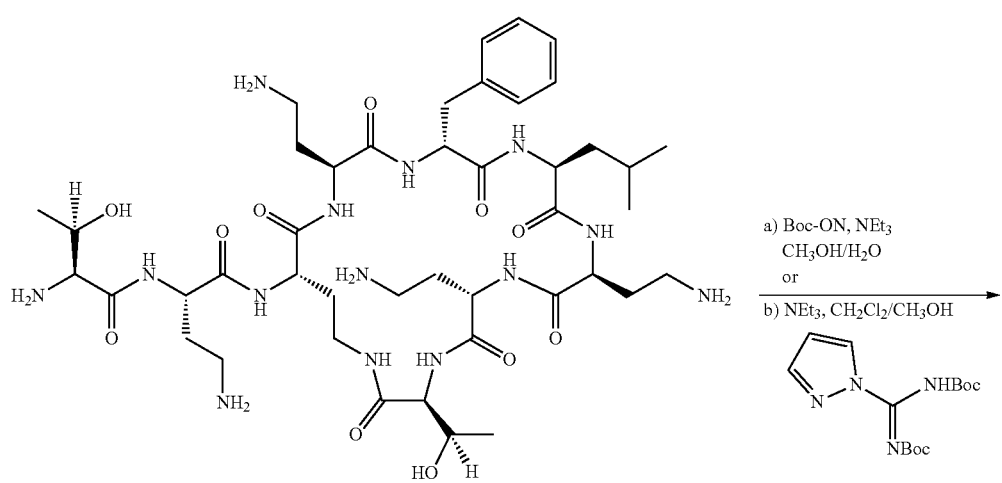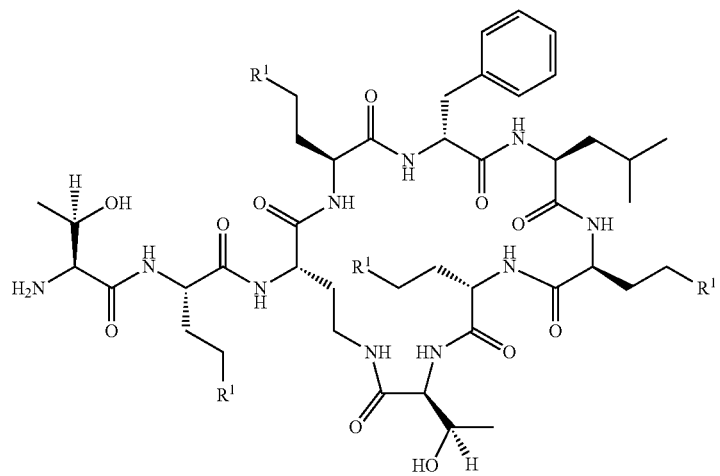

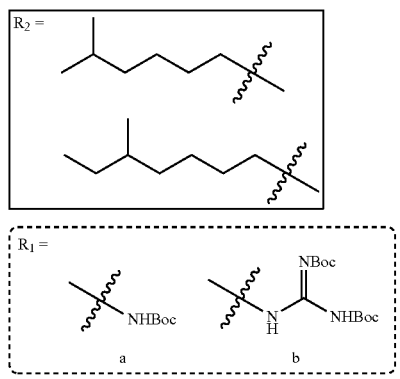

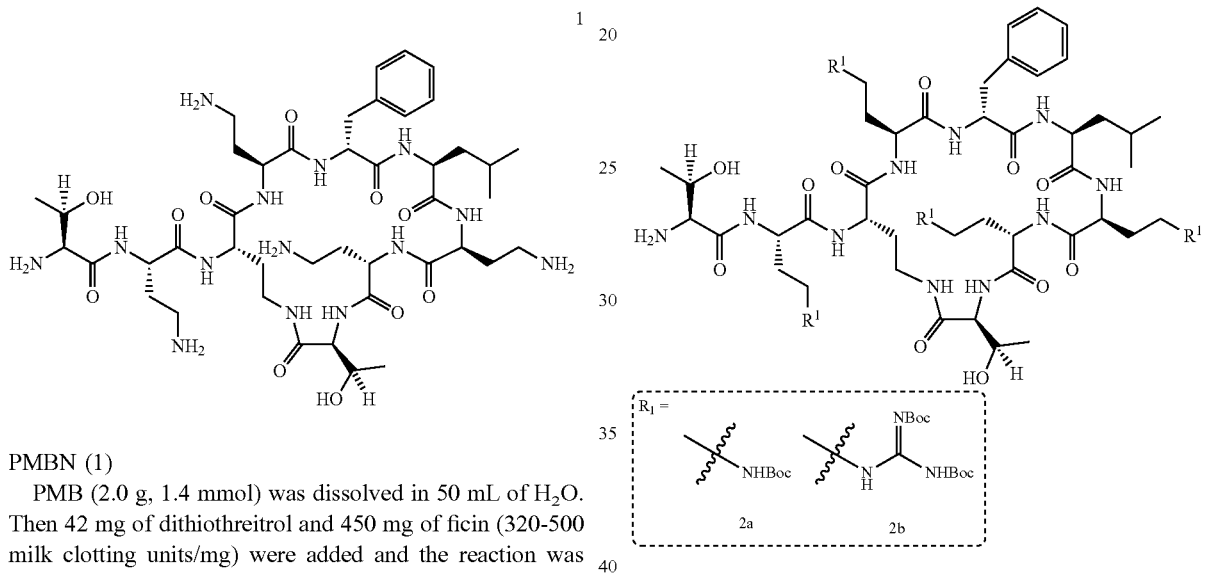

PMBN (1)

PMB (2.0 g, 1.4 mmol) was dissolved in 50 mL of H$_2$O. Then 42 mg of dithiothreitrol and 450 mg of ficin (320-500 milk clotting units/mg) were added and the reaction was heated to 37° C. and stirred overnight. When all PMB was consumed and only PMBN was detected by HPLC, the reaction was heated to reflux to denature the enzyme. After cooling, the precipitate was filtered off and the mother liqueur was evaporated under reduced pressure. The product was purified by automated flash chromatography (Teledyne Isco Redisep Rf C18 30 g gold column) using a gradient of 0-15% ACN (0.1% TFA) in H$_2$O (0.1% TFA), resulting in the TFA salt of 1 as a beige solid (1.5 g, 1.0 mmol, 72% yield).

$^1$H NMR (400 MHz, D$_2$O) δ 7.41-7.28 (m, 3H), 7.24 (d, J=7.6 Hz, 2H), 4.58-4.45 (m, 3H), 4.32-4.12 (m, 7H), 3.95 (d, J=5.5 Hz, 1H), 3.38-3.25 (m, 1H), 3.21-2.96 (m, 9H), 2.93-2.74 (m, 211), 2.29-1.77 (m, 10H), 1.50-1.23 (m, 511), 1.17 (d, J=6.3 Hz, 3H), 0.77-0.59 (m, 7H).

$^{13}$C NMR (126 MHz, D$_2$O) δ 174.99, 173.33, 173.30, 172.72, 172.68, 171.94, 171.59, 171.39, 168.13, 163.29, 163.01, 162.73, 162.44, 135.41, 128.93, 127.37, 119.73, 117.41, 115.09, 112.77, 66.18, 66.01, 59.44, 58.16, 55.76, 52.85, 51.84, 51.72, 51.67, 51.19, 50.38, 39.04, 36.78, 36.38, 36.33, 36.08, 35.85, 30.51, 29.65, 28.61, 28.13, 27.76, 23.37, 22.28, 20.21, 19.05, 18.49.

HR-ESI-MS calculated for C$_{43}$H$_{74}$N$_{14}$O$_{11}$ [M+H]$^+$ 963.5733, found 963.5734.

Compound 2a

In a 10 mL flask was added the TFA salt of PMBN (1, 104 mg, 0.0678 mmol), 2 mL MeOH, 1 mL H$_2$O, and NEt$_3$ (110 mg, 1.02 mmol, 140 µL). Then Boc-ON (67 mg, 0.27 mmol) was added and the reaction was stirred for 24 hours. The reaction was evaporated under reduced pressure and CH$_2$Cl$_2$ was added and washed with saturated NaHCO$_3$. The organic layer was dried over MgSO$_4$, filtered, and evaporated under reduced pressure. The product was isolated by automated flash chromatography (0-20% MeOH in CH$_2$Cl$_2$ over 18 mins) to afford the product 2a as a white solid (63.8 mg, 0.039 mmol, 69% yield).

$^1$H NMR (500 MHz, CD$_3$OD) δ 7.34-7.20 (m, 5H), 4.49-4.37 (m, 2H), 4.36-4.21 (m, 4H), 4.15-4.04 (m, 3H), 4.01 (d, J=3.7 Hz, 1H), 3.60-3.49 (m, 1H), 3.25-2.90 (m, 11H), 2.25-2.14 (m, 1H), 2.08-1.71 (m, 10H), 1.50-1.15 (m, 44H), 0.93-0.83 (m, 1H), 0.71 (s, 3H), 0.65 (s, 3H).

$^{13}$C NMR (126 MHz, CD$_3$OD) δ 175.41, 175.20, 174.17, 174.05, 173.74, 173.35, 172.71, 158.74, 158.39, 137.42, 130.40, 129.72, 128.06, 80.37, 80.14, 69.45, 67.28, 61.50, 61.09, 58.29, 54.82, 54.08, 52.91, 52.19, 52.07, 51.80, 40.49, 38.03, 37.79, 37.53, 36.75, 34.18, 33.24, 32.81, 32.28, 31.55, 30.81, 28.82, 28.40, 24.78, 23.80, 21.38, 20.82, 19.70.

HR-ESI-MS calculated for C$_{63}$H$_{106}$N$_{14}$O$_{19}$ [M+Na]$^+$ 1385.7651, found 1385.7640.

Compound 2b

In a 10 mL flask was added the TFA salt of PMBN (1, 112 mg, 0.0728 mmol), 2 mL MeOH, 2 mL $CH_2Cl_2$, and $NEt_3$ (110 mg, 1.09 mmol, 152 μL). Then N,N'-di-boc-1H-pyrazole-1-carboxamidine (88 mg, 0.284 mmol) was added and the reaction was stirred for 24 hours. The reaction was evaporated under reduced pressure and $CH_2Cl_2$ was added and washed with saturated $NaHCO_3$. The organic layer was dried over $MgSO_4$, filtered, and evaporated under reduced pressure. The product was isolated by automated flash chromatography (0-10% MeOH in $CH_2Cl_2$ over 22 mins) to afford the product 2b as a white solid (75 mg, 0.039 mmol, 53% yield).

$^1$H NMR (500 MHz, $CD_3OD$) δ 7.34-7.13 (m, 5H), 4.60-4.43 (m, 2H), 4.40 (t, J=8.1 Hz, 1H), 4.31-4.16 (m, 5H), 4.14-4.01 (m, 1H), 3.95 (d, J=4.8 Hz, 1H), 3.72-3.35 (m, 9H), 3.27-2.94 (m, 4H), 2.29-1.74 (m, 10H), 1.61-1.15 (m, 80H), 0.94-0.42 (m, 1H), 0.73 (dd, J=15.8, 5.8 Hz, 6H).

$^{13}$C NMR (126 MHz, $CD_3OD$) δ 175.02, 173.95, 173.65, 173.50, 172.52, 164.59, 164.47, 157.85, 157.62, 153.99, 153.90, 150.97, 137.71, 130.29, 129.69, 128.03, 84.42, 84.35, 84.28, 84.22, 80.45, 80.41, 69.52, 67.23, 61.94, 61.16, 58.18, 57.47, 54.12, 53.62, 52.82, 52.37, 52.29, 51.91, 40.45, 38.86, 38.61, 38.57, 37.82, 37.70, 36.79, 33.39, 32.90, 32.43, 32.35, 31.98, 31.13, 30.78, 30.75, 28.74, 28.71, 28.69, 28.65, 28.35, 25.00, 23.81, 21.52, 20.93, 19.78.

HR-ESI-MS calculated for $C_{87}H_{146}N_{22}O_{27}$ $[M+Na]^+$ 1954.0620, found 1954.0622.

Synthesis of Biotinylated Linker

A biotinylated linker was synthesized according to the following scheme.

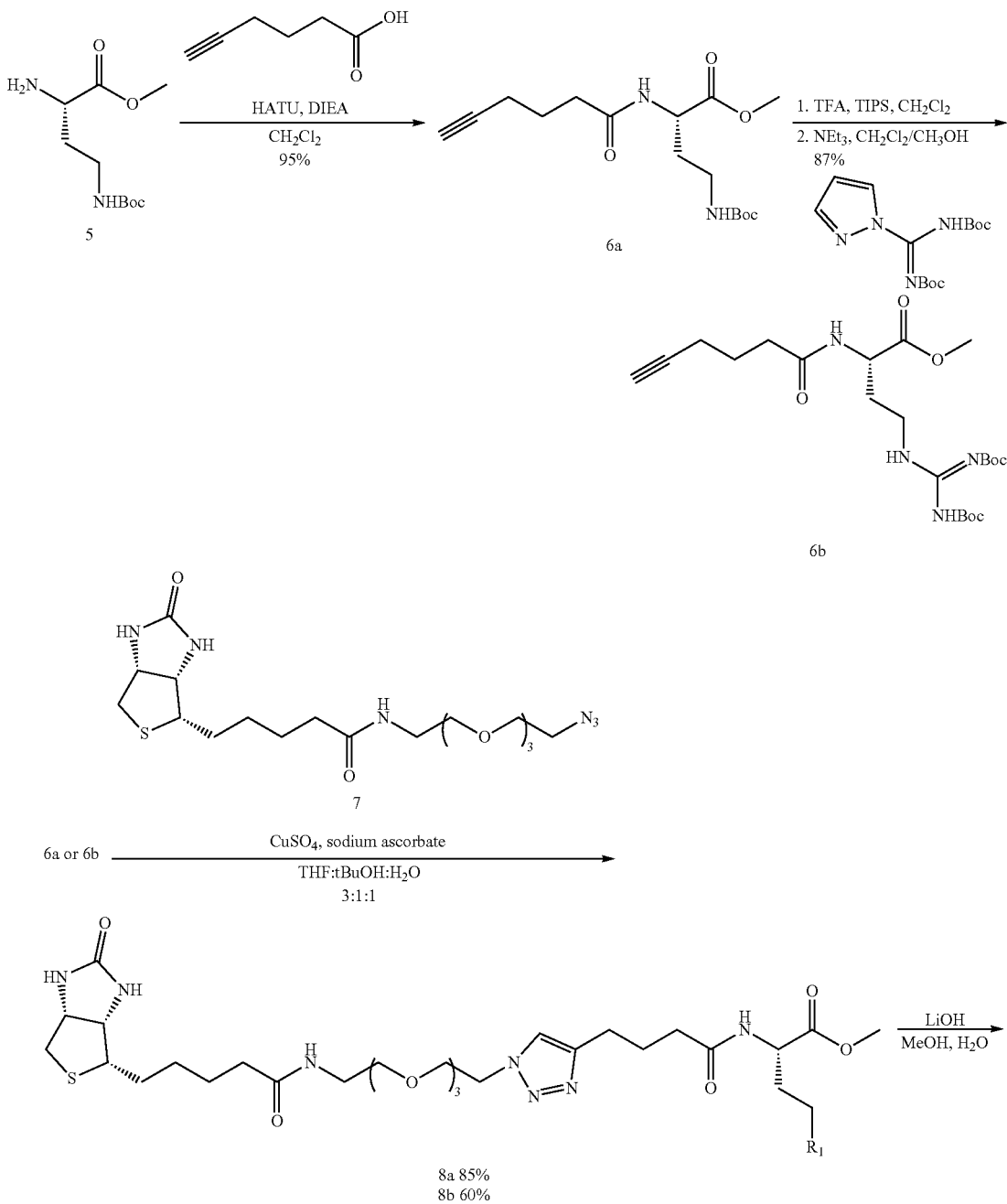

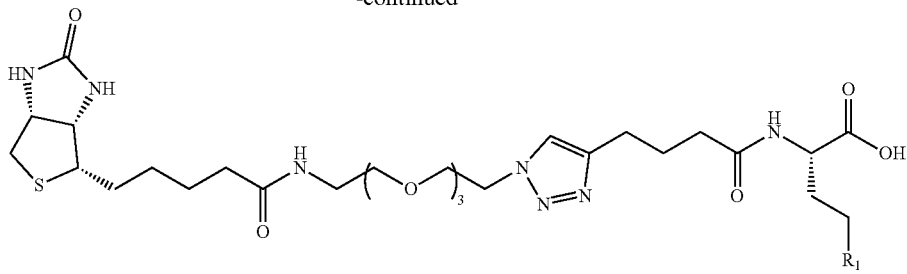

3a 82%
3b 99%

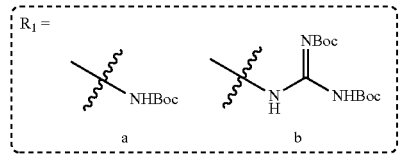

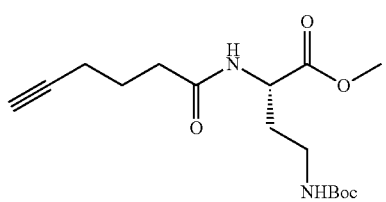

6a

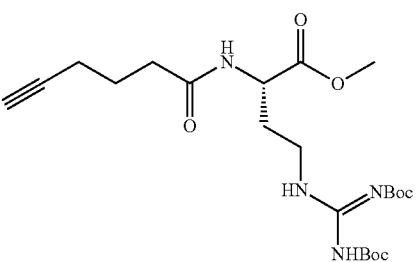

6b

Compound 6a 5-hexynoic acid (257 μL, 262 mg, 2.33 mmol), 1.1 mL of DIEA (804 mg, 6.22 mmol), and 8.6 mL DMF (filtered through silica), and HATU (887 mg, 2.33 mmol) were added to a 50 mL round bottom flask and allowed to stir for 10 min to give a yellow solution. Next, HDab(Boc)-OMe.HCl (418 mg, 1.56 mmol) was added and the reaction was stirred overnight. To the reaction was added $CH_2Cl_2$, which was washed with 2% citric acid and then sat. $NaHCO_3$. The organic layer was dried, filtered, and evaporated under reduced pressure. The product was isolated by automated flash chromatography (20-90% EtOAc in hexanes over 15 mins) to afford the product as a viscous oil (467 mg, 1.43 mmol, 92% yield).

$^1$H NMR (500 MHz, $CDCl_3$): δ 6.48 (d, J=7.4 Hz, 1NH), 5.19-5.13 (m, 1NH), 4.67 (td, J=8.5, 4.5 Hz, 1H), 3.48-3.34 (m, 1H), 3.00-2.85 (m, J=13.4, 9.2, 4.9 Hz, 1H), 2.40 (t, J=7.4 Hz, 2H), 2.26 (td, J=6.9, 2.6 Hz, 2H), 2.08-2.00 (m, 1H), 1.98 (t, J=2.7 Hz, 1H), 1.90-1.83 (m, 2H), 1.80-1.71 (m, 1H), 1.42 (s, 9H).

$^{13}$C NMR (126 MHz, $CDCl_3$) δ 173.05, 172.80, 156.23, 83.42, 79.56, 77.41, 77.16, 76.91, 69.45, 52.77, 49.67, 36.51, 34.96, 33.17, 28.52, 24.12, 17.92.

HR-ESI-MS calculated for $C_{16}H_{26}N_2O_5$ [M+Na]$^+$ 349.1734, found 349.1735.

Compound 6b

In a 25 mL flask was added BDabyne-OMe (6a, 212 mg, 0.629 mmol), $CH_2Cl_2$, triisopropylsilane (57 μL) and trifluoroacetic acid (1 mL). The solution was stirred for one hour and evaporated under reduced pressure. The residue was redissolved in $CH_2Cl_2$ (2 mL) and $NEt_3$ (1 mL). Then N,N'-di-boc-1H-pyrazole-1-carboxamidine (403 mg, 1.30 mmol) was added and the reaction was stirred overnight. The reaction was diluted with $CH_2Cl_2$ and washed with saturated $NaHCO_3$. The organic layer was dried over $MgSO_4$, filtered, and evaporated under reduced pressure. The product was isolated by automated flash chromatography (20-60% EtOAc in hexanes over 19 mins) to afford the product 6b as an oil.

$^1$H NMR (400 MHz, $CD_3OD$) δ4.49 (dd, J=8.5, 5.1 Hz, 1H), 3.71 (s, 3H), 3.54 (m, 1H), 3.38 (m, 1H), 2.41 (t, J=7.4 Hz, 2H), 2.28-2.21 (m, 3H), 2.12-1.95 (m, 2H), 1.83 (p, J=7.3 Hz, 2H), 1.53 (s, 9H), 1.49 (s, 9H).

$^{13}$C NMR (126 MHz, $CD_3OD$) δ 175.53, 173.71, 164.47, 157.75, 154.01, 84.49, 84.16, 80.50, 70.25, 52.84, 51.54, 38.22, 35.59, 31.73, 28.61, 28.23, 25.77, 18.60.

HR-ESI-MS calculated for $C_{22}H_{37}N_4O_7$[M+H]$^+$ 469.2657, found 469.2658.

8a

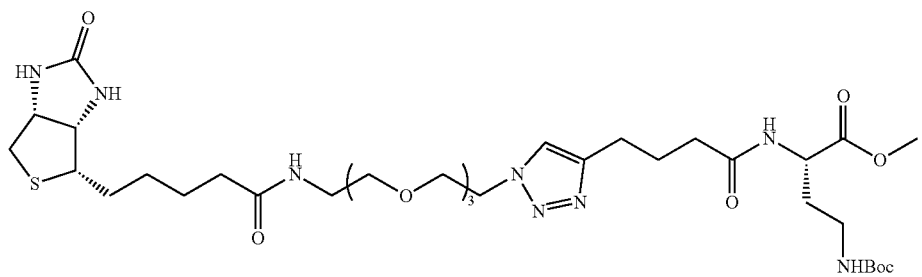

Compound 8a

BDabyneOMe (6a, 28.5 mg, 0.064 mmol) and Biotin-PEG-N$_3$ (7, 30.0 mg, 0.064 mmol) with a 1 mL 3:1:1 mixture of THF, t-BuOH, and H$_2$O were added to a 10 mL round bottom flask and purged with argon for 10 min. Next, 35 µL of a freshly prepared 1M of a sodium ascorbate and then a 28 µL of 7.5% solution of CuSO$_4$.5H$_2$O, both prepared in degassed water, were added. The reaction was stirred overnight. The reaction was evaporated under reduced pressure. The product was isolated by automated flash chromatography (2-17% MeOH in CH$_2$Cl$_2$ over 18 mins) to afford the product as a white solid (49.8 mg, 0.080 mmol, 85% yield).

$^1$H NMR (500 MHz, CDCl$_3$) δ 7.57 (s, 1H), 7.43 (d, J=7.9 Hz, 1NH), 6.94 (brs, 1NH), 6.27 (brd, J=22.5 Hz, 1NH), 5.40 (brd, J=23.1 Hz, 1NH), 5.24 (brs, 1NH), 4.62 (td, J=8.5, 4.5 Hz, 1H), 4.54-4.48 (m, 3H), 4.35-4.30 (m, 1H), 3.88 (t, J=5.1 Hz, 2H), 3.72 (s, 3H), 3.64-3.56 (m, 8H), 3.54 (t, J=5.1 Hz, 2H), 3.48-3.31 (m, 3H), 3.14 (td, J=7.3, 4.8 Hz, 1H), 3.00 (dt, J=13.5, 5.7 Hz, 1H), 2.90 (dd, J=12.8, 4.9 Hz, 1H), 2.77 (t, J=7.4 Hz, 2H), 2.73 (d, J=12.8 Hz, 1H), 2.33 (t, J=7.4 Hz, 2H), 2.24-2.13 (m, 2H), 2.08-1.96 (m, 4H), 1.86-1.57 (m, 5H), 1.42 (s, 10H).

$^{13}$C NMR (126 MHz, CDCl$_3$) δ73.65, 173.52, 173.50, 163.87, 156.21, 147.29, 122.54, 79.49, 70.61, 70.52, 70.49, 70.15, 70.06, 69.64, 61.96, 60.21, 55.73, 52.68, 50.22, 49.86, 40.70, 39.24, 36.78, 35.82, 35.36, 32.54, 28.56, 28.25, 28.17, 25.69, 25.49, 24.86.

HR-ESI-MS calculated for C$_{34}$H$_{58}$N$_8$O$_{10}$S [M+Na]$^+$ 793.3889, found 793.3885.

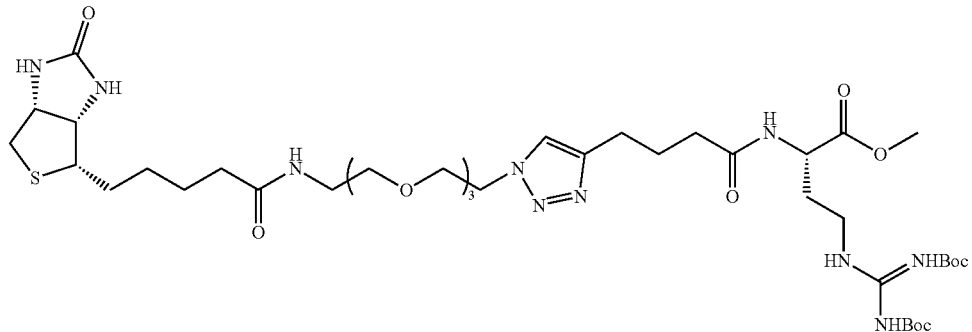

8b

Compound 8b

BGuanDabyneOMe (6b, 28.5 mg, 0.064 mmol) and Biotin-PEG-N$_3$ (30.0 mg, 0.064 mmol) with a 1 mL 3:1:1 mixture of THF, t-BuOH, and H$_2$O was added to a 10 mL round bottom flask and purged with argon for 10 min. Next, 35 µL of a freshly prepared 1M of a sodium ascorbate and then a 28 µL of 7.5% solution of CuSO$_4$.5H$_2$O, both prepared in degassed water, were added. The reaction was stirred overnight. The reaction was evaporated under reduced pressure. The product was isolated by automated flash chromatography (5-12% MeOH in CH$_2$Cl$_2$ over 19 mins) to afford the product as a white solid (49.8 mg, 0.080 mmol, 85% yield).

$^1$H NMR (500 MHz, CD$_3$OD): δ 7.85 (s, 1H), 4.55 (t, J=5.1 Hz, 2H), 4.52-4.47 (m, 2H), 4.31 (dd, J$_1$=8, 4.5 Hz, 1H), 3.89 (t, J=5 Hz, 2H), 3.72 (s, 3H), 3.61-3.52 (m, 11H), 3.39 (q, J=7 Hz, 1H), 3.35 (q, J=5.5 Hz, 2H), 3.22-3.18 (m, 1H), 2.93 (dd, J$_1$=12.5, 5 Hz, 1H), 2.75 (dd, J$_1$=8.5, 7.3 Hz, 2H), 2.70 (d, J=13 Hz, 1H), 2.37-2.34 (m, 2H), 2.21 (t, J=7.3 Hz, 2H), 2.10-2.05 (m, 1H), 2.03-1.96 (m, 3H), 1.77-1.39 (m, 26H);

$^{13}$C NMR (126 MHz, CD$_3$OD): δ 176.17, 176.08, 175.63, 173.75, 166.09, 164.47, 157.74, 153.99, 124.26, 84.49, 80.49, 71.56, 71.49, 71.43, 71.26, 70.57, 70.41, 63.35, 61.60, 57.03, 52.89, 51.54, 51.34, 41.08, 40.47, 40.34, 38.24, 36.77, 36.72, 35.99, 31.79, 29.78, 29.50, 28.61, 28.23, 26.87, 26.57, 25.68.

HR-ESI-MS calculated for C$_{40}$H$_{68}$N$_{10}$O$_{12}$S [M+H]$^+$ 913.4812, found 913.4811.

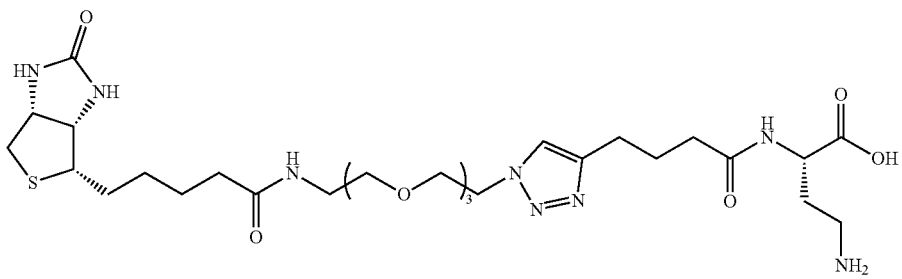

3a

Compound 3a

BDabOMeBiotin (8a, 27 mg, 0.035 mmol), 1.25 mL of MeOH, and 0.42 mL of 0.1 M LiOH solution in water (1 mg, 0.042 mmol) were added to a 10 mL round bottom flask and stirred overnight. The compound was desalted on a C-18 sep-pak (waters) to provide the product 3a as a white solid (22 mg, 0.029 mmol, 82% yield).

$^1$H NMR (500 MHz, CD$_3$OD) δ 7.87 (s, 1H), 4.57-4.53 (m, 2H), 4.49 (ddd, J=7.9, 4.9, 0.7 Hz, 1H), 4.33-4.27 (m, 2H), 3.91-3.87 (m, 2H), 3.63-3.56 (m, 10H), 3.53 (t, J=5.5 Hz, 2H), 3.35 (t, J=5.5 Hz, 2H), 3.19 (tt, J=3.6, 3.2 Hz, 2H), 3.06-2.98 (m, 1H), 2.92 (dd, J=12.7, 5.0 Hz, 1H), 2.75 (t, J=7.6 Hz, 2H), 2.70 (d, J=12.7 Hz, 1H), 2.32 (t, J=7.5 Hz, 2H), 2.21 (t, J=7.4 Hz, 2H), 2.07-1.94 (m, 4H), 1.78-1.54 (m, 6H), 1.45-1.40 (m, 11H).

$^{13}$C NMR (126 MHz, CD$_3$OD): δ 176.17, 176.08, 175.63, 173.75, 166.09, 164.47, 157.74, 153.99, 124.26, 84.49, 80.49, 71.56, 71.49, 71.43, 71.26, 70.57, 70.41, 63.35, 61.60, 57.03, 52.89, 51.54, 51.34, 41.08, 40.47, 40.34, 38.24, 36.77, 36.72, 35.99, 31.79, 29.78, 29.50, 28.61, 28.23, 26.87, 26.57, 25.68.

HR-ESI-MS calculated for C$_{33}$H$_{56}$N$_8$O$_{10}$S [M+Na]$^+$ 779.3737, found 779.3732.

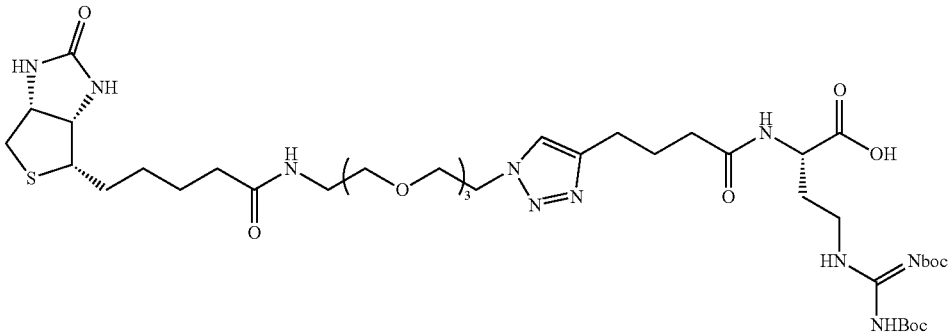

3b

Compound 3b

BGDabOMeBiotin (8b, 27 mg, 0.035 mmol), 1.25 mL of MeOH, and 0.42 mL of 0.1 M LiOH solution in water (1 mg, 0.042 mmol) were added to a 10 mL round bottom flask and stirred overnight. The compound was desalted on a C-18 sep-pak (waters) to provide the product 3b as a white solid (22 mg, 0.029 mmol, 82% yield).

$^1$H NMR (500 MHz, CD$_3$OD) δ 7.87 (s, 1H), 4.55 (t, J=5.0 Hz, 2H), 4.49 (dd, J=7.8, 4.8 Hz, 1H), 4.33-4.27 (m, 2H), 3.89 (t, J=5.1 Hz, 2H), 3.62-3.54 (m, 8H), 3.53 (t, J=5.5 Hz, 2H), 3.35 (t, J=5.4 Hz, 2H), 3.30-3.24 (m, 1H), 3.22-3.17 (m, 1H), 2.92 (dd, J=12.7, 5.0 Hz, 1H), 2.75 (t, J=7.6 Hz, 2H), 2.70 (d, J=12.7 Hz, 1H), 2.35 (t, J=7.3 Hz, 2H), 2.21 (t, J=7.4 Hz, 2H), 2.17-2.09 (m, 1H), 2.04-1.96 (m, 2H), 1.88-1.78 (m, 1H), 1.77-1.55 (m, 5H), 1.52 (s, 9H), 1.48-1.39 (m, 11H).

$^{13}$C NMR (126 MHz, CD$_3$OD) δ 178.59, 176.14, 174.91, 166.13, 158.21, 149.44, 148.27, 124.30, 79.84, 71.57, 71.50, 71.45, 71.27, 70.55, 70.42, 63.36, 61.61, 57.03, 53.91, 51.31, 41.07, 40.36, 38.43, 36.73, 36.36, 34.47, 29.78, 29.51, 28.80, 26.87, 26.71, 25.80.

HR-ESI-MS calculated for C$_{39}$H$_{66}$N$_{10}$O$_{12}$S [M+H]$^+$ 899.4655, found 899.4653.

Synthesis of Polymyxin and Guanidinopolymyxin Transporters

Polymyxin and guanidinopolymyxin transporters were synthesized according to the following scheme.

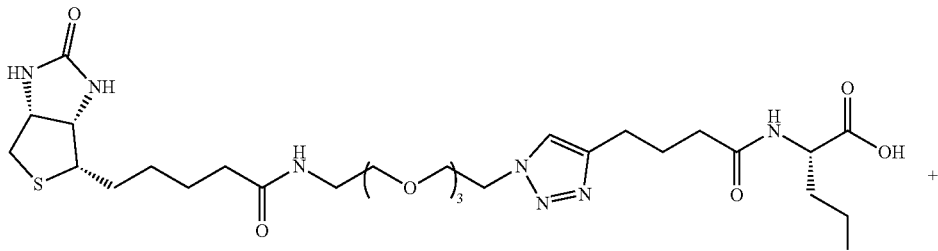

3a
3b

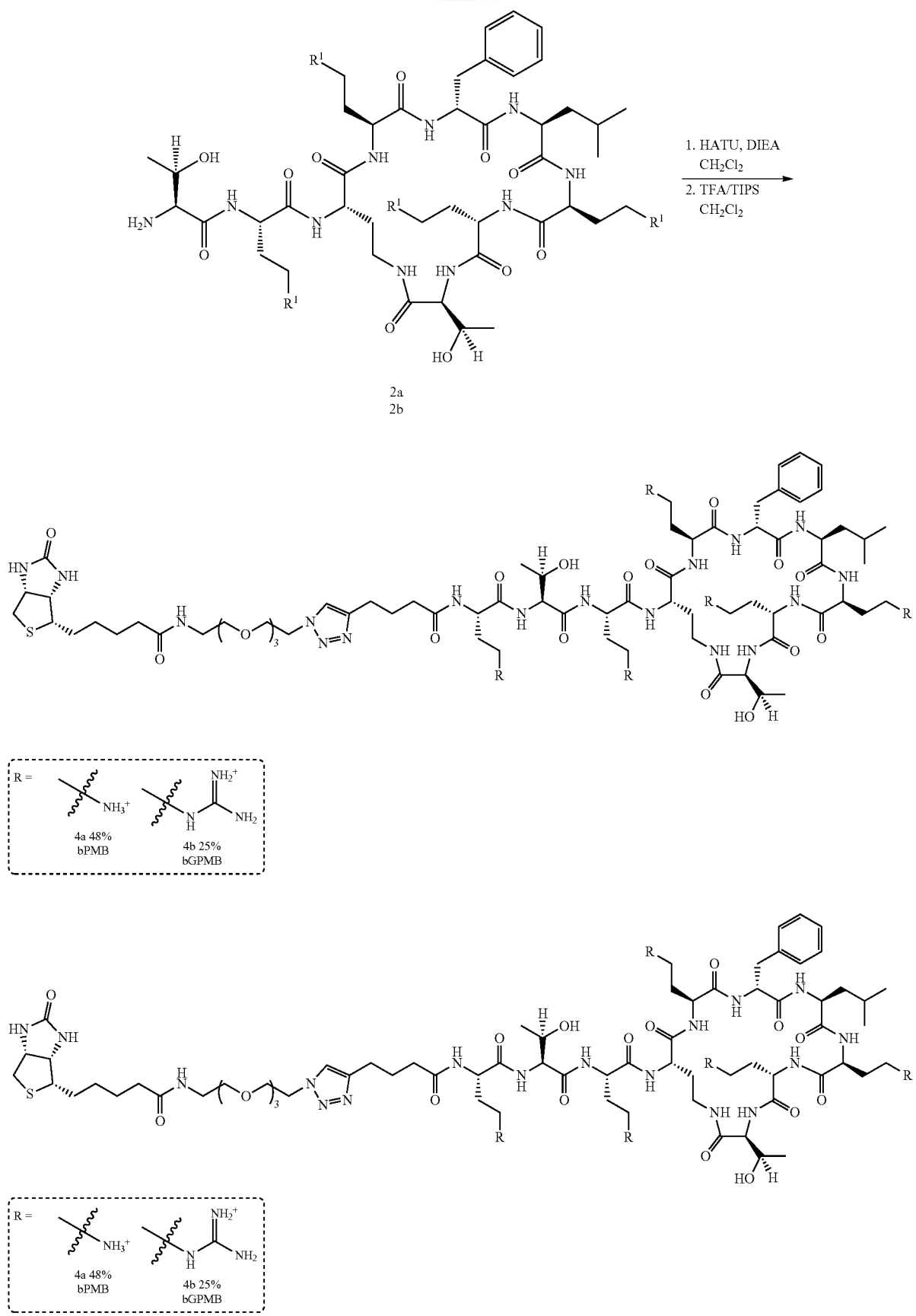

bPMB (Compound 4a)

BiotinBDabOH (3a, 20.6 mg, 0.0258 mmol), DIEA (8.6 mg, 0.067 mmol, 11.6 μL), HATU (10.2 mg, 0.027 mmol) and DMF (1 mL) were added to a 10 mL flask and stirred for 10 min. Then Boc-PMBN (2a, 30.4 mg, 0.022 mmol) was added to the reaction and stirred overnight. The reaction was diluted with $CH_2Cl_2$ and washed with 5% citric acid and then saturated $NaHCO_3$. The organic layer was then dried using $MgSO_4$, filtered, and evaporated under reduced pressure. The residue was then taken up in $CH_2Cl_2$/TFA (1:1, 1 mL) containing triisopropylsilane (10 μL) and stirred for 2 hours. The reaction was evaporated under reduced pressure the product was isolated by automated reverse phase flash chromatography using a Teledyne Isco Redisep Rf C18 5.5 g Gold column [5-30% CAN (0.1% TFA) in $H_2O$ (0.1% TFA) over 14 mins]. The fractions containing the desired product were lyophilized to provide 4a as a white solid as the TFA salt (19.9 mg, 0.0092 mmol, 48% yield).

$^1$H NMR (500 MHz, $D_2O$) δ 7.89 (dd, J=10.2, 1.9 Hz, 1H), 7.34-7.22 (m, 3H), 7.17 (d, J=5.2 Hz, 2H), 4.58-4.34 (m, 8H), 4.34-4.29 (m, 1H), 4.29-4.25 (m, 1H), 4.24-4.08 (m, 7H), 3.93-3.87 (m, 2H), 3.61-3.48 (m, 9H), 3.33-3.18 (m, 4H), 3.12-2.93 (m, 10H), 2.92-2.85 (m, 1H), 2.84-2.75 (m, 1H), 2.75-2.63 (m, 4H), 2.33-2.26 (m, 2H), 2.23-1.74 (m, 17H), 1.68-1.24 (m, 10H), 1.16-1.07 (m, 5H), 0.64 (d, J=37.2 Hz, 7H).

$^{13}$C NMR (126 MHz, $D_2O$) δ 176.73, 176.24, 174.90, 173.25, 173.18, 173.09, 172.89, 172.67, 172.62, 172.54, 172.47, 172.27, 172.21, 171.86, 171.61, 171.47, 171.28, 171.24, 165.17, 163.24, 162.82 (TFA, q, J=35.7 Hz), 146.46, 135.32, 128.83, 127.27, 124.28, 124.15, 116.23 (TFA, q, J=292.1 Hz), 69.43, 69.29, 69.26, 68.67, 68.43, 68.39, 66.89, 66.66, 66.08, 61.92, 60.08, 59.32, 58.93, 58.79, 55.62, 55.21, 52.66, 52.57, 51.74, 51.64, 51.55, 51.39, 51.25, 51.05, 50.92, 50.36, 50.24, 39.54, 38.94, 38.74, 36.69, 36.27, 36.19, 36.10, 35.94, 35.80, 35.70, 35.27, 34.22, 30.43, 30.31, 29.59, 29.54, 28.67, 28.48, 28.34, 28.09, 27.71, 27.60, 27.54, 25.00, 24.50, 24.44, 23.52, 23.42, 23.30, 22.18, 20.11, 18.95, 18.73, 18.58, 16.13.

HR-ESI-MS calculated for $C_{71}H_{120}N_{22}O_{18}S$ $[M+Na]^+$ 1623.8764, found 1623.8766.

bGPMB (Compound 4b)

BiotinBGDabOH (3b, 20.2 mg, 0.0223 mmol), DIEA (12.02 mg, 0.093 mmol, 16.2 μL), PyBrop (10.4 mg, 0.0223 mmol) and DMF (1 mL) were added to a 10 mL flask and stirred for 10 min. Then BocGuan-PMBN (2b, 36.0 mg, 0.0186 mmol) was added to the reaction and stirred overnight. The reaction was diluted with $CH_2Cl_2$ and washed with 5% citric acid and then saturated $NaHCO_3$. The organic layer was then dried using $MgSO_4$, filtered, and evaporated under reduced pressure. The residue was then taken up in $CH_2Cl_2$/TFA (1:1, 1 mL) containing triisopropylsilane (10 μL) and stirred for 2 hours. The reaction was evaporated under reduced pressure the product was isolated by automated reverse phase flash chromatography using a C18 5.5 g Gold column [15-35% ACN (0.1% TFA) in $H_2O$ (0.1% TFA) over 15 mins]. The fractions were lyophilized to provide 4b as a white solid as the TFA salt (19.9 mg, 0.0092 mmol, 25% yield).

$^1$H NMR (500 MHz, $D_2O$) δ 7.89-7.86 (m, 1H), 7.44-7.33 (m, 3H), 7.30-7.26 (m, 2H), 4.65-4.54 (m, 4H), 4.51-4.39 (m, 5H), 4.36-4.18 (m, 9H), 4.02-3.97 (m, 2H), 3.71-3.59 (m, 11H), 3.42-3.25 (m, 13H), 3.23-2.96 (m, 7H), 2.81-2.71 (m, 3H), 2.44-2.35 (m, 2H), 2.27 (td, J=7.3, 1.8 Hz, 3H), 2.24-2.10 (m, 6H), 2.23-1.30 (m, 28H), 1.27-1.18 (m, 6H), 0.89-0.70 (m, 7H).

$^{13}$C NMR (126 MHz, $D_2O$) δ 75, 176.59, 176.38, 175.00, 174.28, 173.96, 173.87, 173.83, 173.38, 173.32, 172.93, 172.63, 172.25, 172.25, 172.00, 171.67, 171.48, 171.43, 165.24, 163.35, 163.07, 162.79, 162.50 (TFA, q, J=35.7 Hz), 156.77, 156.68, 156.64, 156.54, 147.26, 135.40, 128.91, 127.37, 123.55, 117.43, 115.11 (TFA, q, J=291.5 Hz), 69.57, 69.52, 69.39, 68.78, 68.72, 66.85, 66.54, 66.06, 62.01, 60.19, 59.48, 59.29, 59.04, 55.86, 55.30, 52.59, 51.95, 51.70, 51.50, 51.18, 50.53, 49.84, 39.64, 39.04, 38.85, 37.83, 37.76, 37.39, 36.77, 35.39, 34.47, 34.38, 30.80, 29.76, 29.19, 27.84, 27.66, 25.10, 24.82, 23.95, 23.47, 22.29, 20.21, 19.09, 18.86, 18.72.

HR-ESI-MS calculated for $C_{76}H_{130}N_{32}O_{18}S$ $[M+3H]^{3+}$ 604.6727, found 604.6722.

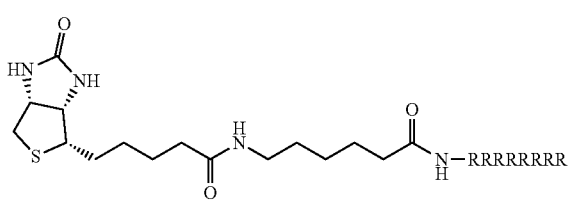

Octaarginine (bArg8)

bArg8 was synthesized using standard solid phase peptide synthesis protocols (Rink amide resin). An aminohexanoic acid (Ahx) spacer was introduced in the N-terminus and biotin-NHS (4 eq) was coupled to the peptide's N-terminus over 1 h at rt in DMF containing DIEA (8 eq). The peptide was cleaved from the resin using TFA/TIS/water (95:2.5:2.5) at rt for 3 h. The resin was filtered off and the peptide precipitated by the addition of cold ether and further standing at 4 degrees overnight. The crude was purified by HPLC using a semiprep RP-C18 column [5-60% ACN (0.1% TFA) in $H_2O$ (0.1% TFA) over 9 min].

HRMS of the isolated peak confirms the identity of the biotinylated peptide. Purity was confirmed by analytical HPLC. HR-ESI-MS calculated for $C_{64}H_{124}N_{36}O_{11}S$ $[M+2H]^{2+}$ 926.4376, found 926.4374.

Synthesis of bGTob and bTob bGTob and bTob were synthesized according to the following scheme. Synthesis of alkyne-boc-tobramycin (11a), alkyne-boc-guan-tobramycin (11b) and GTobbiotin (12b) were prepared according to literature procedures (see, e.g., A. V. Dix, L. Fischer, S. Sarrazin, C. P. H. Redgate, J. D. Esko, Y. Tor, Chembiochem, 2010, 11, 2302).

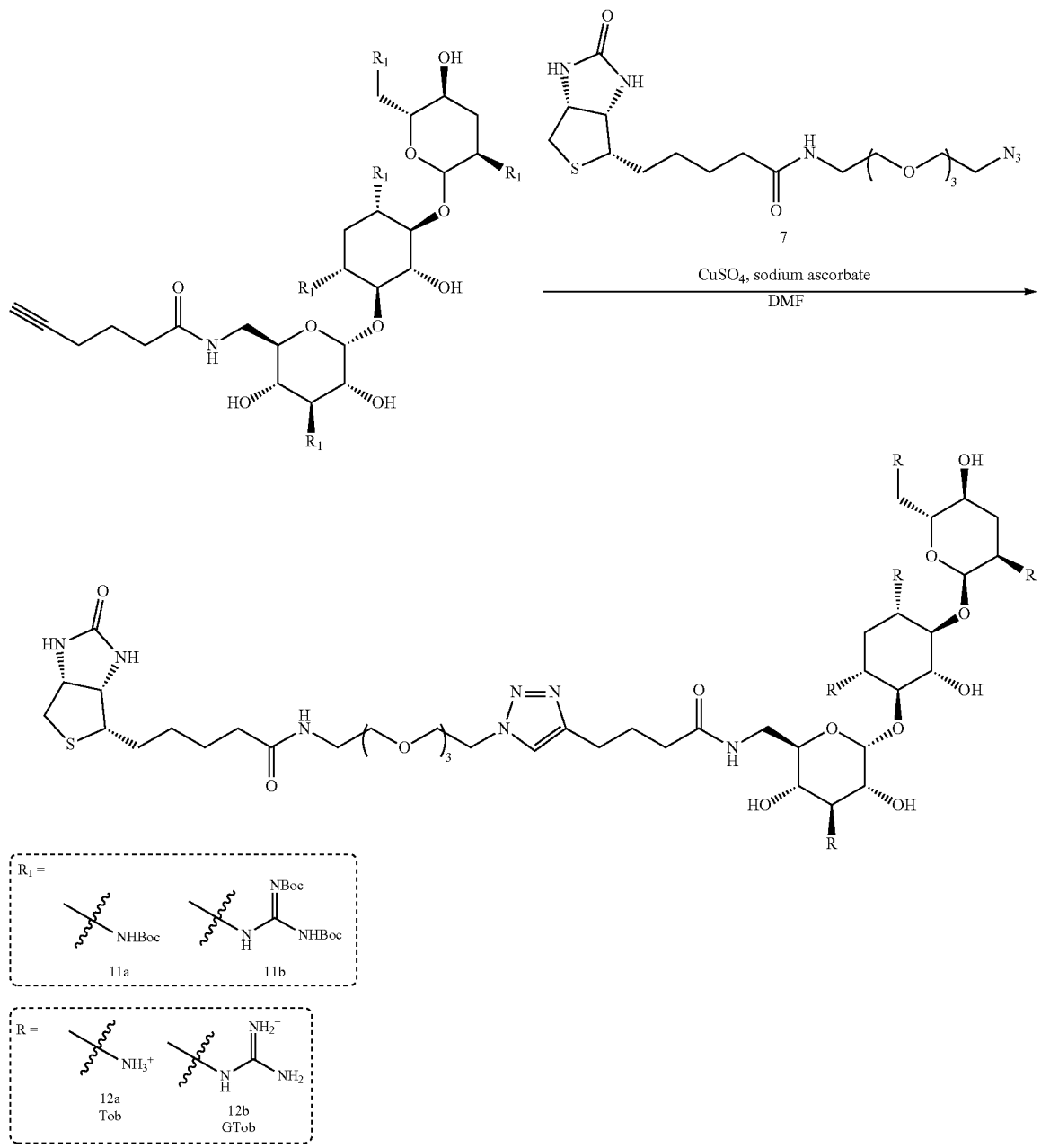

bTob (12a)

Alkyne-Boc-Tob (11a, 25 mg, 0.024 mmol) and biotin-PEG-$N_3$ (16 mg, 0.035 mmol) were dissolved in DMF (500 uL) and treated with 0.2M solution of sodium ascorbate in $H_2O$ (25 μL) and 0.2M solution of $CuSO_4.5H_2O$ (25 μL). The reaction was stirred overnight at room temperature under argon. The reaction was evaporated under reduced pressure. The crude product was dissolved in $CH_2Cl_2$ and washed with aqueous KCN solution, EDTA (0.3 M, pH 8) and brine. The organic layer was then dried using $MgSO_4$, filtered and evaporated under reduced pressure. The residue was then dissolved in $CH_2Cl_2$/TFA (1:1, 1 mL) containing triisopropylsilane (10 μL) and stirred for 2 hours. The reaction was evaporated under reduced pressure and the product was purified by HPLC using a semiprep RP-C18 column [5-30% ACN (0.1% TFA) in $H_2O$ (0.1% TFA) over 12 min]. The fractions containing the desired product were lyophilized to provide the product as a white solid, (20 mg, 0.013 mmol, 54% yield).

$^1$H NMR (500 MHz, $D_2O$): δ 7.80 (s, 1H), 5.70 (s, 1H), 4.96 (s, 1H), 4.50 (m, 3H), 4.30 (m, 1H), 3.91-3.80 (m, 6H), 3.73 (m, 1H), 3.66 (m, 2H), 3.60-3.40 (m, 16H), 3.38-3.27 (m, 3H), 3.26 (s, 2H), 3.19 (m, 2H), 2.88 (m, 1H), 2.65 (m, 3H), 2.45 (d, 1H, J=12.3 Hz), 2.22 (m, 3H), 2.13 (m, 2H), 1.96-1.83 (m, 4H), 1.62-1.40 (m, 4H), 1.28 (s, 2H). 13C NMR (126 MHz, $D_2O$): δ 176.82, 165.28, 163.30, 163.02, 162.74, 162.45, 146.91, 123.97, 119.77, 117.44, 115.12, 112.80, 100.86, 94.10, 83.56, 77.32, 74.12, 70.92, 70.31, 69.58, 69.53, 69.40, 69.38, 68.78, 68.60, 68.00, 66.48, 64.32, 62.02, 60.20, 55.30, 54.62, 50.15, 49.72, 48.31, 47.70, 39.74, 39.63, 38.94, 38.86, 35.38, 34.86, 29.25, 27.81, 27.71, 27.64, 25.09, 24.93, 23.78.

HR-ESI-MS calculated for $C_{42}H_{77}N_{12}O_{14}S$ $[M+H]^+$ 1005.5397, found 1005.5400.

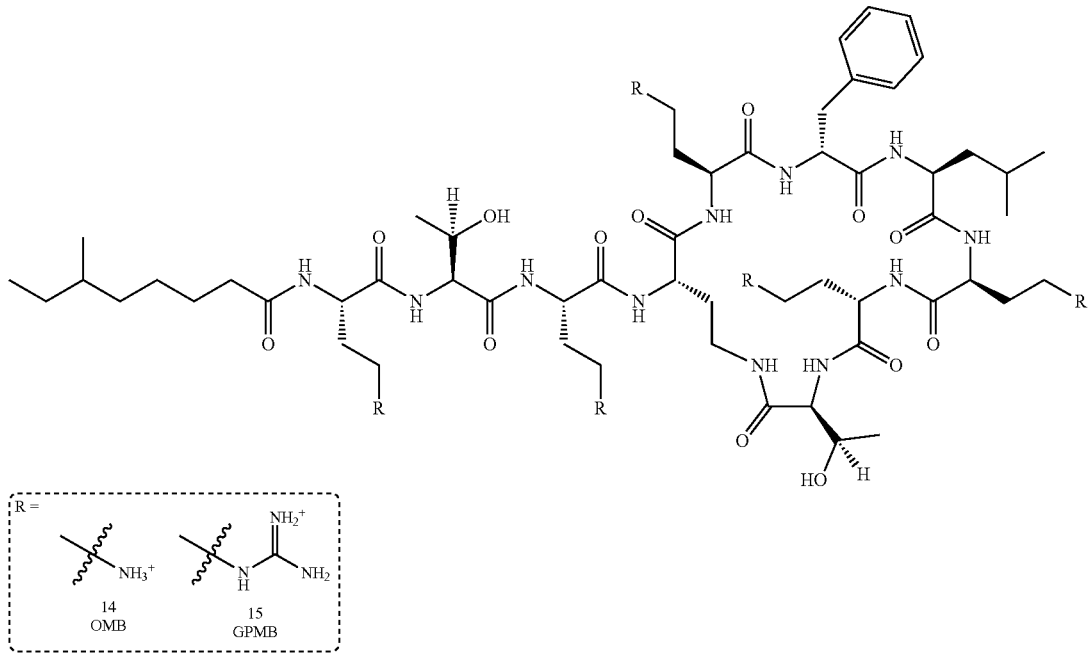

PMB (14)

PMB was isolated from the mixture of isomers by HPLC using a RP-C18 column [5-50% ACN (0.1% TFA) in $H_2O$ (0.1% TFA) over 40 mins]. Purity was confirmed by analytical HPLC. HR-ESI-MS calculated for $C_{56}H_{98}N_{16}O_{13}$ $[M+Na]^+$ 1225.7397, found 1225.7395.

GPMB (15)

MeOH (15 mL) and $NEt_3$ (239 mg, 2.36 mmol, 329 μL) were added to 14 (226 mg, 0.157 mmol) followed by N,N'-Di-Boc-1H-pyrazole-1-carboxamidine (195 mg, 0.142 mmol) and stirred overnight. The reaction was evaporated under reduced pressure and $CH_2Cl_2$ was added and washed with saturated $NaHCO_3$. The organic layer was dried over $MgSO_4$, filtered, and evaporated under reduced pressure. The residue was then dissolved in $CH_2Cl_2$/TFA (1:1, 4 mL) containing triisopropylsilane (44 μL) and stirred for 2 hours. The reaction was diluted with 5 mL of $CH_2Cl_2$ and extracted with 10 mL of $H_2O$. The water was evaporated under reduced pressure and the product was isolated by HPLC using a RPC18 column [5-50% ACN (0.1% TFA) in $H_2O$ (0.1% TFA) over 40 mins]. The fractions containing the desired product were lyophilized to provide the TFA salt of GPMB as a white solid, (74.7 mg, 0.0378 mmol, 24% yield). $^1$H NMR (400 MHz, $D_2O$): δ 7.42-7.29 (m, 3H), 7.26 (d, J=6.9 Hz, 2H), 4.56-4.50 (m, 1H), 4.45 (ddd, J=17.2, 8.7, 5.3 Hz, 3H), 4.35-4.21 (m, 6H), 4.20-4.14 (m, 2H), 3.43-2.98 (m, 14H), 2.33 (t, J=7.2 Hz, 2H), 2.22-1.74 (m, 12H), 1.67-1.03 (m, 17H), 0.82 (t, J=6.8 Hz, 6H), 0.75 (s, 3H), 0.68 (s, 3H). HR-ESI-MS calculated for $C_{61}H_{108}N_{26}O_{13}$ $[M+2H]^{2+}$ 707.4367, found 707.4351.

Example 2: Formation of Biotin-Streptavidin Complexes

Biotinylated transporters allow conjugation of the carriers to fluorescent proteins and the ability to test a variety of analogs in different assays (see, e.g., J. M. Hyman, E. I. Geihe, B. M. Trantow, B. Parvin and P. A. Wender, Proc. Natl. Acad. Sci. U.S.A, 2012, 109, 13225-13230; S. Console, C. Marty, C. Garcia-Echeverria, R. Schwendener and K. Ballmer-Hofer, J. Biol. Chem., 2003, 278, 35109-35114; G. Gasparini and S. Matile, Chemical Communications, 2015, 51, 17160-17162; J. Fu, C. Yu, L. Li and S. Q. Yao, J. Am. Chem. Soc., 2015, 137, 12153-12160). Biotin compounds were incubated in a 5:1 molar ratio with streptavidin derivatives for 20 min at room temperature. Conjugates were then diluted in culture medium to the final streptavidin concentration. Streptavidin conjugated to R-phycoerythrin (PE) coupled to the cyanine dye Cy5 (ST-PE-Cy5) was used as a high molecular weight model protein (MW=300 kDa), streptavidin-Cy5 (ST-Cy5) was used for microscopy experiments, and streptavidin-saporin was used to analyze cytosolic delivery.

Example 3: Cellular Uptake and Cell Surface Binding in Wild Type and Heparan Sulfate-Deficient CHO Cells Cell Culture Wild-type Chinese hamster ovary cells (CHO-K1) were obtained from the American Type Culture Collection (CCL-61). Mutant pgsA745 and pgsD677 were described previously (see, e.g., P. Pristovsek and J. Kidric, J. Med. Chem., 1999, 42, 4604-4613; M. Vaara, Microbiol. Rev., 1992, 56, 395-411). All cells were grown under an atmosphere of 5% $CO_2$ in air and 100% relative humidity. CHO-K1, pgsA, and pgsD cells were grown in F-12 medium (Life Technologies) supplemented with fetal bovine serum (10% v/v, Gemini Bio-Products) and penicillin/streptomycin solution (1% v/v). The Hep3B cell line was obtained from ATCC (HB-8064) and cultured in MEM (Invitrogen) supplemented with 10% fetal bovine serum, nonessential amino acids, and 1% penicillin/streptomycin. HEK293T cells were obtained from ATCC and maintained in Dulbecco's modified Eagle medium (DMEM) supplemented with 10% fetal bovine serum and 1% penicillin/streptomycin.

Quantifying Cellular Uptake/Binding

The polymyxin derivatives (2.5 µM in PBS) were incubated with ST-PE-Cy5 (0.5 µM in PBS) for 20 min at ambient temperature then diluted with F-12 cell culture medium to give final conjugate solutions.

Cells were plated onto 24-well plates (100 000 cells/well) and grown for 24 h to about 80% confluence. Cells were washed with PBS and incubated with 300 µL of the corresponding conjugate for 1 h at 37° C. under an atmosphere of 5% $CO_2$. Cells were washed twice with PBS, detached with 50 µL of trypsin-EDTA for uptake studies or 100 µL Versene (EDTA) for binding studies, diluted with PBS containing 0.1% BSA, and analyzed by FACS. Cellular uptake was quantified by the mean fluorescence intensity; raw data was interpreted by using FlowJo v8.8.6.

Wild type CHO-K1 cells were incubated with the carrier-ST-PE-Cy5 conjugate for 1 h at 37° C., detached with trypsin/EDTA, and analyzed by flow cytometry (see, e.g., H. O'Dowd, B. Kim, P. Margolis, W. Wang, C. Wu, S. L. Lopez and J. Blais, Tetrahedron Lett., 2007, 48, 2003-2005). Uptake of the fluorescent conjugate occurred at concentrations as low as 2 nM and increased in a dose dependent manner (FIG. 1A). bGTob showed uptake behavior similar to bPMB and bGPMB whereas bTob exhibited a ten-fold reduction in uptake. bArg8 showed approximately three-fold higher uptake than bPMB and bGPMB. Similar uptake patterns for bPMB and bGPMB were also observed in the human embryonic kidney cell line HEK-293 and the human hepatocyte cell line HEP-3B. Cellular uptake of GPMB and PMB conjugated to ST-PE-Cy5 was measured in CHO-K1, HEK-293, and HEP-3B cells. The cells were incubated with conjugate (5 nM) at 37° C. for 1 h. Mean fluorescence intensity was measured by flow cytometry. The background signal from untreated cells was subtracted (FIG. 2).

Figure 3A:
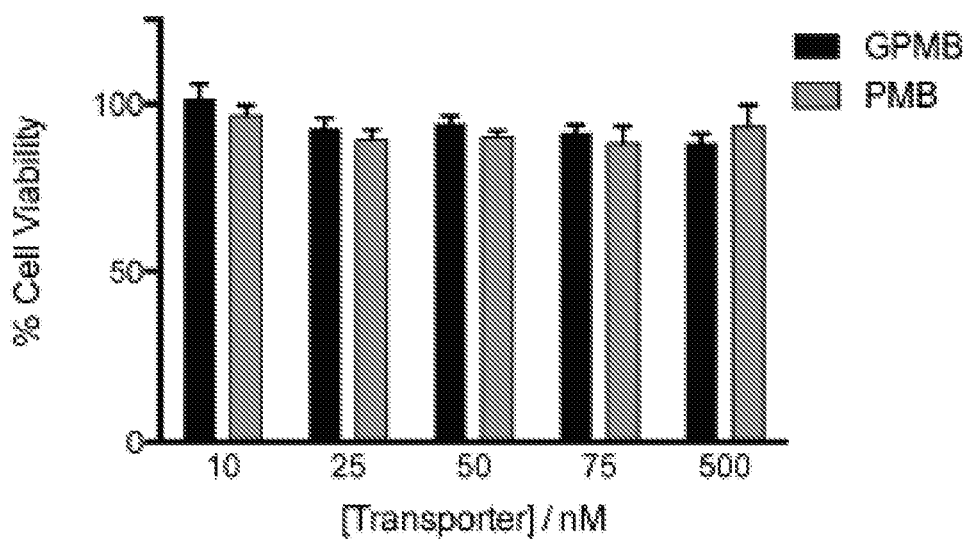
FIGS. 3A-3B show cell viability in CHO-K1 cells (FIG. 3A) and HEK-293 cells (FIG. 3B) incubated with various concentrations of GPMB-biotin or PMB-biotin.
Figure 3B:
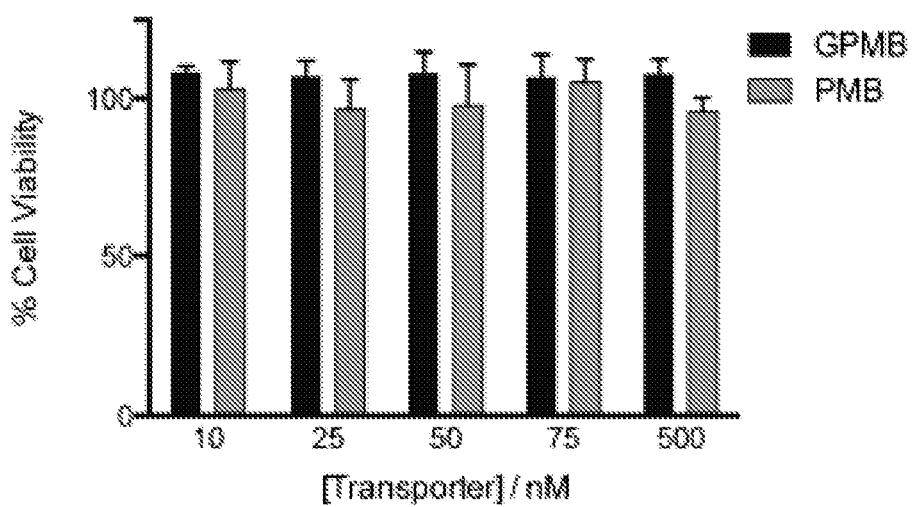

Cell-Titer Blue assays indicated that bPMB and bGPMB showed no cytotoxicity when incubated with either CHO-K1 or HEK-293 cell lines for 72 h at concentrations as high as 0.5 µM. CHO-K1 cells (FIG. 3A) and HEK-293 cells (FIG. 3B) were incubated with various concentrations of GPMB-biotin or PMB-biotin in complete media for 72 hours in a 96-well plate. Cell titer blue was added and incubated an additional 4 hours. Cell viability was calculated by measuring the fluorescence intensity at 560/590.

Figure 4:
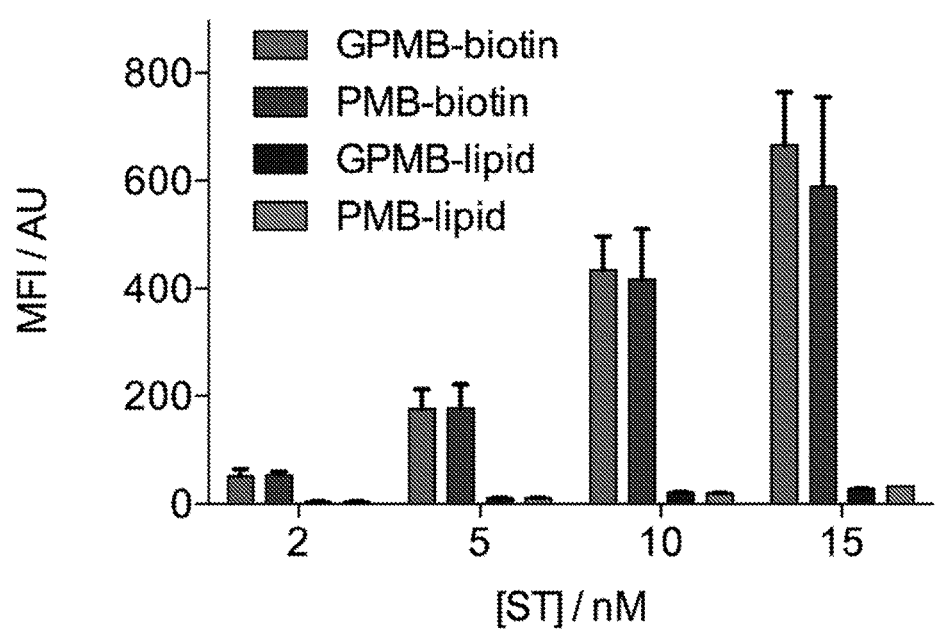
FIG. 4 shows cellular uptake control of ST-PE-Cy5 incubated with bPMB, bGPMB, PMB, or GPMB in CHO-K1 cells.

To demonstrate that the formation of a stable biotin-streptavidin complex was necessary for cellular delivery, ST-PE-Cy5 was incubated with bPMB, bGPMB, or PMB or GPMB (which do not contain the biotin moiety), then diluted to the desired final ST-PE-Cy5 concentrations. The mixtures were then added to CHO-K1 cells and incubated at 37° C. for 1 h. Mean fluorescence intensity was measured by flow cytometry and the background signal from untreated cells was subtracted. No enhanced uptake of ST-PE-Cy5 in the absence of the biotin-linked transporter was observed (FIG. 4).

The dependence of bPMB and bGPMB on cell surface heparan sulfate (HS) proteoglycans for cellular entry was evaluated using two mutant CHO cell lines, pgsA-745 which does not express HS or chondroitin sulfate/dermatan sulfate (CS/DS), and pgsD-677 which does not express HS but expresses 2- to 3-fold higher levels of CS/DS. bGPMB and bPMB streptavidin-PE-Cy5 conjugates conjugates (5 nM) were incubated with WT and mutant CHO cell lines for 1 h at 37° C. then lifted with EDTA/trypsin. Uptake in HS-deficient cell lines was reduced to <20% of that observed in wild-type cells (FIG. 1B).

To investigate cell-surface binding, CHO-K1 cells and pgsA-745 cells were incubated with 5 nM bGPMB and bPMB streptavidin-PE-Cy5 conjugates at 37° C. for 1 h and harvested using EDTA to prevent cleavage of cell-surface bound compounds. Cells were lifted with EDTA only (binding+uptake) or EDTA/trypsin (uptake). Binding values were determined by subtracting the MFI values obtained for cells lifted with EDTA/trypsin from those obtained for cells lifted with EDTA only. The fluorescence signal was compared to that observed when cells were lifted with EDTA/trypsin, which removes cell surface proteoglycans. For both bPMB and bGPMB, binding accounted for about 15% of the signal (FIG. 1C). Greater binding was observed in CHO-K1 cells compared to mutant pgsA-745 cells for both transporters (FIG. 1C).

Example 4: Mechanisms of Uptake

Cells were grown for 24 h in 24-well plates as described above. Cells were incubated at 4° C. for 15 min in F-12, washed with cold PBS, then incubated with the precooled conjugate solution for 30 min at 4° C. Cells were washed, detached with trypsin-EDTA, and analyzed as described above.

Cells were grown for 24 h in 24-well plates as described above, washed with PBS, and incubated with 5 mM amiloride for 10 min or 400 mM sucrose, 20 µM chlorpromazine, 200 µM genistein, or 5 µM nystatin for 30 mM at 37° C. Cells were then washed with PBS and treated with the conjugate solution in F-12 for the cells pre-treated with amiloride, or the conjugate solution in the presence of the inhibitor, using the same concentration used for pre-treatment, for 1 h at 37° C. under an atmosphere of 5% $CO_2$. Cells were washed, detached with trypsin-EDTA, and analyzed as described above.

To shed light on the internalization mechanism(s), the contribution of various endocytotic pathways was evaluated pharmacologically. CHO-K1 cells were incubated with streptavidin-PE-Cy5 bPMB or bGPMB conjugates (5 nM) at 4° C. to assess the contribution of energy-dependent processes. Further, uptake was evaluated in cells pretreated with inhibitors of macropinocytosis (amiloride), clathrin-mediated endocytosis (sucrose and chlorpromazine) or caveolae-mediated endocytosis (genistein and nystatin) (FIG. 1D). For inhibition experiments, cells were pretreated with amiloride (Am, 10 min, 5 mM), sucrose (Suc, 30 min, 400 mM), chlorpromazine (CPZ, 30 min, 20 µM), genistein (Gen, 30 mM, 200 µM), or nystatin (Nys, 30 min, 5 µM) at 37° C. prior to incubation with the conjugates (5 nM) for 1 h at 37° C. in the presence of inhibitor (except Am). The MFI was normalized.

Figure 5:
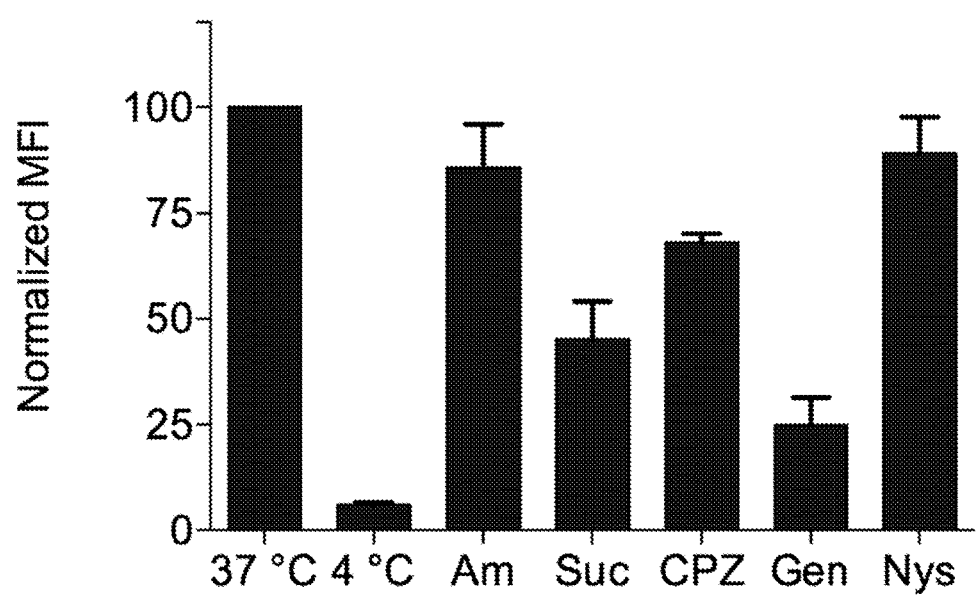
FIG. 5 shows the mechanisms of GTob uptake in CHO-K1 cells.

The inhibitory effect on the uptake of bGTob was also evaluated for comparison. CHO-K1 cells were incubated with GTob conjugated to streptavidin-PE-Cy5 (5 nM) for 1 h at 37° C. or 4° C. For inhibition experiments, cells were pretreated with amiloride (Am, 10 min, 5 mM), sucrose (Suc, 30 min, 400 mM), chlorpromazine (CPZ, 30 min, 20 µM), genistein (Gen, 30 min, 200 µM), or nystatin (Nys, 30 min, 5 µM) at 37° C. prior to incubation with the conjugates (5 nM) for 1 h at 37° C. in the presence of inhibitor (except Am). The background signal from untreated cells was subtracted and the MFI was normalized. While low temperature practically abolished internalization of the streptavidin-PE-Cy5 bPMB or bGPMB conjugates, treatment with amiloride, sucrose or chlorpromazine did not affect the cellular uptake of bPMB or bGPMB high MW conjugates. However, in cells treated with either genistein or nystatin, cellular uptake was reduced by ~50-60%, indicating that bPMB and bGPMB conjugates internalize through energy-dependent processes, presumably through caveolae-mediated pathways. bGTob, on the other hand, showed reduced uptake in the presence of sucrose, chlorpromazine and genistein and no change in uptake when cells were treated with amiloride or nystatin (FIG. 5), indicating a different mechanism of uptake.

Example 5: Intracellular Localization

CHO-K1 cells were grown for 24 h in 35 mm dishes equipped with a glass bottom coverslip coated with poly-D-lysine. Cells were washed with PBS, treated with 1.5 mL of transporter conjugated to ST-Cy5 (20 nM) and incubated at 37° C. for 1 h under an atmosphere of 5% $CO_2$. Cells were washed with PBS and stained with Hoescht stain and LysoTracker. Images were processed and analyzed using Nikon Imaging Software Elements and ImageJ. Pearson's correlations were calculated for individual cells in three separate images from two different experiments and then averaged (n=30).

Figures 6A, 6B, 6C:
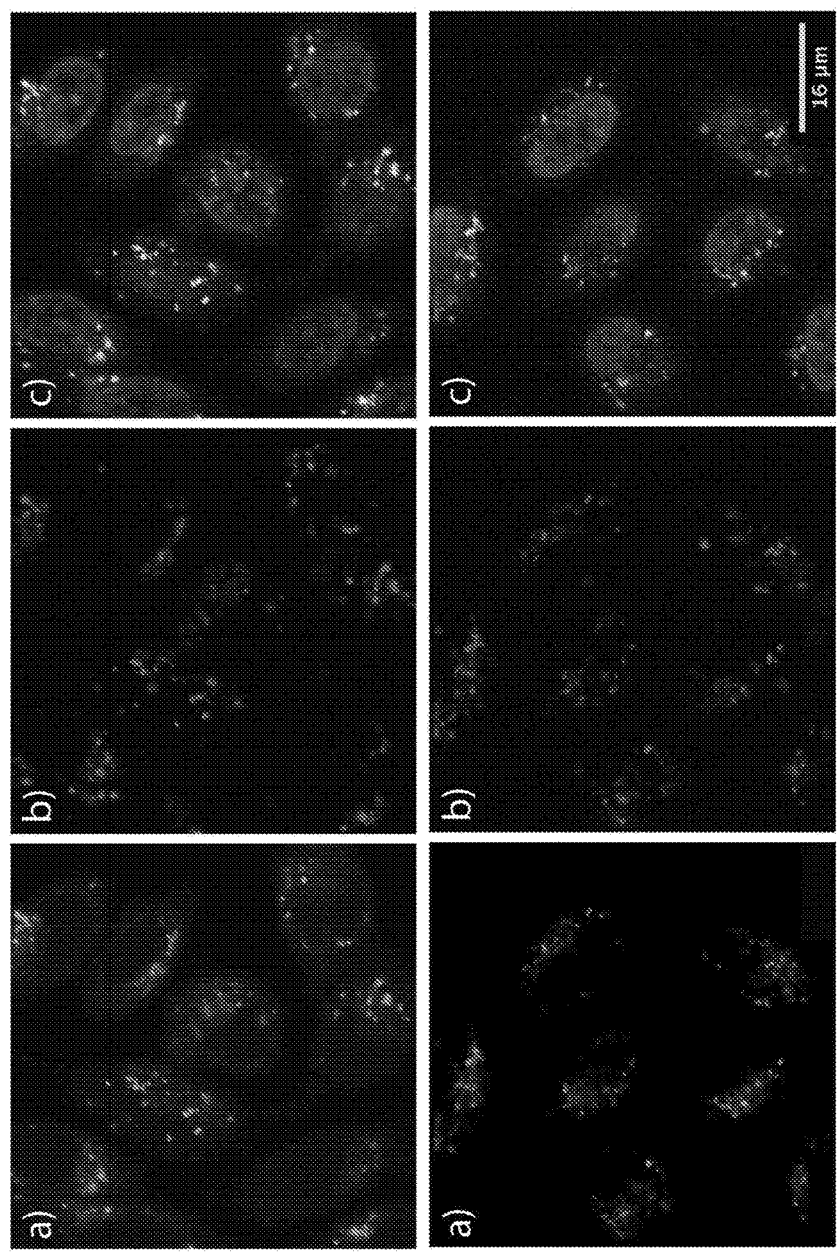
FIGS. 6A-6C show intracellular localization of GPMB and PMB in CHO-K1 cells. The top panels of FIGS. 6A-6C show CHO-K1 cells incubated with GPMB, while the bottom panels show CHO-K1 cells incubated with PMB.
Figure 7:
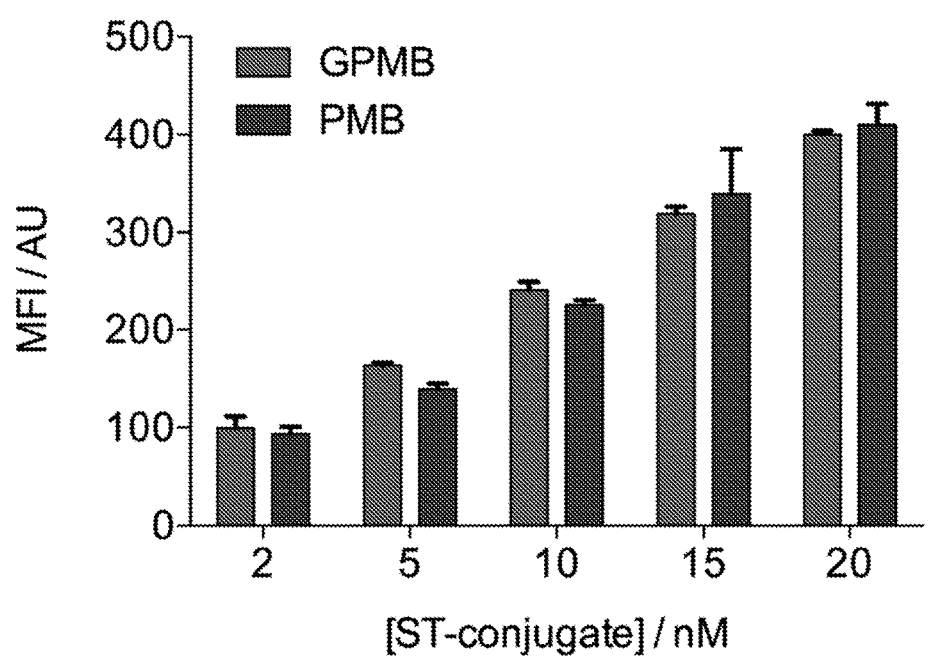
FIG. 7 shows cellular uptake of ST-Cy5 in CHO-K1 cells.

To learn about the intracellular localization of these transporters, wild type CHO-K1 cells were incubated with GPMB (FIG. 6A, top panel) or PMB (FIG. 6A, bottom panel) conjugated to streptavidin-Cy5 (20 nM) for 1 h at 37° C. and imaged using confocal laser scanning microscopy (CLSM). Cells were further treated with the nuclear stain Hoechst 33342 (FIG. 6C) and the lysosomal marker LysoTracker Green DND-26 (FIG. 6B). The images show transporter accumulation in punctate vesicles. Overlaying the images from the green and far red (pseudo-colored in red) channels revealed a moderate degree of co-localization for the conjugates and LysoTracker-stained compartments, resulting in a Pearson's correlation of 0.62 for both bPMB and bGPMB. The cellular uptake of ST-Cy5 was analyzed. CHO-K1 cells were incubated with PMB or GPMB conjugated to streptavidin-PE-Cy5 at various concentrations for 1 h at 37° C. Mean fluorescence intensity was measured and the background signal from untreated cells was subtracted. FACS analyses of carrier-ST-Cy5 conjugates up to 20 nM (FIG. 7) were consistent with ST-PE-Cy5 delivery.

Example 6: Cytoplasmic Delivery

The biotinylated transporters were incubated with ST-Sap in a 5:1 molar ratio for 20 min at ambient temperature then diluted with F-12 cell culture medium to give final conjugate solutions. CHO-K1 and pgsA cells were incubated with 100 µL of the corresponding conjugate for 4 days at 37° C. under an atmosphere of 5% $CO_2$. CellTiter-Blue (20 µL) was added to the medium and incubated for an additional 4 h to measure viability.

Figure 8:
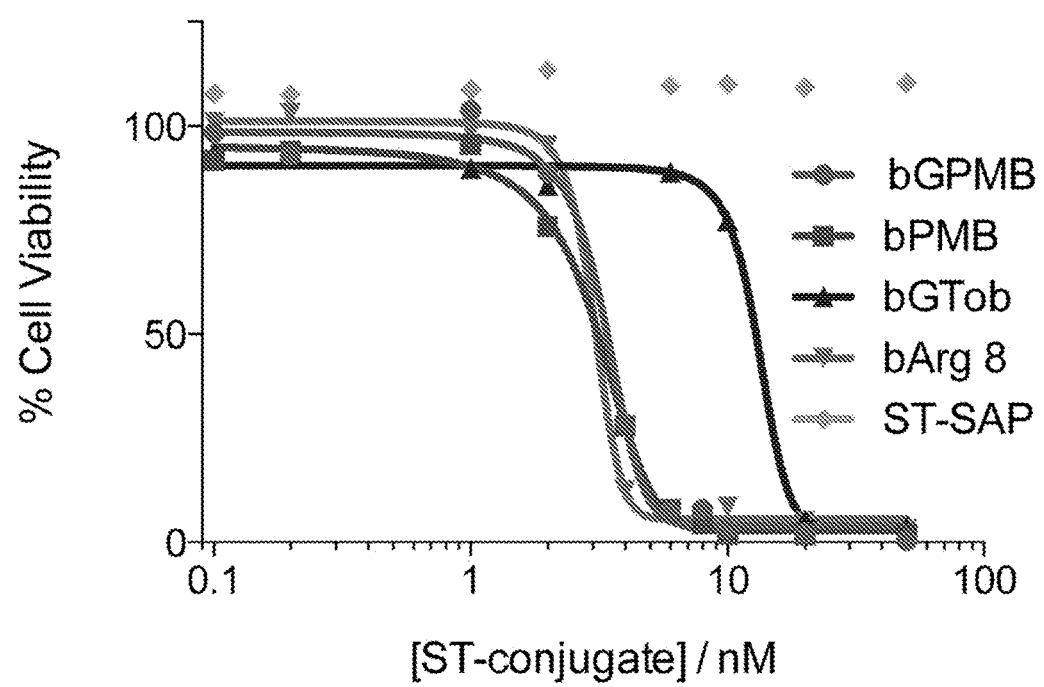
FIG. 8 shows the delivery of saporin to the cytosol of CHO-K1 cells.

The ability of bPMB and bGPMB to deliver cargo to the cytosol was evaluated by conjugating the transporter to streptavidin-saporin (ST-SAP) and incubating the conjugate with CHO-K1 or pgsA cells at various concentrations. CHO-K1 cells were incubated with transporter-streptavidin-saporin conjugates at 37° C. After four days, the CellTiter-Blue assay was used to assess the number of viable cells and fluorescence intensity was measured at 560/590. bPMB and bGPMB had $LD_{50}$ values of 3.1 nM and 3.3 nM respectively, while bGTob had an $LD_{50}$ value of 13.2 nM and bArg8 had an LD50 value of 3.1 nM (FIG. 8).

Figure 9A:
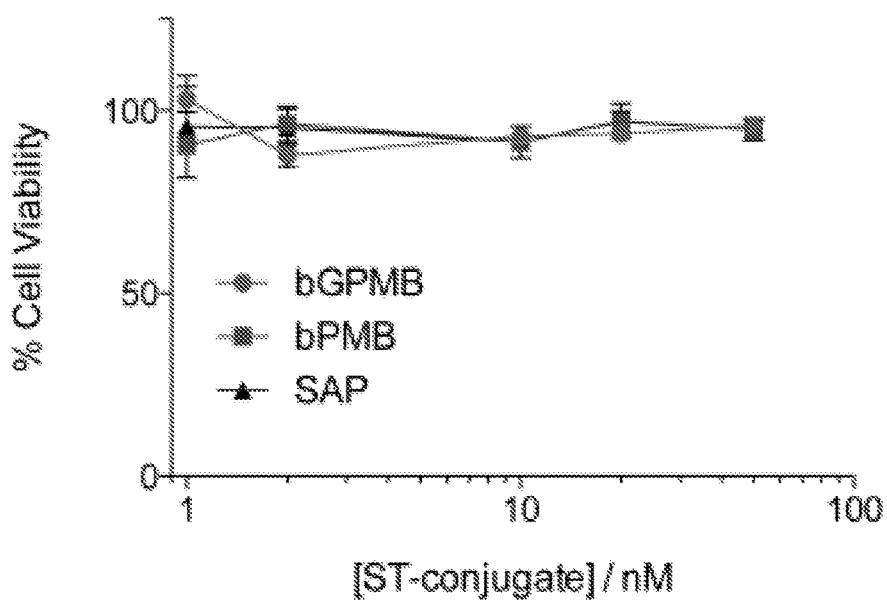
FIGS. 9A-9B shows cellular uptake of saporin in CHO-K1 cells.
Figure 9B:
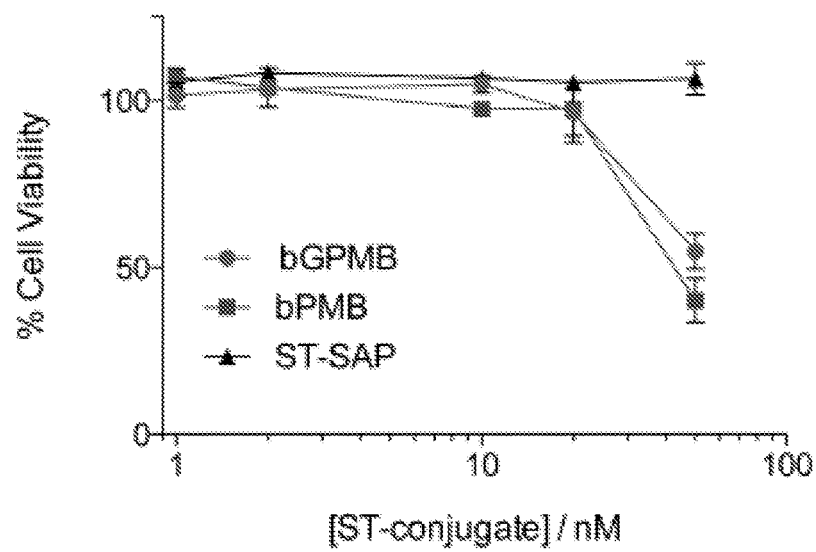

Additionally, ST-SAP without transporter or saporin without streptavidin incubated with bPMB and bGPMB were unable to induce cell death, indicating the need of forming the biotin-ST complex. ST-SAP-transporter conjugates showed no toxicity in pgsA cells. Saporin (no streptavidin) was incubated with bPMB or bGPMB for 20 min then diluted to final saporin concentrations and added to CHO-K1 cells. After four days, the number of viable cells was determined using CellTiter-Blue assay and the fluorescence intensity at was measured at 560/590 (FIG. 9A). pgsA cells were incubated with transporter-streptavidin-saporin conjugates at 37° C. After four days, the number of viable cells was determined using CellTiter-Blue and fluorescence intensity was measured at 560/590 (FIG. 9B).

Example 7: Cellular Uptake of bPMB and bGPMB Modified Liposomes

A mixture (30 mg total) of DOPC, DOPE, and cholesterol (73:11:16) was dissolved in chloroform to a final volume of 1 mL and evaporated in a round flask and further dried under high vacuum overnight to form a thin lipid layer. The resulting film was hydrated for 15 min at 37° C. with 1 mL of PBS containing 100 µM Cy5. The mixture was sonicated for 30 s, subjected to six freeze/thaw cycles using a dry ice/acetone bath and a water bath at 37° C. Lastly, the suspension was extruded 17 times through a polycarbonate membrane (pore size 100 nm) at room temperature. Non-encapsulated dye was removed by gravitational gel filtration (Sephadex G-50). Lipid concentration was determined adapting the Stewart method. Liposomes were diluted to 3 mg/mL and used as is (plain liposomes) or mixed with 10 mol % PMB or GPMB for 1 h at room temperature. Unincorporated PMB or GPMB was removed via centrifuge gel filtration (Sephadex G-50) (see, e.g., D. W. Fry, J. C. White and I. D. Goldman, Anal. Biochem., 1978, 90, 809-815).

To examine the significance of the cyclic peptide as a delivery module, rather than the lipophilic tail, and the versatility of PMB and GPMB as transporters, liposomes containing the fluorescent Cy5 dye were mixed with 10 mol % PMB or GPMB. Uptake was evaluated using flow cytometry and the size and zeta potential of the liposomes were measured using dynamic light scattering (DLS) and are shown in Table 1 below. Size, polydispersity, and zeta-potential of evaluated liposomes are shown. Plain liposomes were compared to liposomes mixed with 10 mol % GPMB or 10 mol % PMB.

TABLE 1

Physicochemical characterization of liposomes.

| | Z-average (±SD)/nm | PDI (±SD) | Z-potential (±SD)/mV |
|---|---|---|---|
| Plain liposomes | 143.9 (4.0) | 0.122 (.039) | 3.78 (0.09) |
| GPMB liposomes | 138.2 (1.9) | 0.166 (0.021) | 26.9 (0.70) |
| PMB liposomes | 139.7 (1.7) | 0.164 (0.056) | 22.0 (0.70) |

Figure 10:
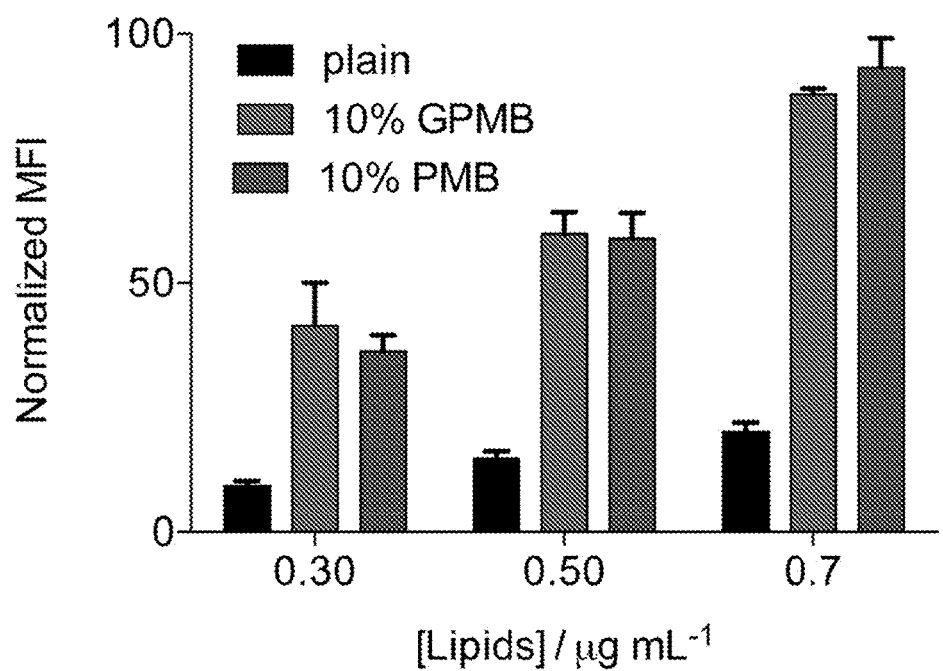
FIG. 10 shows cellular uptake of liposomes in CHO-K1 cells.
Figure 11:
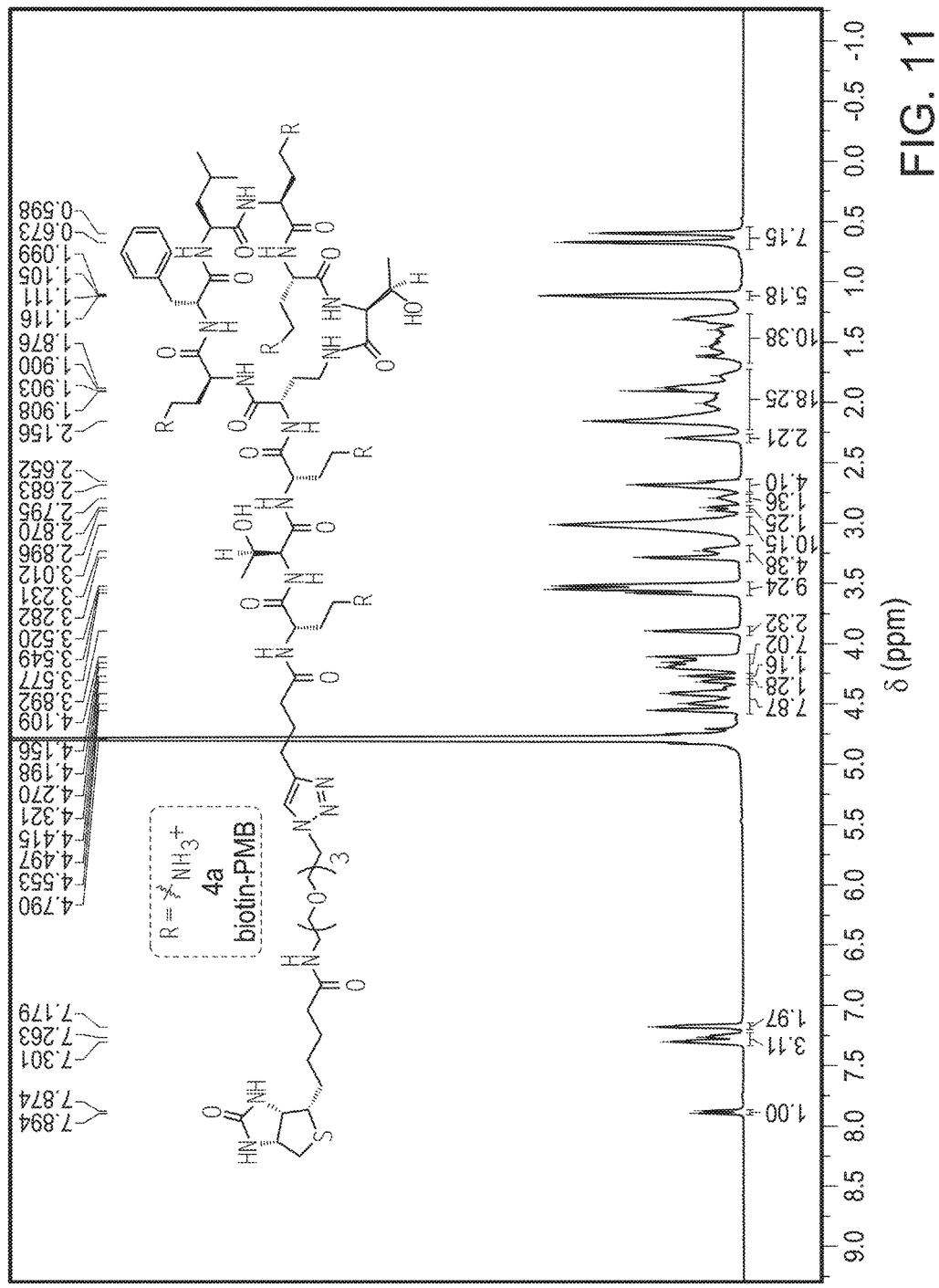
FIG. 11 is the $^1$H NMR of PMB-biotin (4a, $D_2O$, 500 MHz).
Figure 12:
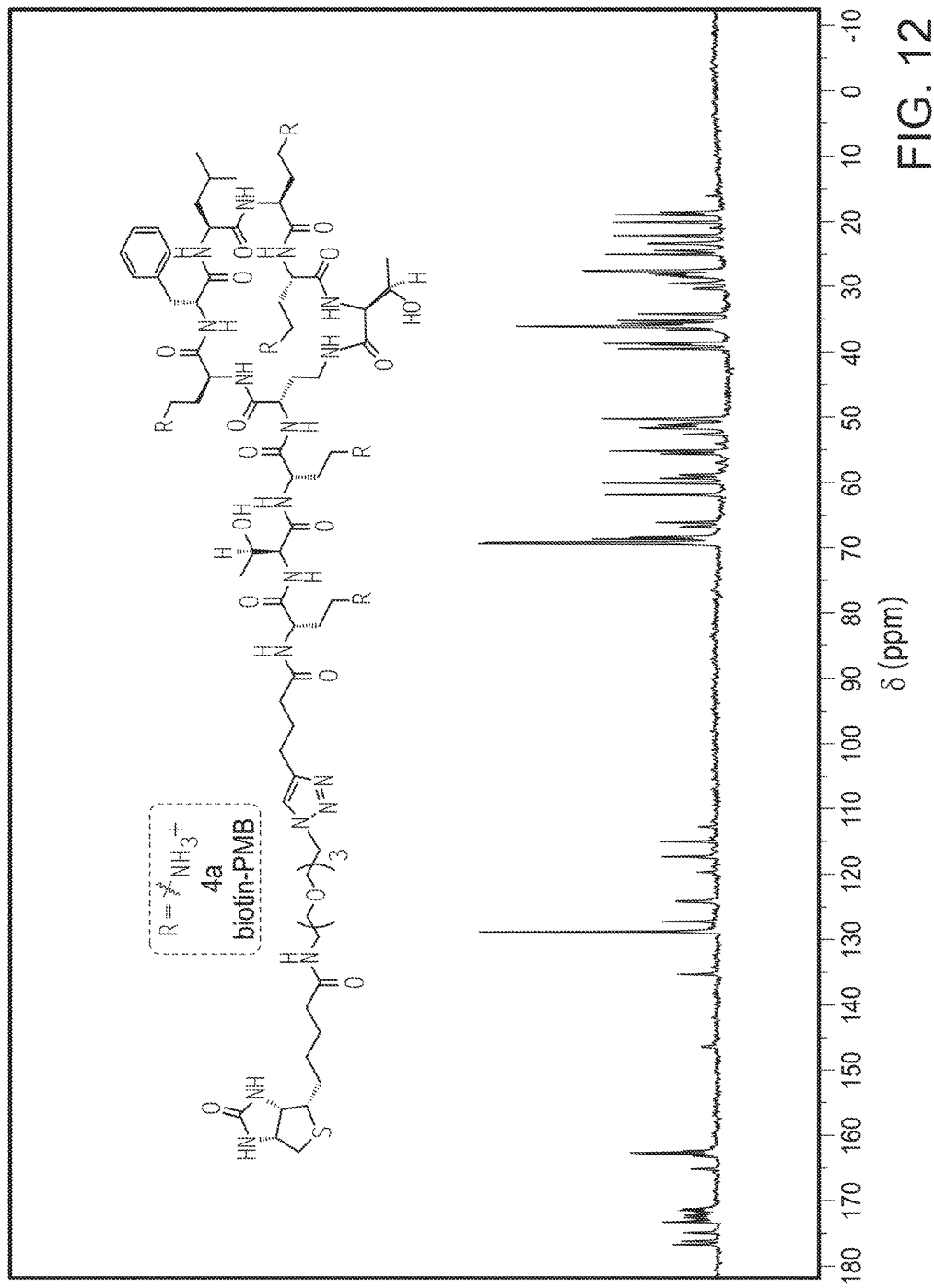
FIG. 12 is the $^{13}$C NMR of PMB-biotin (4a, $D_2O$, 126 MHz).
Figure 13:
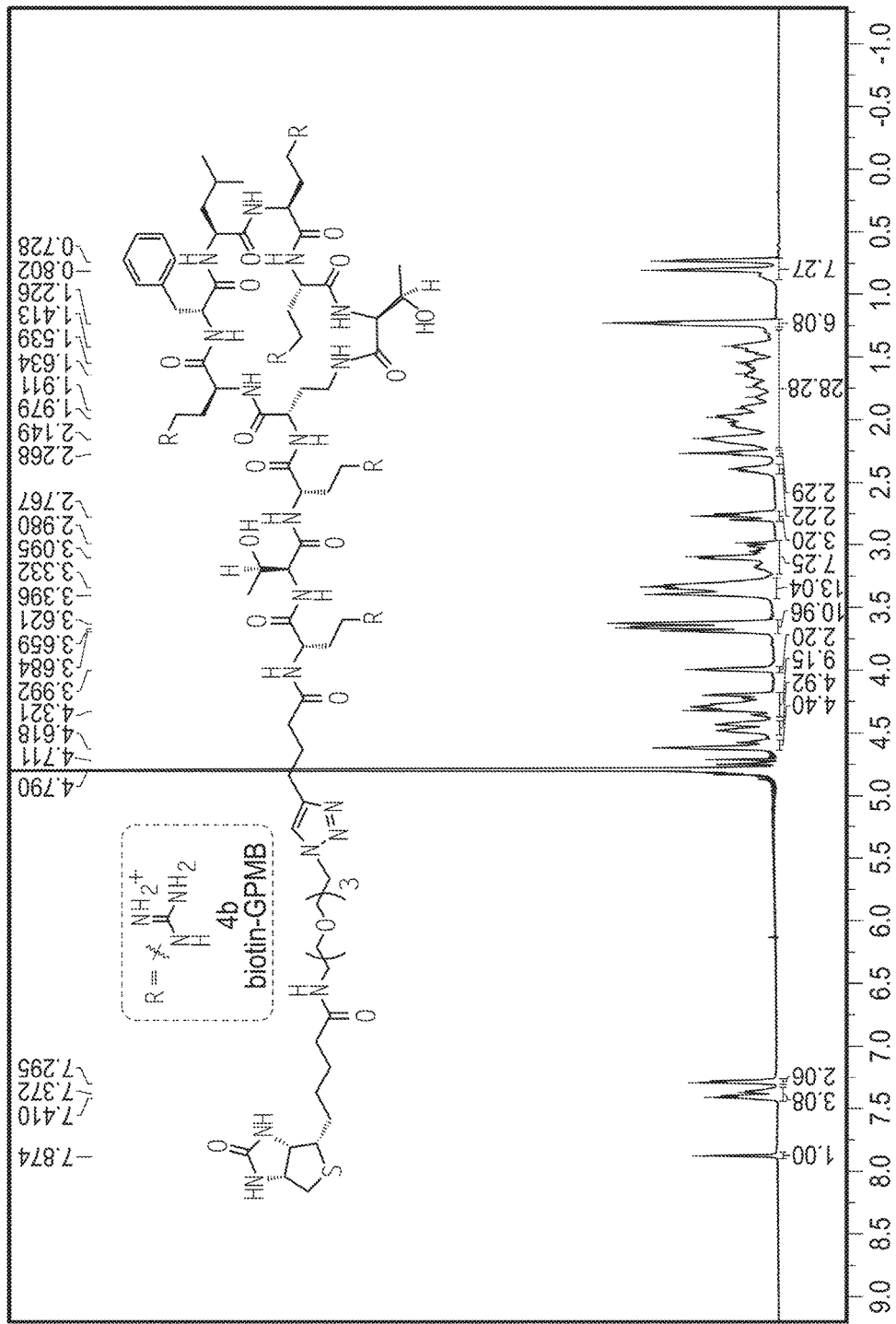
FIG. 13 is the $^1$H NMR of GPMB-biotin (4b, $D_2O$, 500 MHz).
Figure 14:
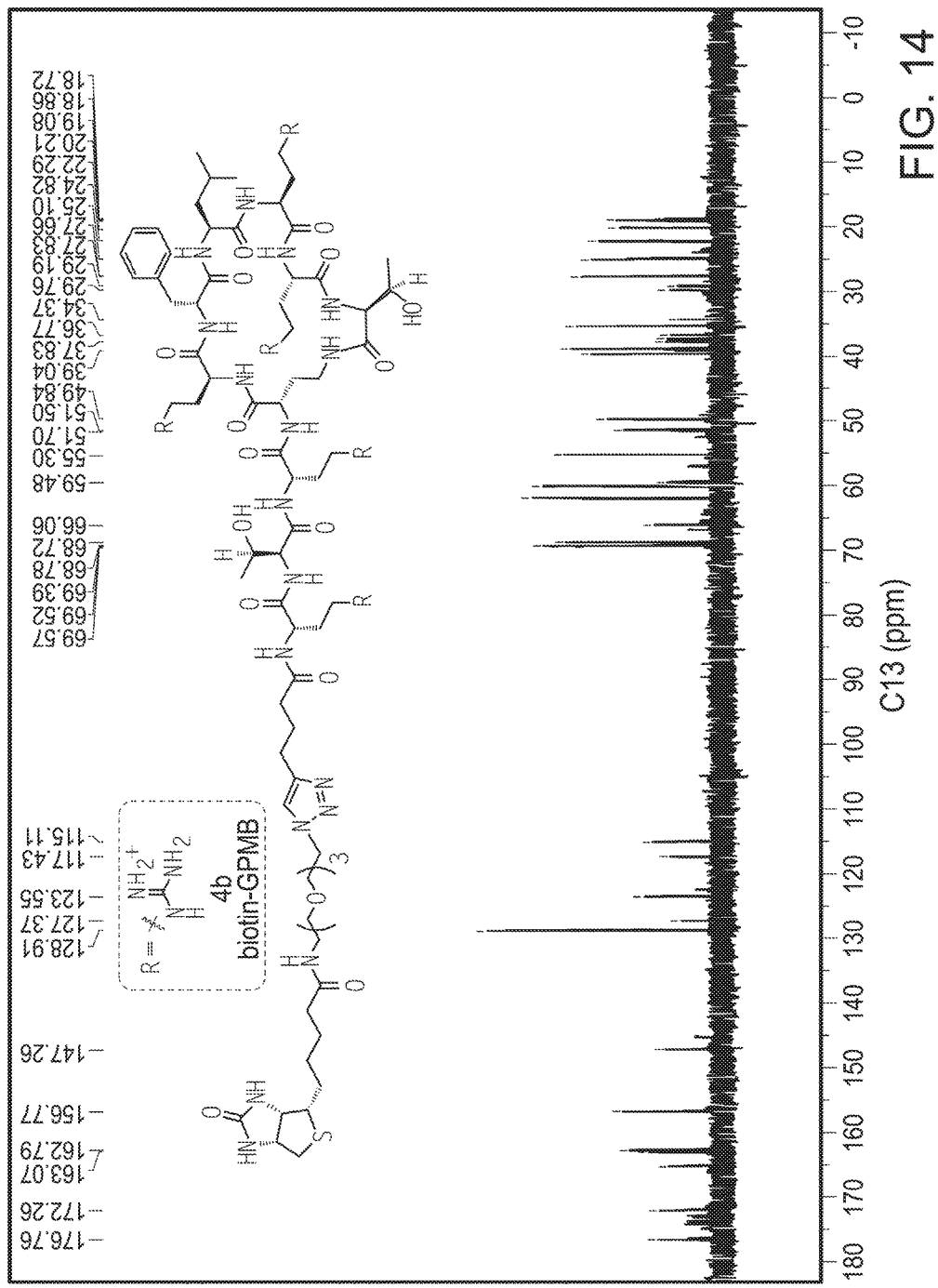
FIG. 14 is the $^{13}$C NMR of GPMB-biotin (4b, $D_2O$, 126 MHz).
Figure 15:
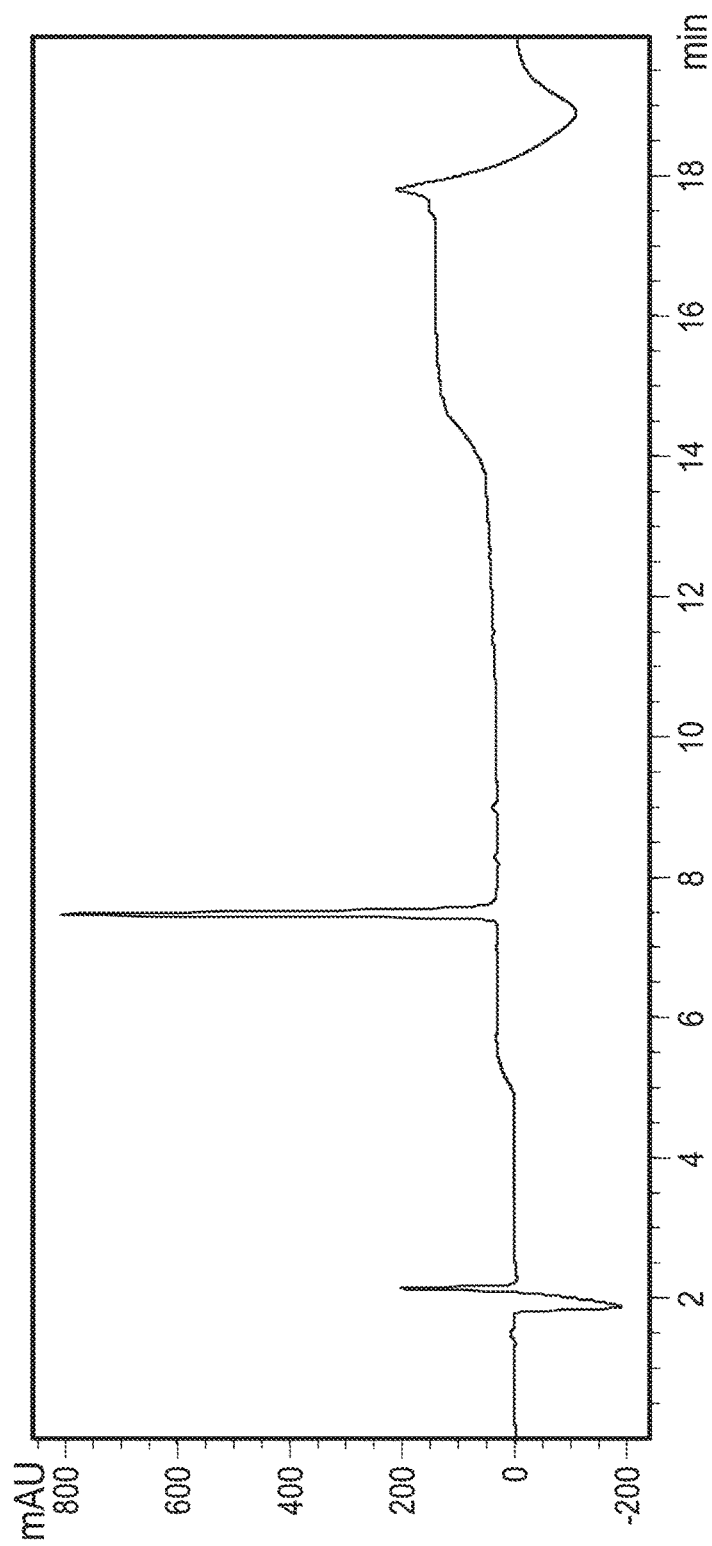
FIG. 15 is the analytical HPLC trace for bArg8. [RP-C18, 5-60% ACN (0.1% TFA) in $H_2O$ (0.1% TFA) over 9 min].
Figure 16:
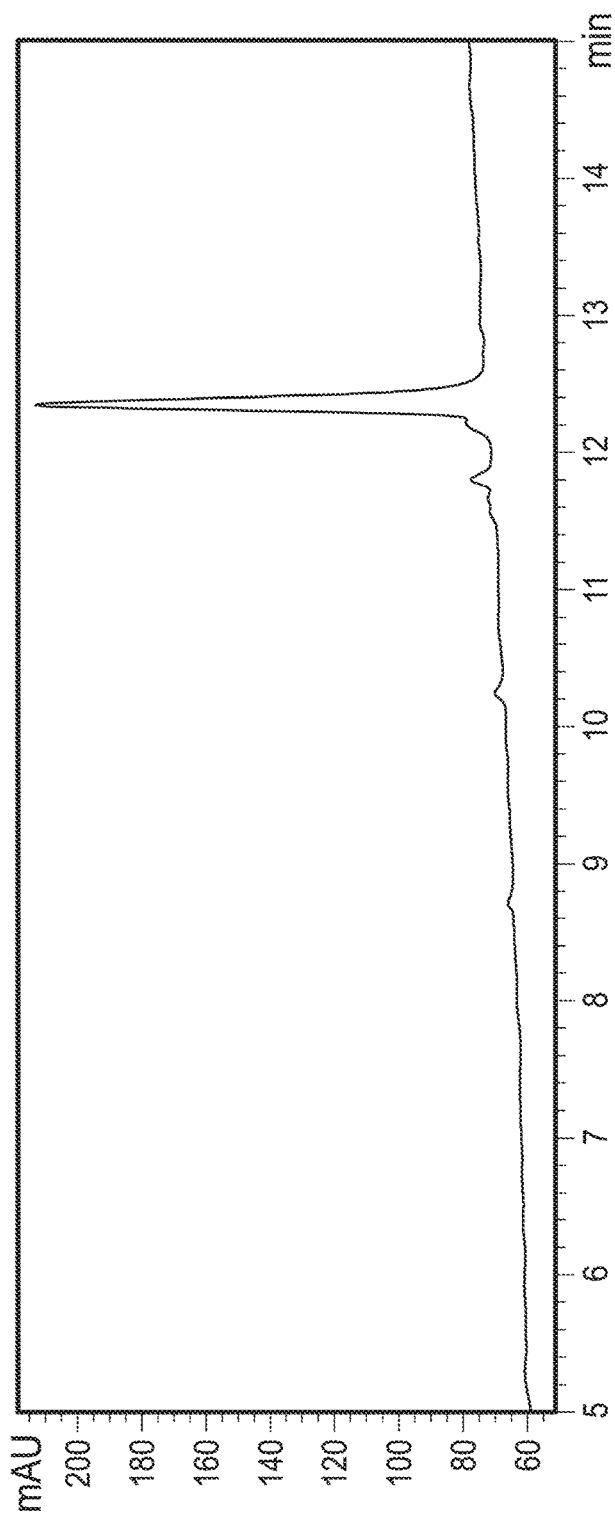
FIG. 16 is the analytical HPLC trace for PMB [RP-C18 column, 5-50% ACN (0.1% TFA) in $H_2O$ (0.1% TFA) over 15 mins].
Figure 17:
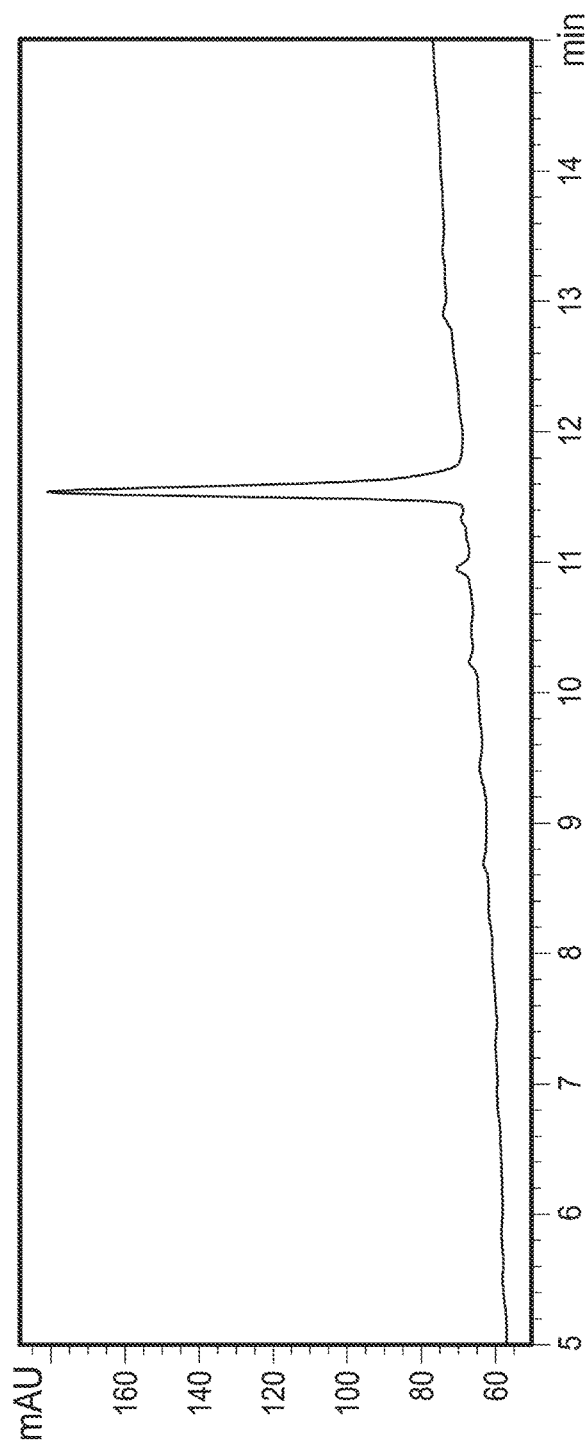
FIG. 17 is the analytical HPLC trace for GPMB [RP-C18 column, 5-50% ACN (0.1% TFA) in $H_2O$ (0.1% TFA) over 15 mins].
Figure 18:
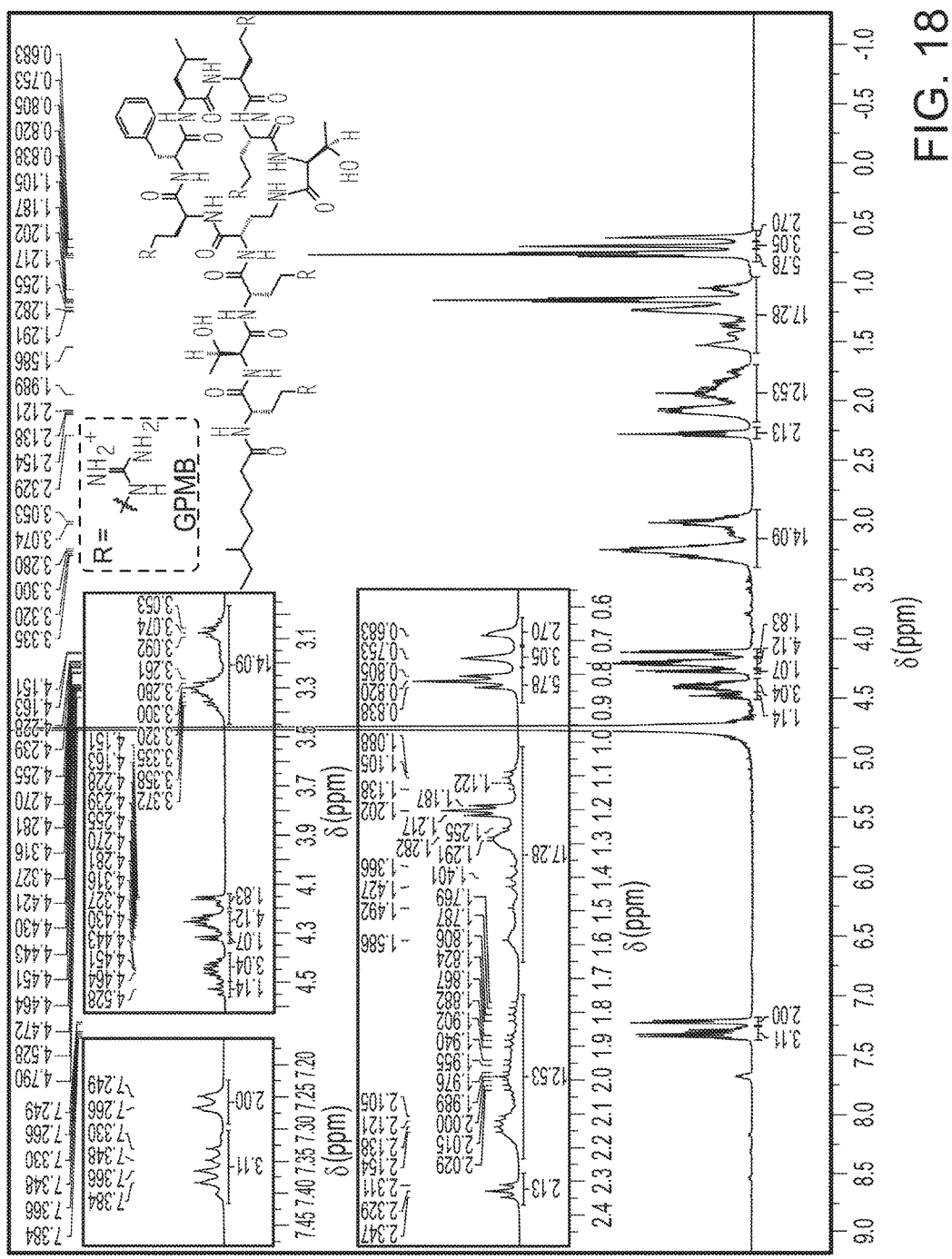
FIG. 18 is the $^1H$ NMR of GPMB ($D_2O$, 500 MHz).

CHO-K1 cells were incubated with plain and PMB or GPMB decorated liposomes at 0.30, 0.50, or 0.70 µg/mL for 1 h at 37° C. The background signal from untreated cells was subtracted and the MFI was normalized. Both carriers showed the ability to enhance delivery of cargo containing liposomes into wild-type CHO cells with similar efficacy (FIG. 10).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of formula (Ia)

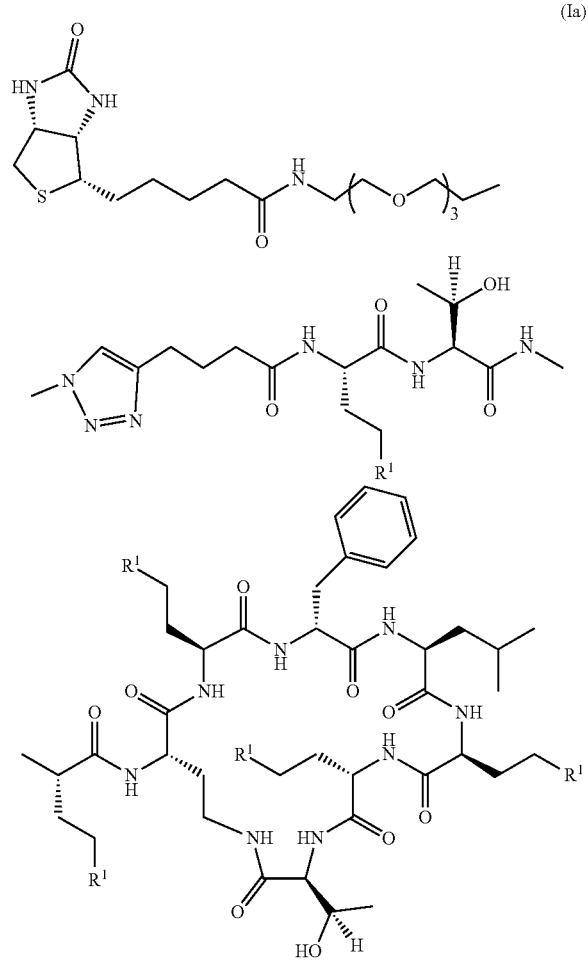

(Ia)

wherein each $R^1$ is independently selected from an ammonium group and a guanidinium group.

2. A method of delivering cargo into mammalian cells, comprising:
  a) coupling the cargo with a compound of Formula (Ia) to form a conjugate, wherein:
     each $R^1$ is independently selected from among an ammonium group ($-NH_3^+$) and a guanidinium group ($-NH-C(=NH_2^+)-NH_2$);
  and
  b) contacting the cells with the conjugate.

3. The method of claim 2, wherein each $R^1$ is $-NH_3^+$.

4. The method of claim 2, wherein each $R^1$ is $-NH-C(=NH_2^+)-NH_2$.

5. The method of claim 2, wherein the cargo has limited cellular uptake.

6. The method of claim 2, wherein the cargo is selected from among a large biomolecule, a protein, an oligonucleotide, a drug, a liposome, a liposomal assembly, and combinations thereof.

7. The method of claim 6, wherein the cargo has a molecular weight of greater than about 30, 50, 100, 200, 300, 500, or 1000 kDa.

8. The method of claim 7, wherein the cargo has a molecular weight of greater than about 300 kDa.

9. The method of claim 2, wherein the compound of Formula (Ia) is present at nanomolar concentrations.

10. The method of claim 2, wherein following step b), the conjugate is internalized by the cells.

11. The method of claim 10, wherein internalization depends on cell surface heparan sulfate.

12. The method of claim 10, wherein internalization occurs through caveolae-mediated pathways.

13. A method of enhancing the intracellular uptake of liposomes, comprising:
  a) incorporating into a liposome or liposomal assembly a compound of Formula (Ia)

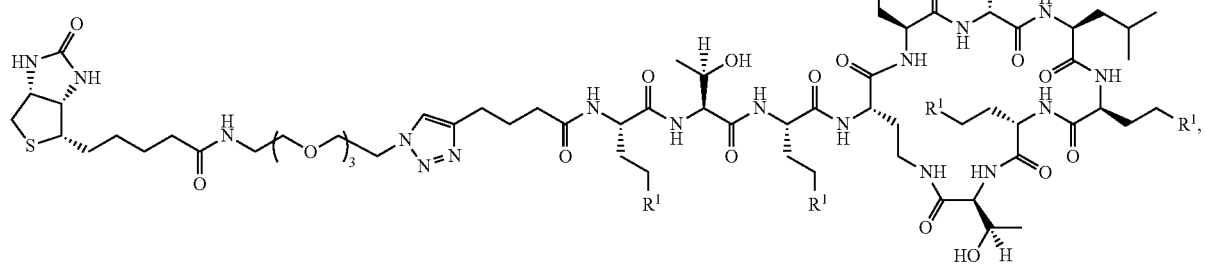

(Ia)

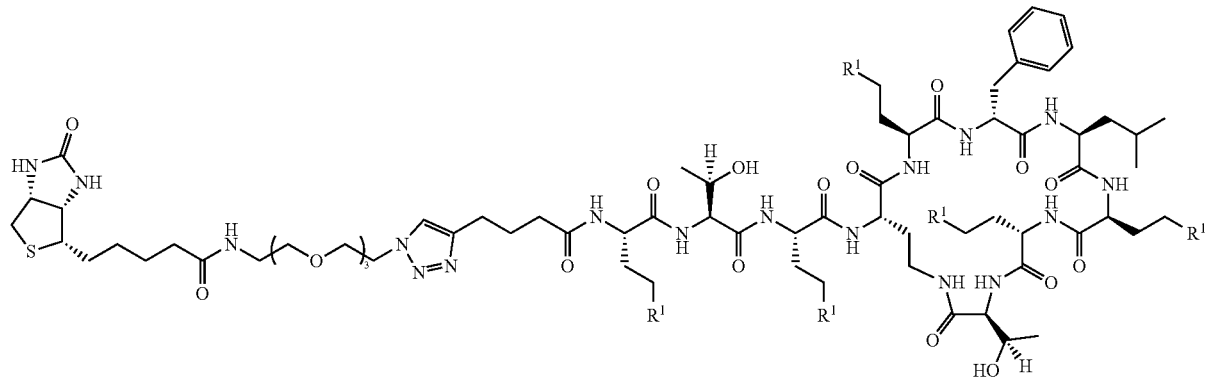

(Ia)

wherein:
 each $R^1$ is independently selected from among an ammonium group ($-NH_3^+$) and a guanidinium group ($-NH-C(=NH_2^+)-NH_2$);
 and
 b) contacting mammalian cells with the liposome or liposomal assembly comprising the compound of Formula (Ia).

14. The method of claim 13, wherein the liposome or liposomal assembly comprises cargo.

15. The method of claim 14, wherein the cargo is selected from among a large biomolecule, a protein, an oligonucleotide, a drug, and combinations thereof.

16. The method of claim 15, wherein the cargo has a molecular weight of greater than about 30, 50, 100, 200, 300, 500, or 1000 kDa.

17. The method of claim 16, wherein the cargo has a molecular weight of greater than about 300 kDa.

* * * * *